US010982211B2

(12) United States Patent
Kay et al.

(10) Patent No.: US 10,982,211 B2
(45) Date of Patent: *Apr. 20, 2021

(54) TRNA DERIVED SMALL RNAS (TSRNAS) INVOLVED IN CELL VIABILITY

(71) Applicant: The Board of Trustees of the Leland Stanford Junior University, Stanford, CA (US)

(72) Inventors: Mark A. Kay, Los Altos, CA (US); Hak Kyun Kim, Palo Alto, CA (US); Shengchun Wang, Union City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/700,973

(22) Filed: Dec. 2, 2019

(65) Prior Publication Data
US 2020/0199594 A1 Jun. 25, 2020

Related U.S. Application Data

(63) Continuation of application No. 15/216,546, filed on Jul. 21, 2016, now Pat. No. 10,633,655, which is a continuation of application No. 14/214,032, filed on Mar. 14, 2014, now Pat. No. 9,428,537.

(60) Provisional application No. 61/798,871, filed on Mar. 15, 2013.

(51) Int. Cl.
| C07H 21/04 | (2006.01) |
| C12N 15/113 | (2010.01) |
| C07H 21/02 | (2006.01) |
| A61K 45/06 | (2006.01) |
| A61K 31/606 | (2006.01) |
| A61K 31/635 | (2006.01) |
| A61K 31/712 | (2006.01) |

(52) U.S. Cl.
CPC ......... *C12N 15/113* (2013.01); *A61K 31/606* (2013.01); *A61K 31/635* (2013.01); *A61K 31/712* (2013.01); *A61K 45/06* (2013.01); *C07H 21/02* (2013.01); *C12N 2310/113* (2013.01); *C12N 2310/14* (2013.01); *C12N 2310/3231* (2013.01); *C12N 2320/31* (2013.01)

(58) Field of Classification Search
None
See application file for complete search history.

(56) References Cited

U.S. PATENT DOCUMENTS

| 5,801,154 A | 9/1998 | Baracchini et al. |
| 7,799,107 B2 | 9/2010 | Corney et al. |
| 2009/0326049 A1 | 12/2009 | Aristarkhov |
| 2010/0004320 A1 | 1/2010 | Elmen et al. |
| 2012/0110686 A1 | 5/2012 | Kay |

OTHER PUBLICATIONS

Garcia-Silva, Maria Rosa, et al. "Hints of tRNA-derived small RNAs role in RNA silencing mechanisms." Genes 3.4 (2012): 603-614.*
Garcia-Silva et al. "Hints of tRNA-Derived Small RNAs Role in RNA Silencing Mechanisms" Genes, vol. 3, pp. 603-614 (2012).
Haussecker et al., "Human tRNA-derived small RNAs in the global regulation of RNA silencing," RNA, 16:673-695 (2010).
Lee et al., "A novel class of small RNAs: tRNA-derived RNA fragments (tRFs)," Genes & Development, 23:2639-2649 (2009).
Martens-Uzunova, et al., "Beyond microRNA—Novel RNAs derived from small non-coding RNA and their implication in cancer," Cancer Letters, 340:201-211 (2013).
Maute et al., "tRNA-derived microRNA modulates proliferation and the DNA damage response and is down-regulated in B cell lymphoma," PNAS, 110(4):1404-1409 (2013).
Pederson, Thoru, "Regulatory RNAs derived from transfer RNA?," RNA, 16:1865-1869 (2010).
Simoes-Wust et al., "A Functionally Improved Locked Nucleic Acid Antisense Oligonucleotide Inhibits Bcl-2 and Bcl-xL Expression and Facilitates Tumor Cell Apoptosis," Oligonucleotides, 14:199-209 (2004).
Sobala, Andrew and Hutvagner, Gyorgy, "Transfer RNA-derived fragments: origins, processing, and functions," Advanced Review, 2:853-862 (2011).
Wengel et al., "LNA (Locked Nucleic Acid)," Nucleosides & Nucleotides, 18(6&7):1365-1370 (1999).

* cited by examiner

*Primary Examiner* — Kimberly Chong
(74) *Attorney, Agent, or Firm* — Morgan, Lewis & Bockius LLP

(57) ABSTRACT

The present invention features compositions and methods relating to tRNA-derived small RNAs (tsRNAs). Provided herein are oligonucleotide compositions that are complementary to tsRNAs, in particular leuCAGtsRNA, and methods of using the oligonucleotides for the regulation of respective tsRNA. Further provided are methods of inducing apoptosis through the inhibition of leuCAGtsRNA.

13 Claims, 28 Drawing Sheets

Specification includes a Sequence Listing.

```
leuCAG mature tRNA
GTCAGGATGGCCGAGCGGTCTAAGGCGCTGCGTTCAGGTCGCAGTCTCCCCTGGAGGCGTGGGTTCGAATCCCACTCCTGACACCA
LNA-leu3ts 18bp gapmer                                                  AATCcactcctgaCACC
LNA-leu3ts15PM mixmer                                                    AtCccAcTcCTgACa
LNA-leu3ts15MM1 mixmer                                                   AtCccAcTcTTgAGa
LNA-leu3ts15MM2 mixmer                                                   AtCccAgTcTTgACa
```

LNA-leu3ts 18 bp gapmer is SEQ ID NO: 11
LNA-leu3ts15PM (CAGPM) mixmer is SEQ ID NO: 2
LNA-leu3ts15MM1 (CAGMM1) is SEQ ID NO: 3
LNA-leu3ts15MM2 is (CAGMM2) SEQ ID NO: 4

Figure 2B

```
LeuCAG mature tRNA
GTCAGGATGGCCGAGCGGTCTAAGGCGCTGCGTTCAGGTCGCAGTCTCCCCTGGAGGCGTGGGTTCGAATCCCACTCCTGACACCA
LNA-leu5ts gapmer
GTCAGGATGGCCGAGCGGTC
    LNA-leuA       CGGTCTAAGGCGCTGCGT ()
           LNA-leuB    CTGCGTTCAGGTCGCAGTC
                  LNA-leuC     CAGTCTCCCCTGGAGGCG
                        LNA-leuD-6bp  CCCTGGAGGCGTGGGTTCG ()
                           LNA-leuD-4bp  CTGGAGGCGTGGGTTCGAA ()
                              LNA-leuD-2bp  GGAGGCGTGGGTTCGAATC ()
                                 LNA-leuD     AGGCGTGGGTTCGAATCCC ()
                                    LNA-leu3ts gapmer   AATCCCACTCCTGACACC ()
```

Figure 2C

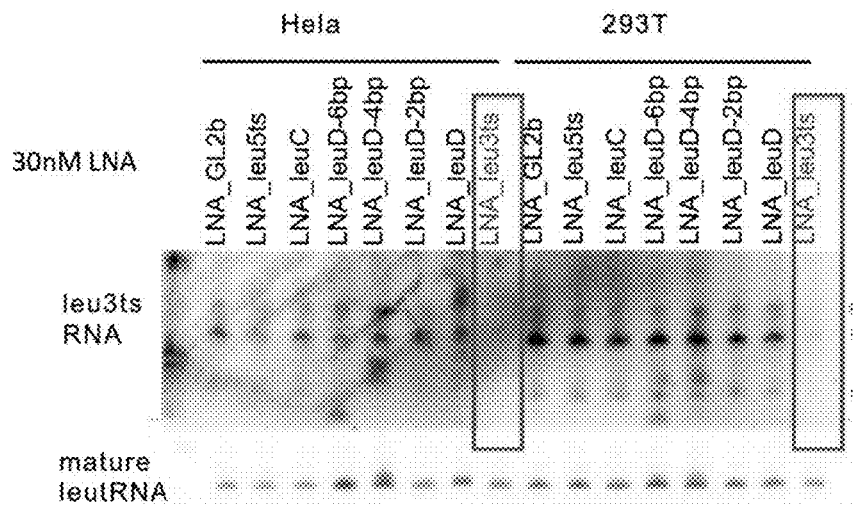

FIGURE 3
Figure 3A
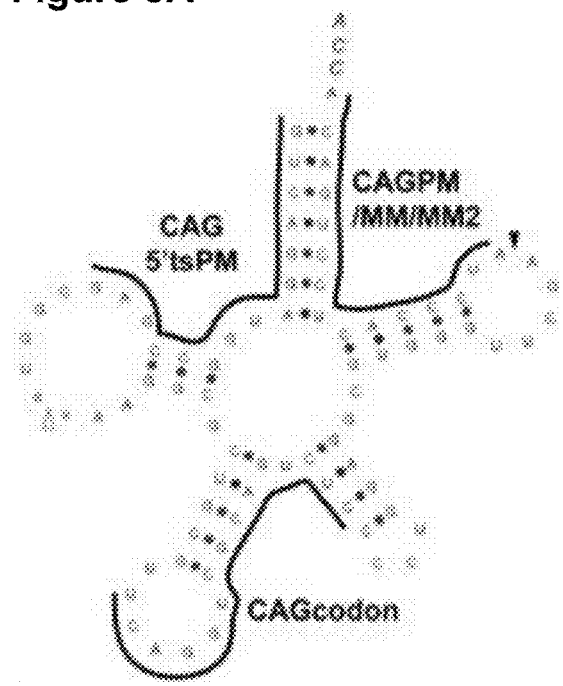
Figure 3B
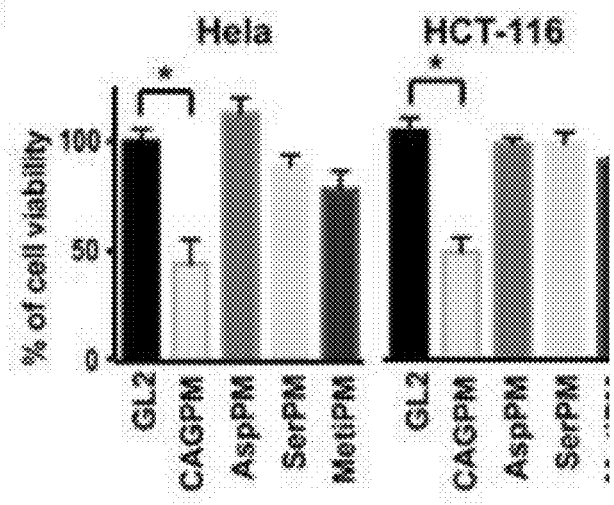
Figure 3C
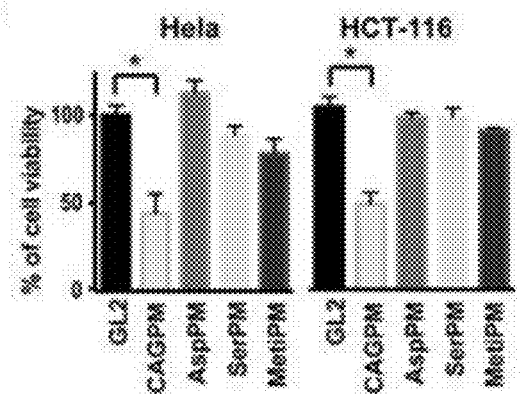
Figure 3D
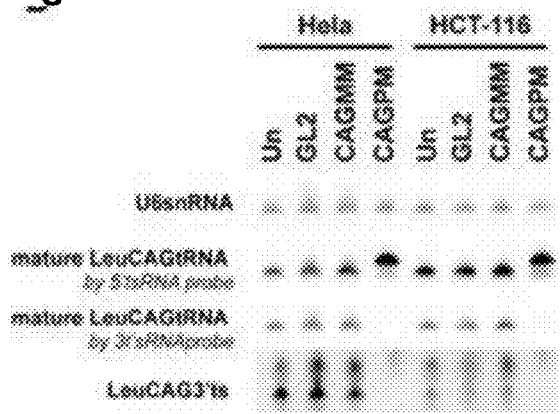

FIGURE 3 (Cont.)
Figure 3E
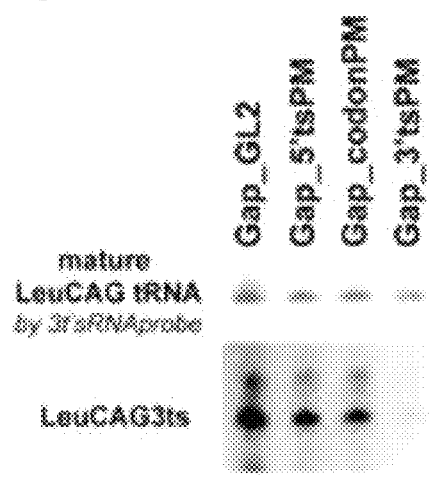
Figure 3F
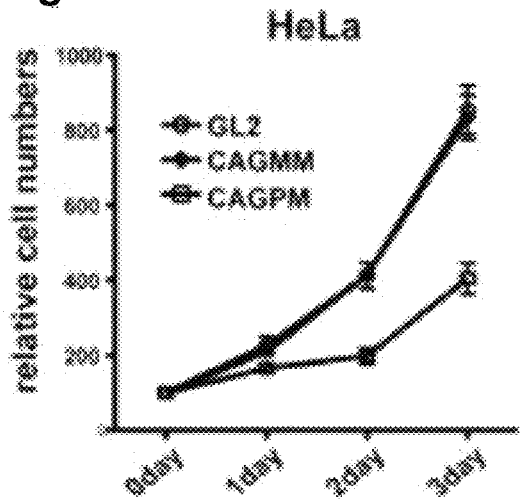
Figure 3G
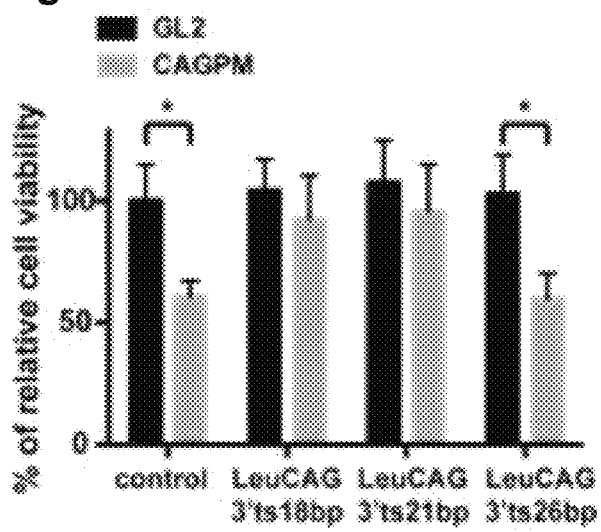
Figure 3H
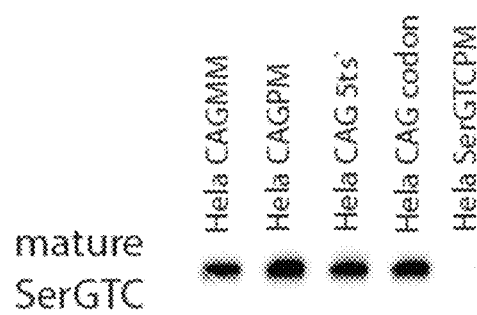

FIGURE 4
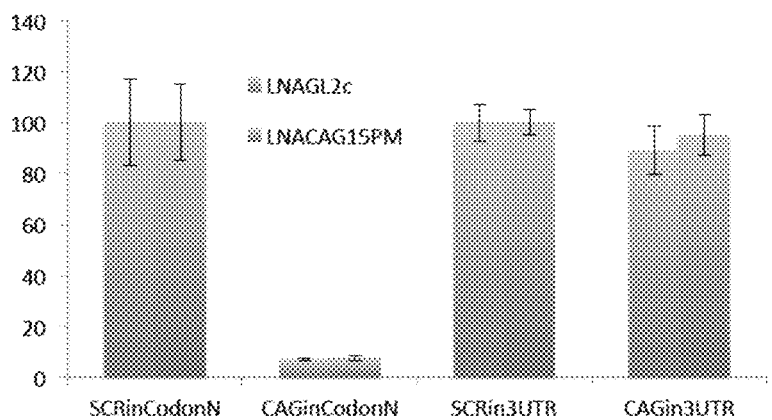

FIGURE 7
Figure 7A
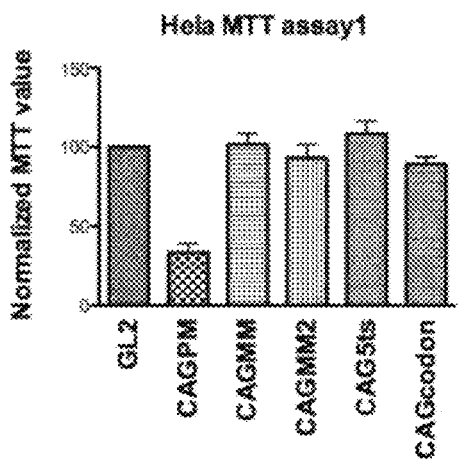
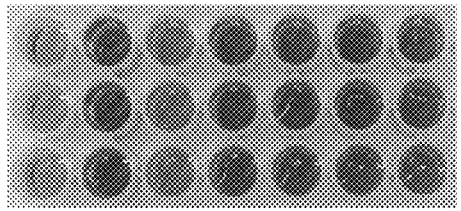
Figure 7B
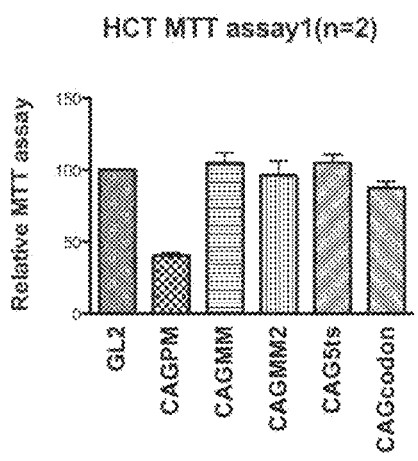
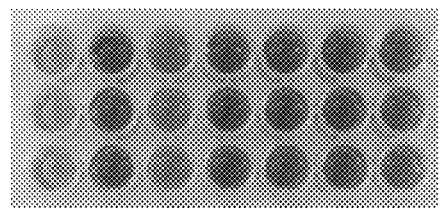
Figure 7C
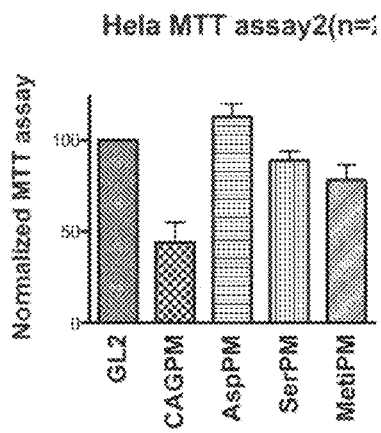
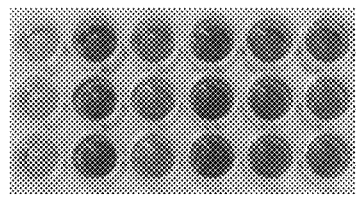
Figure 7D
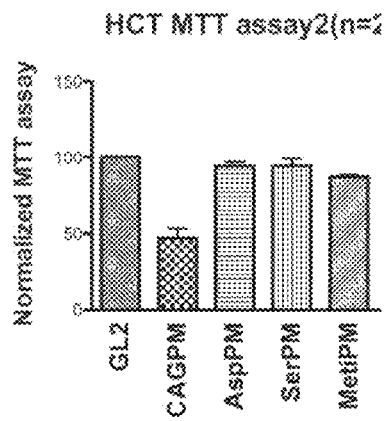
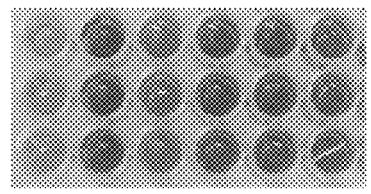

FIGURE 8
Figure 8A
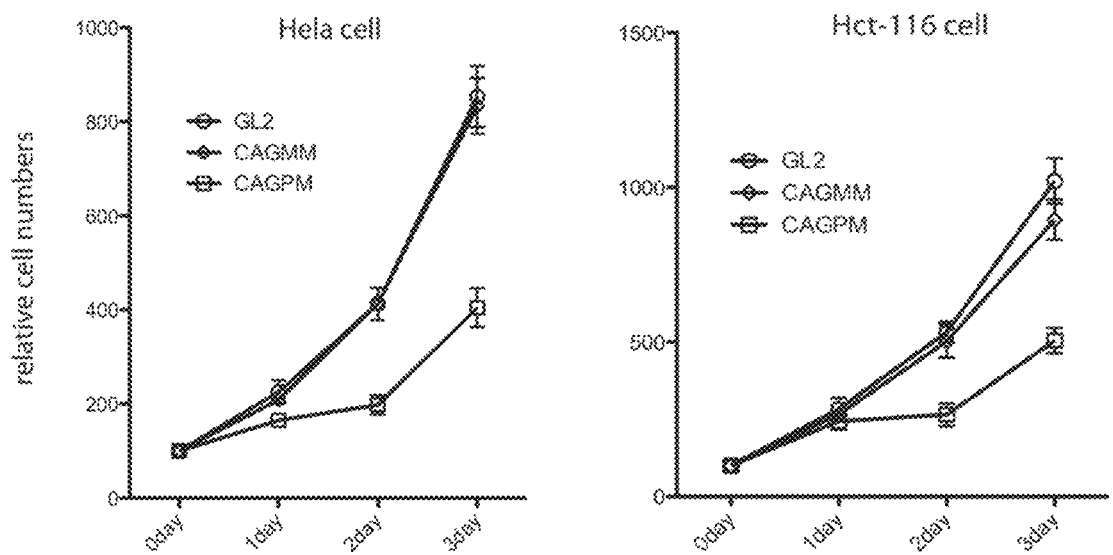
Figure 8B
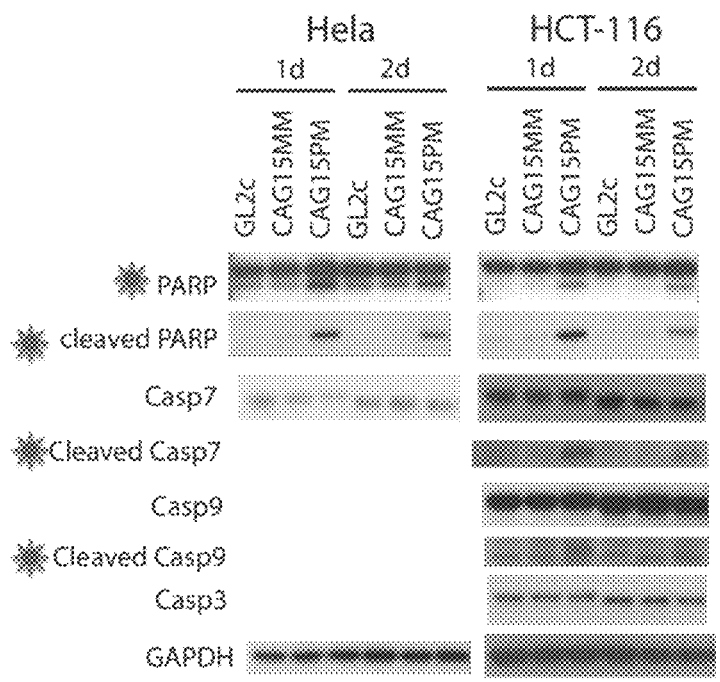

FIGURE 9
Figure 9A
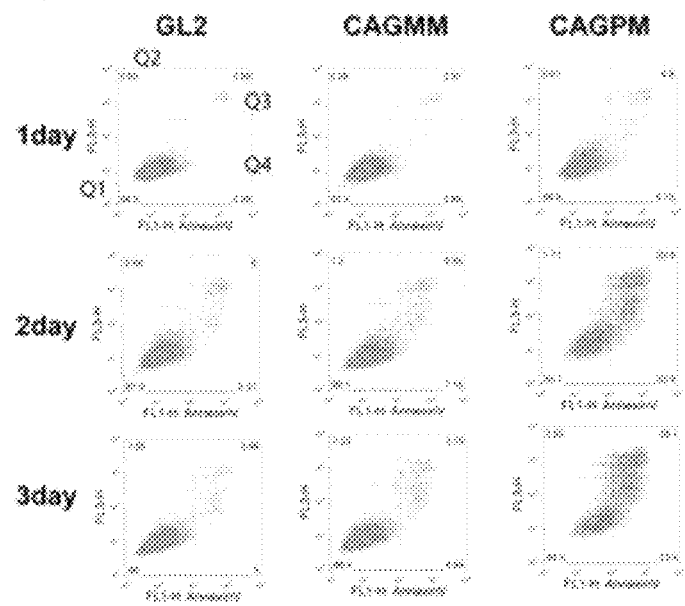
Figure 9B
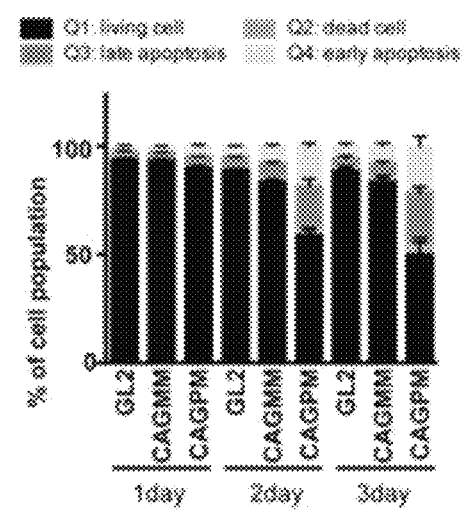
Figure 9C
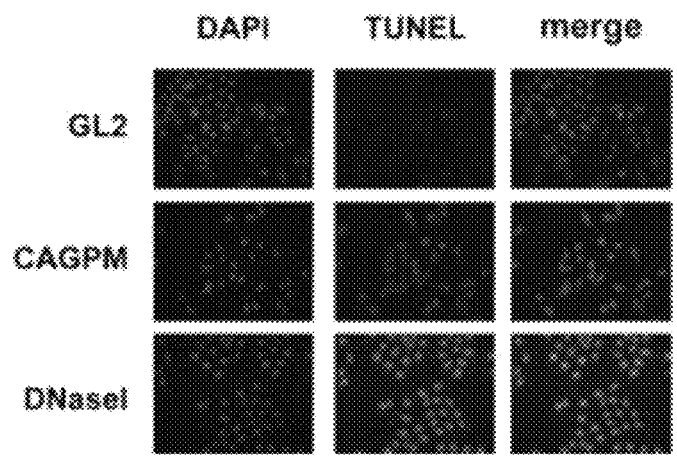
Figure 9D
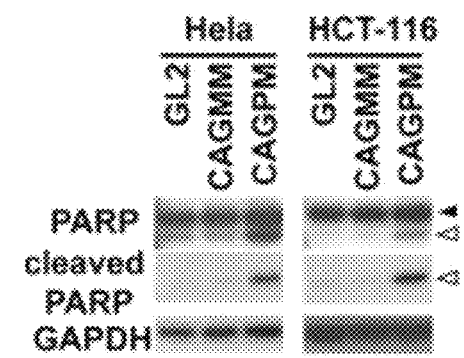

FIGURE 10
Figure 10A
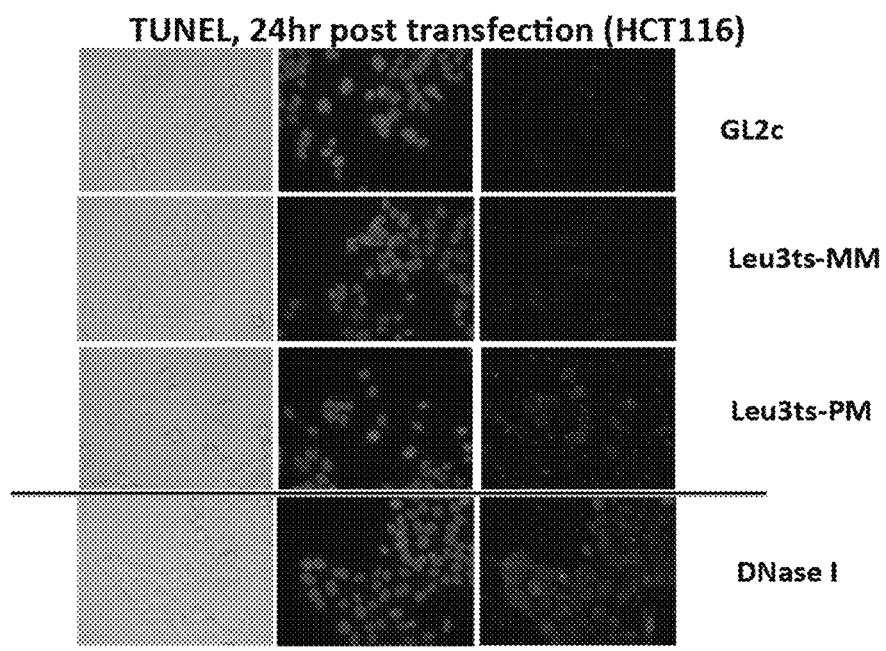
Figure 10B
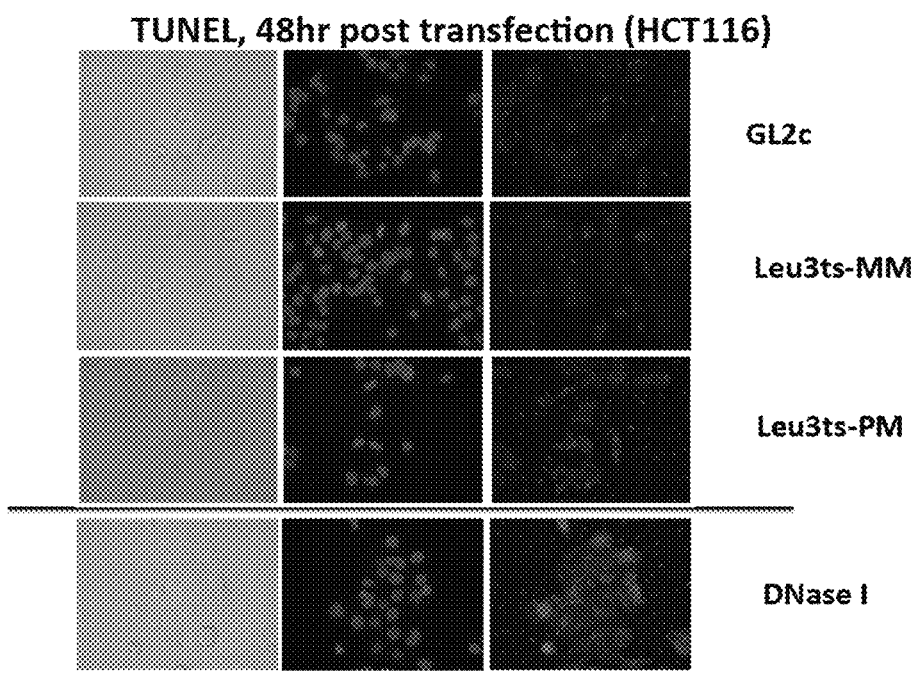

FIGURE 11
Cell cycle analysis
BrdU vs PI staining
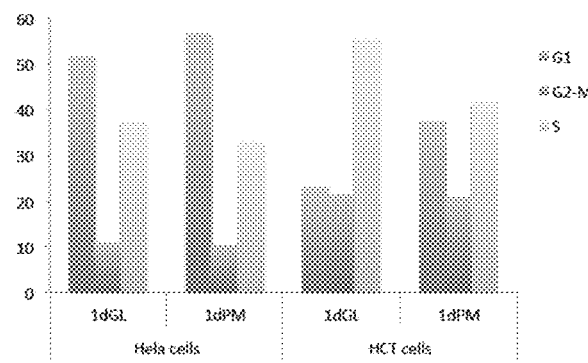
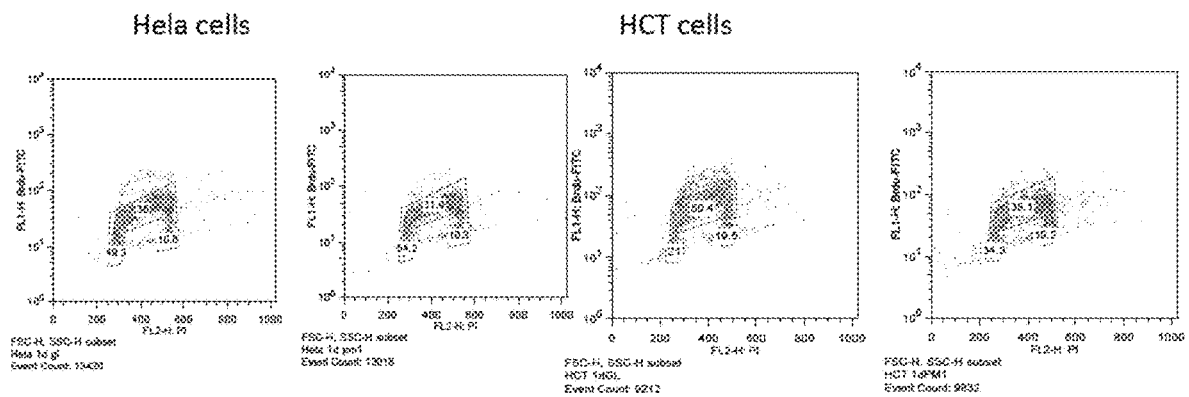

FIGURE 12
Figure 12A
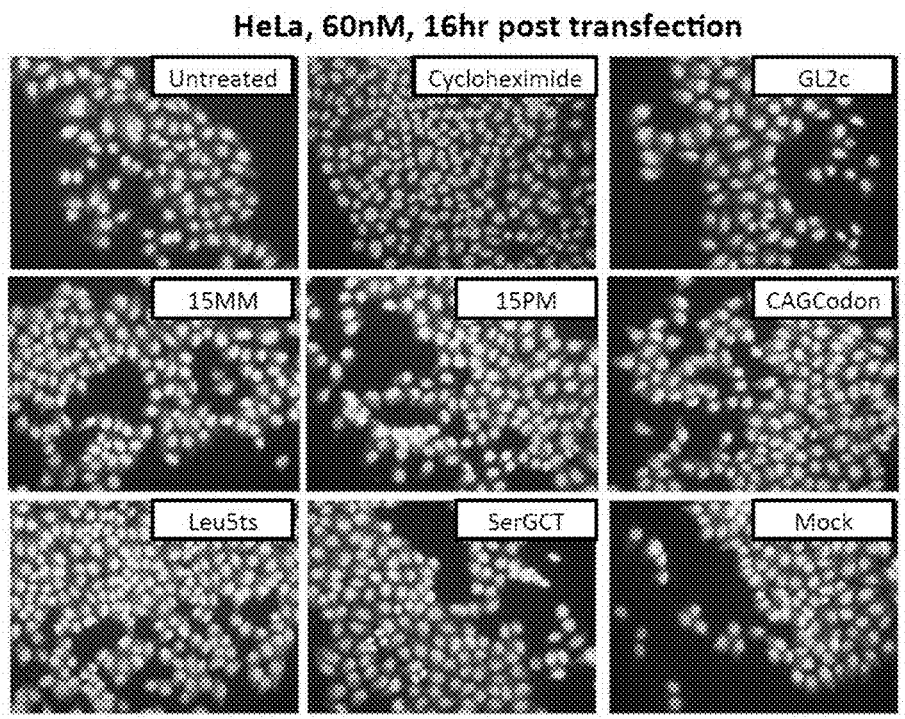
Figure 12B
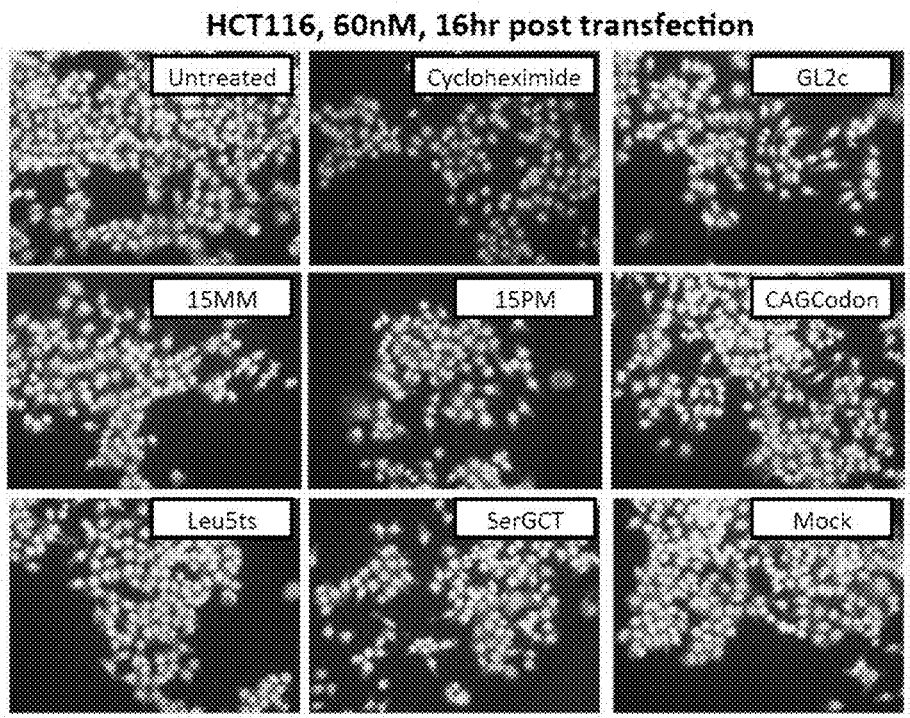

FIGURE 13 (Cont.)
Figure 13B
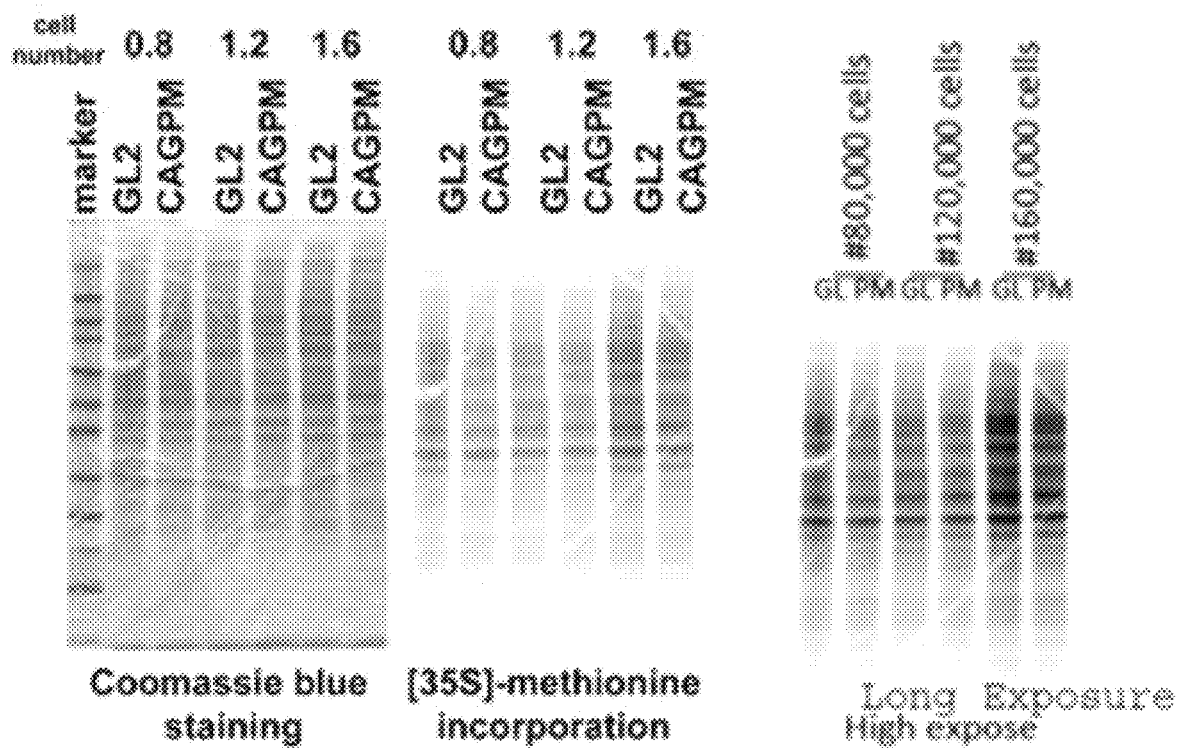
Figure 13C
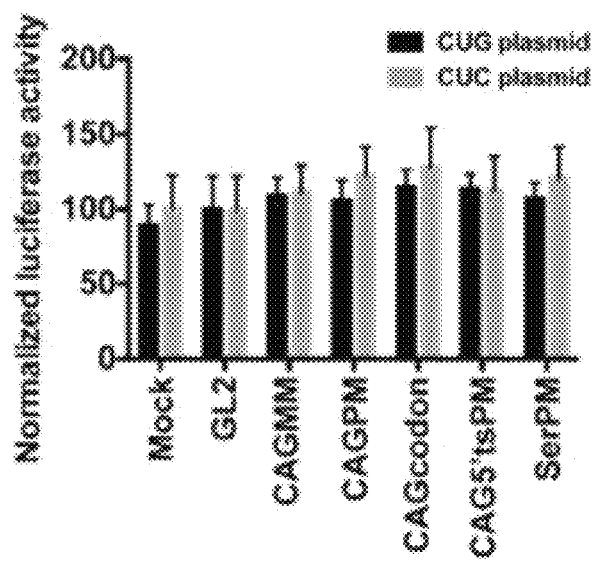

FIGURE 14
Figure 14A
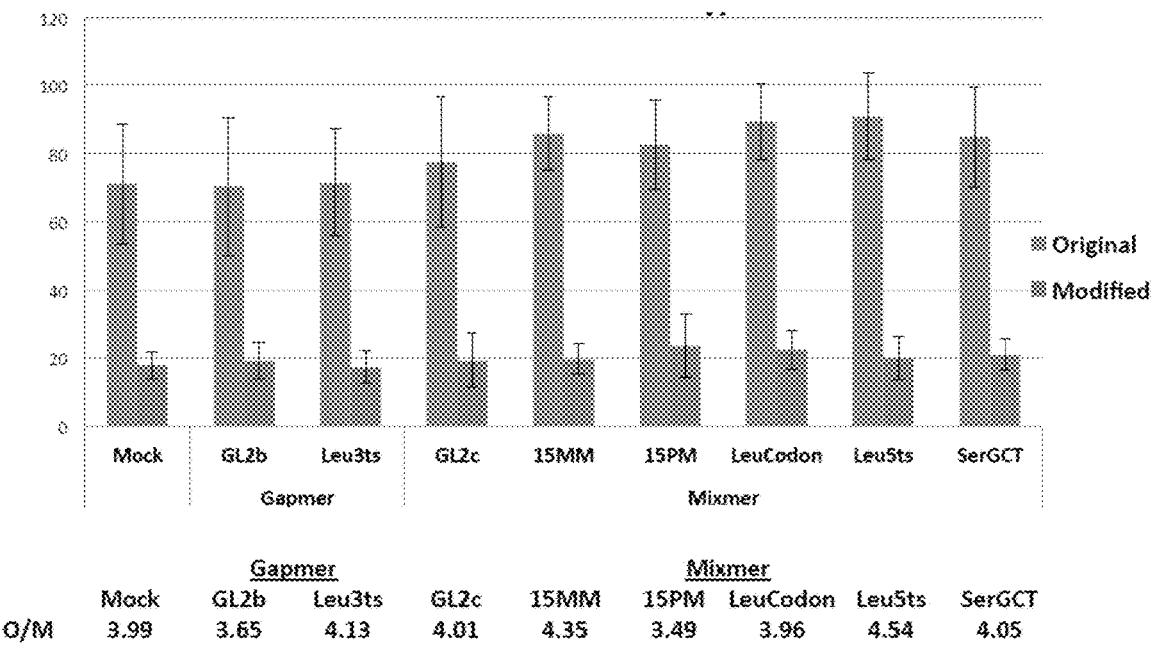
Figure 14B
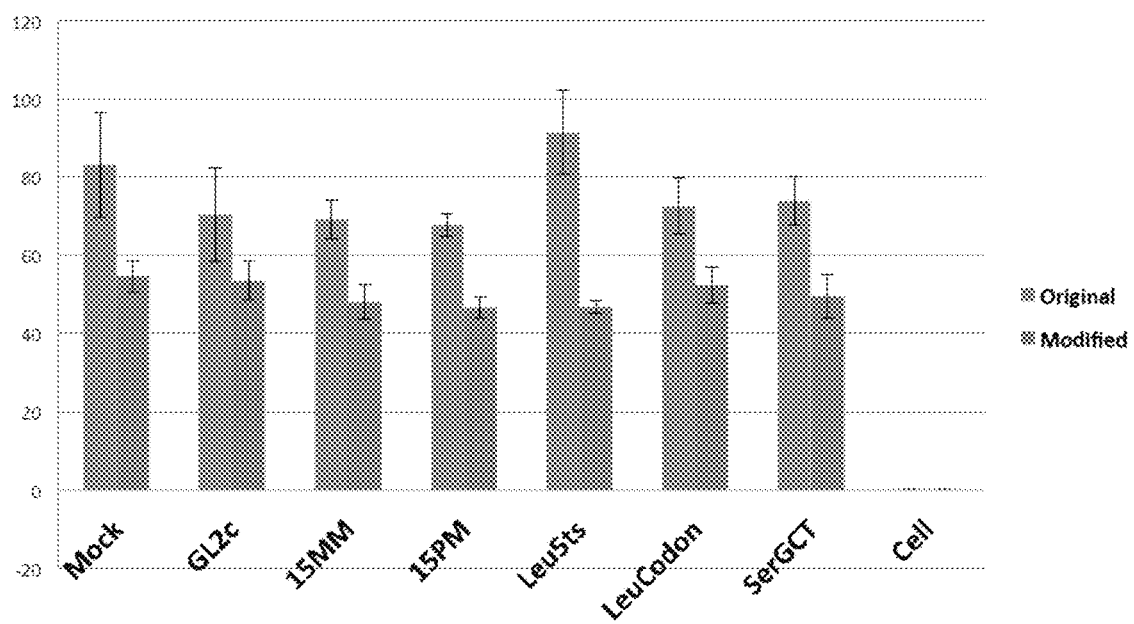

FIGURE 15
Figure 15A
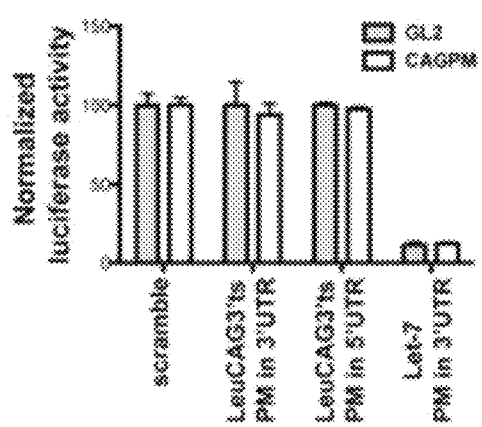
Figure 15B
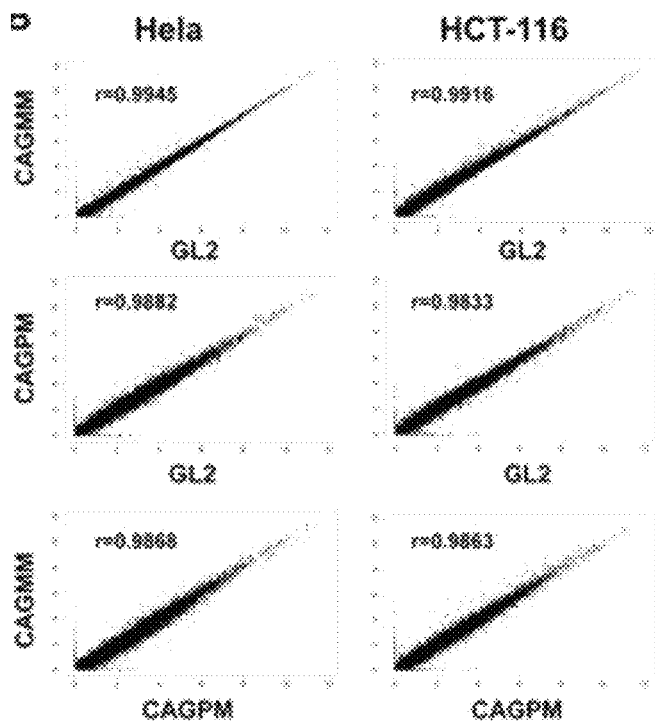
Figure 15C
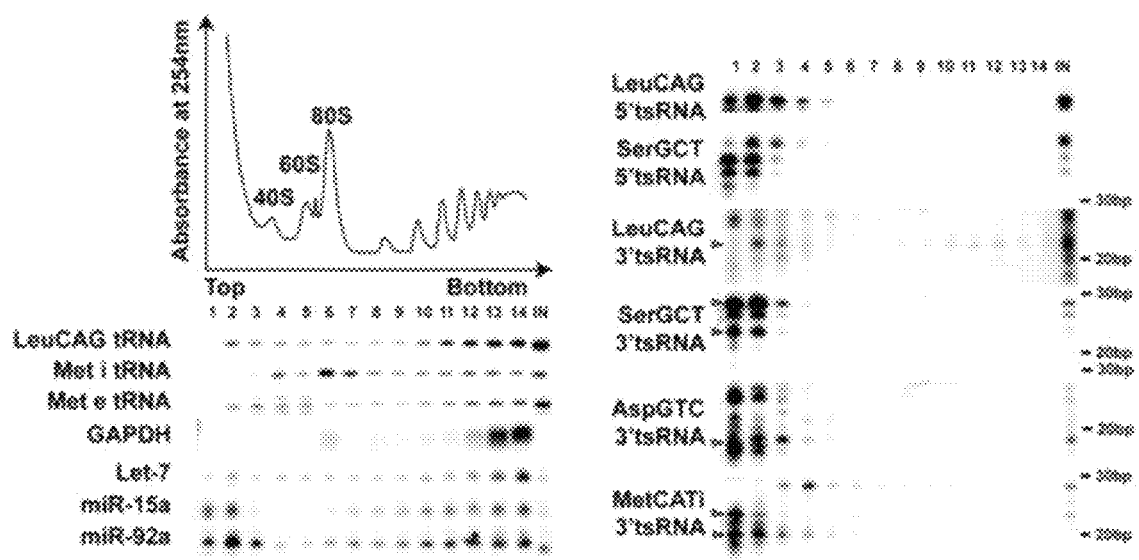

FIGURE 16
Figure 16A
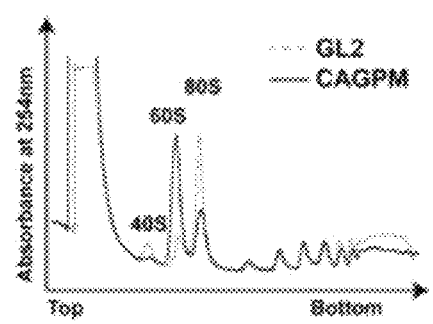
Figure 16B
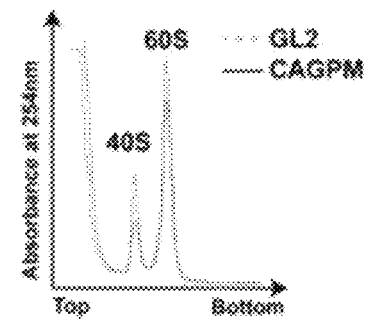
Figure 16C
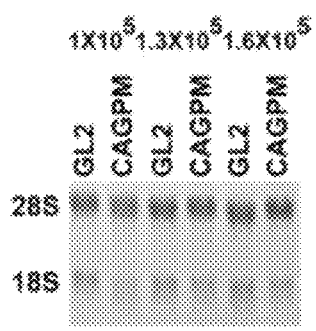
Figure 16D
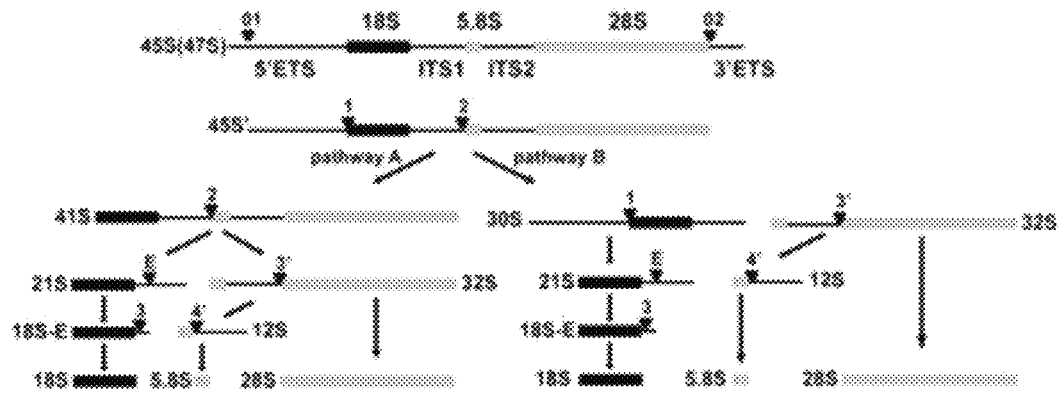
Figure 16E
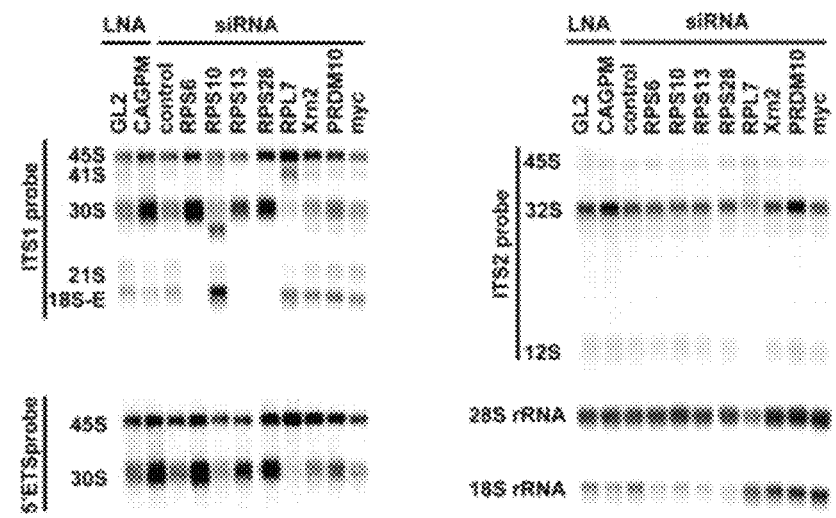

FIGURE 17
Figure 17A
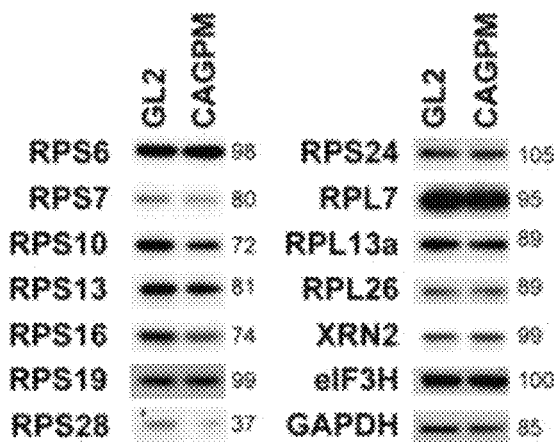
Figure 17B
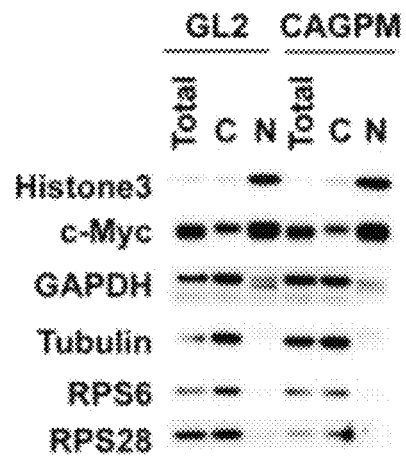
Figure 17C
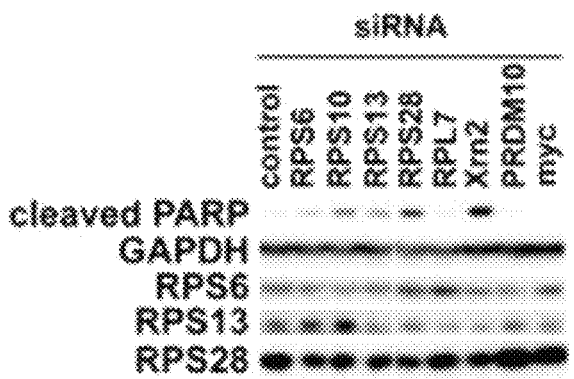
Figure 17D
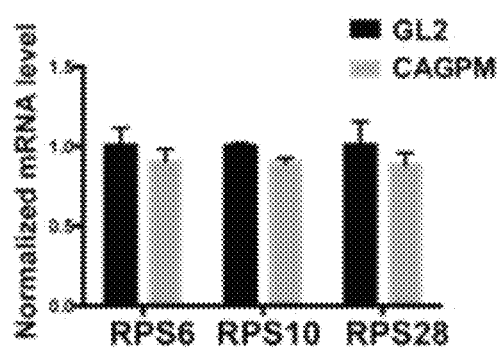
Figure 17E
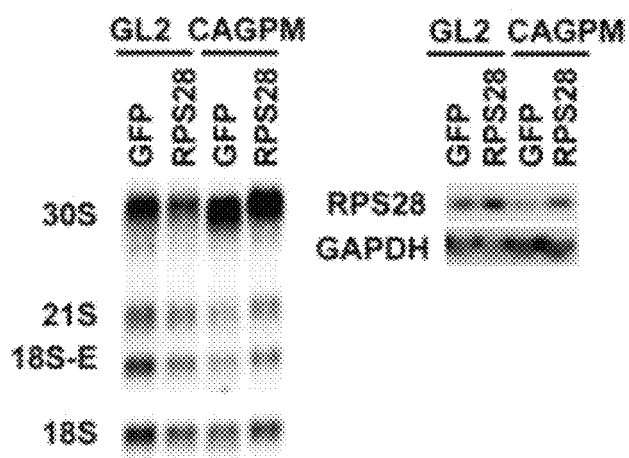

FIGURE 18
Figure 18A
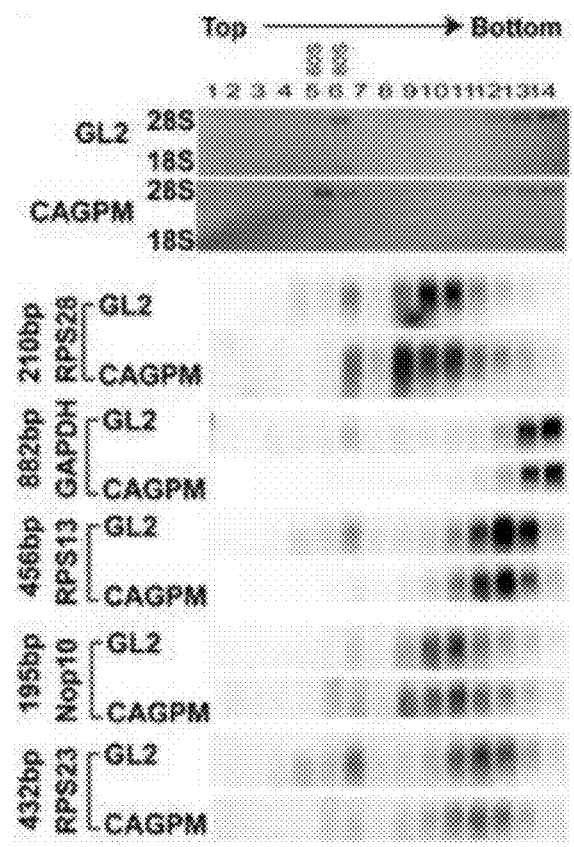
Figure 18B
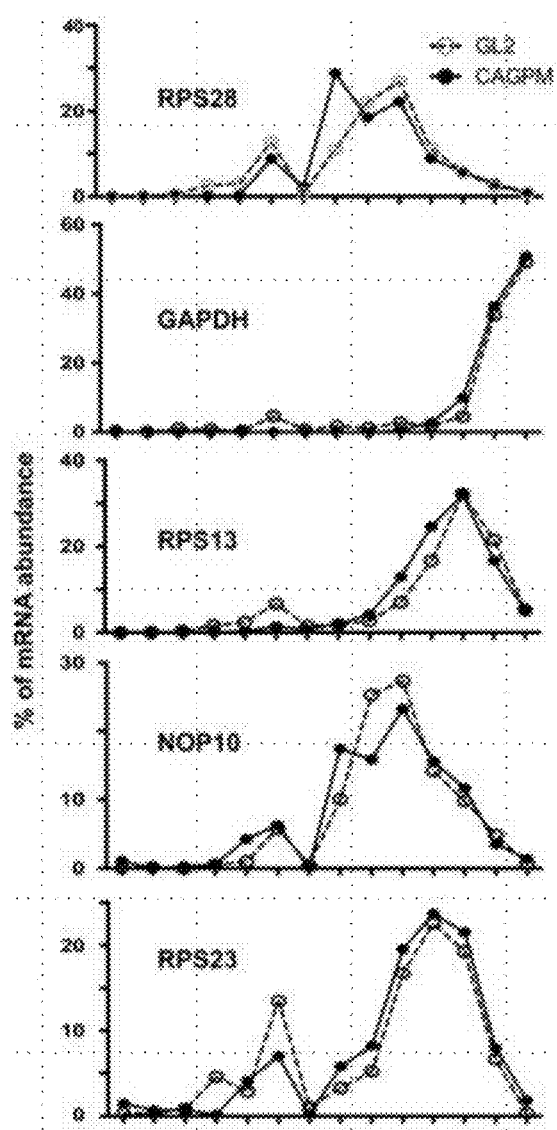
Figure 18C
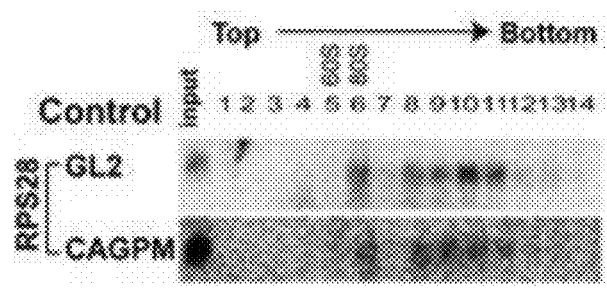
Figure 18D

FIGURE 19
Figure 19A
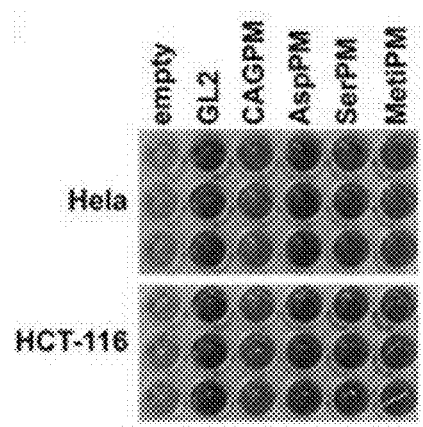
Figure 19B
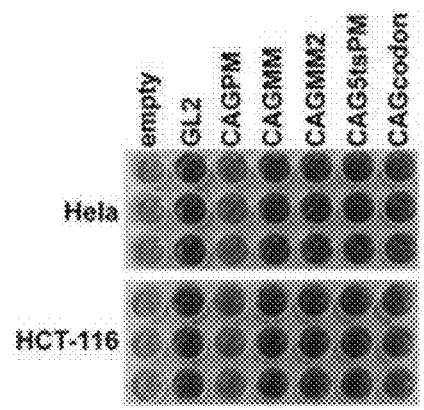
Figure 19C
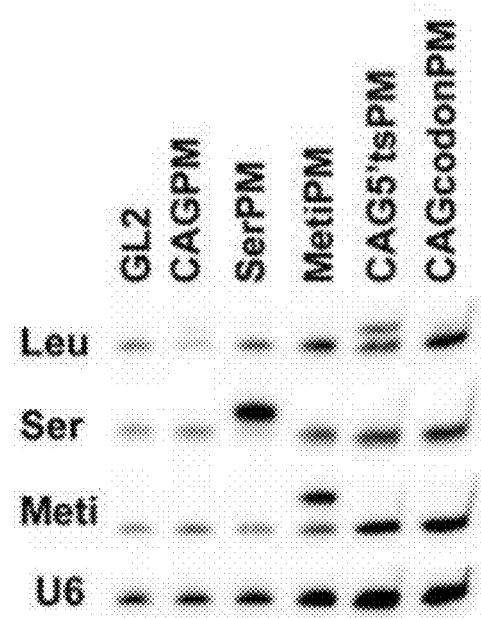
Figure 19D
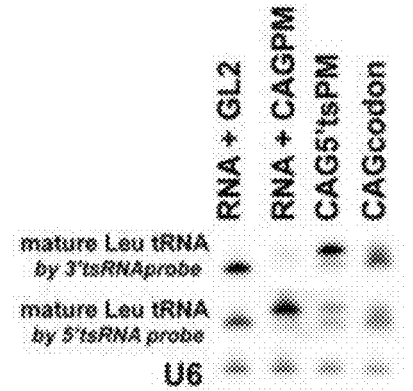
Figure 19E
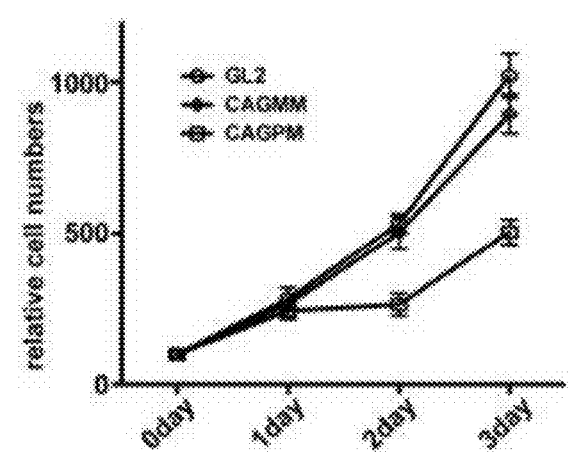

FIGURE 21
Figure 21A
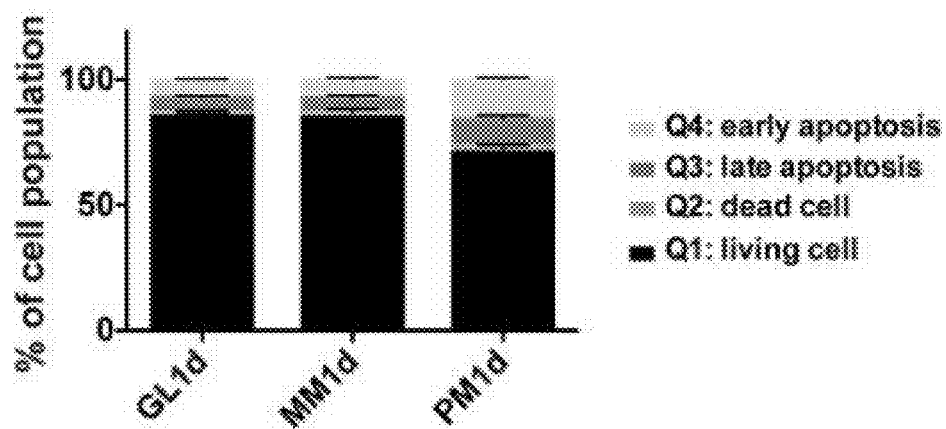
Figure 21B
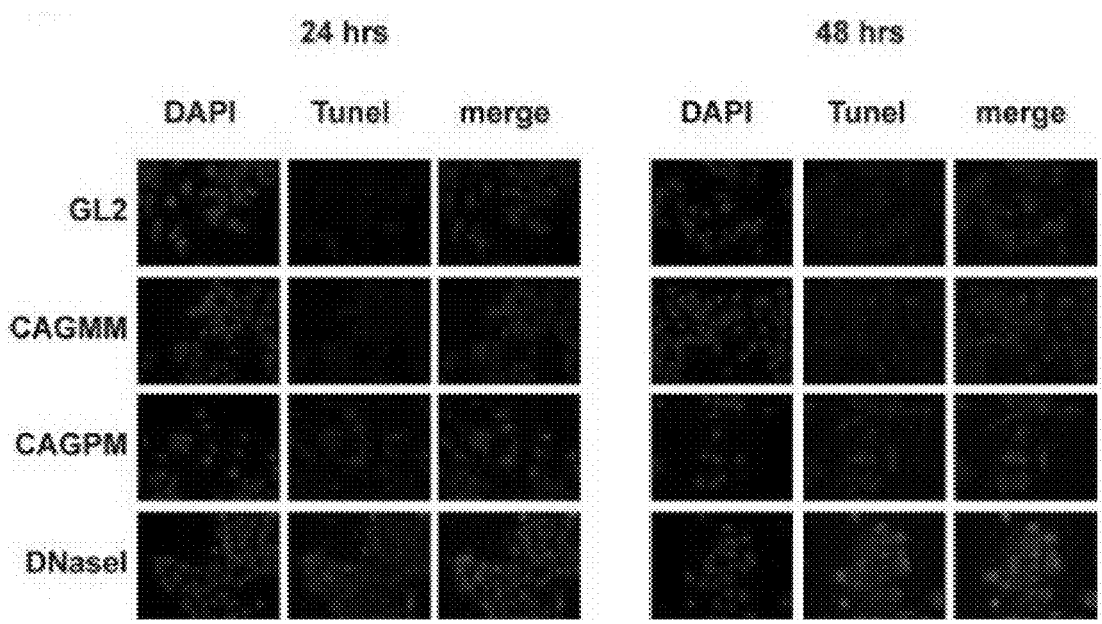

FIGURE 22
Figure 22A
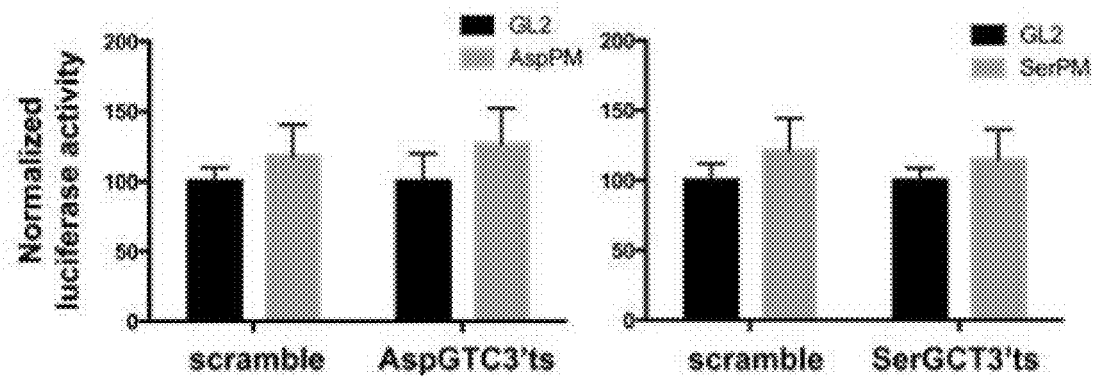
Figure 22B
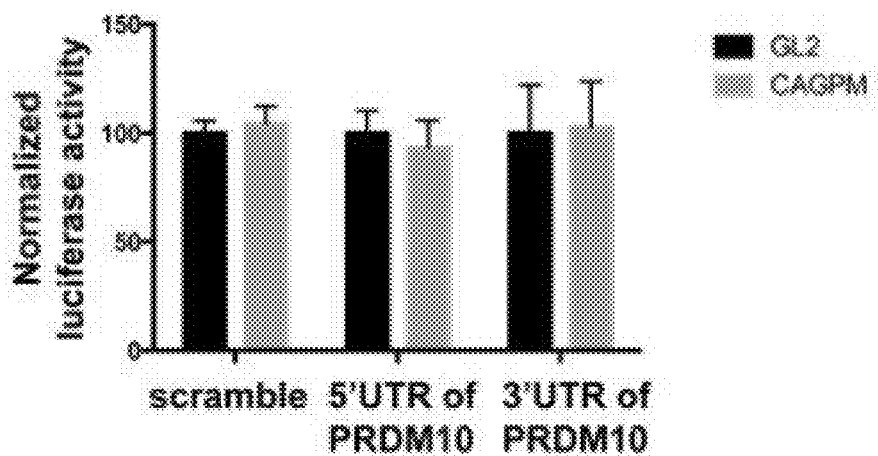

FIGURE 23
Figure 23A
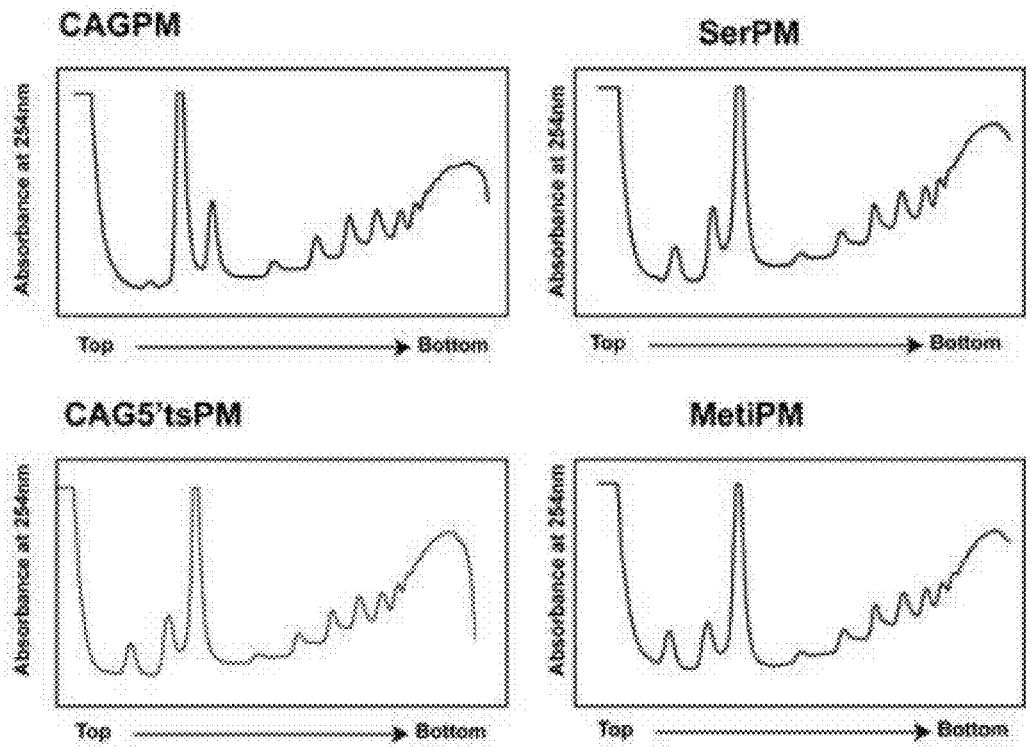
Figure 23B
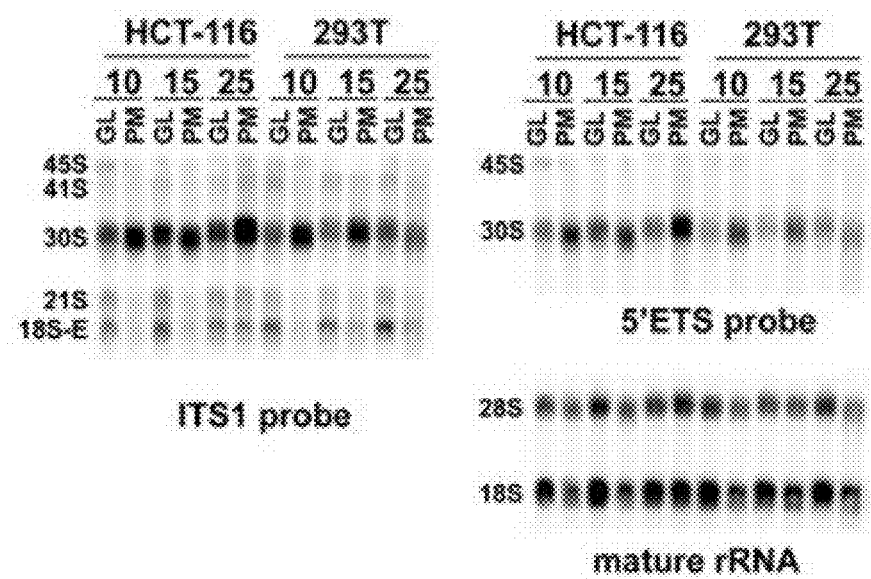

FIGURE 24
Figure 24A
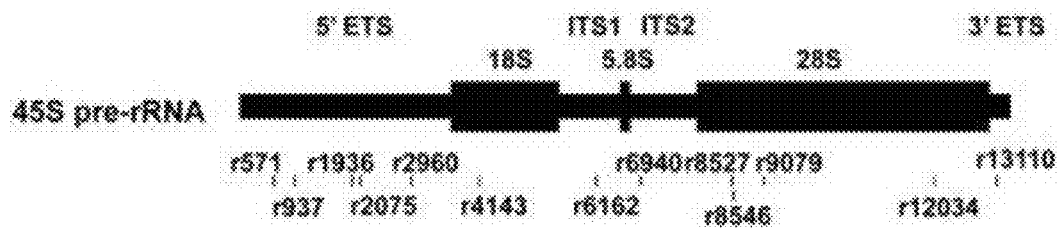
Figure 24B
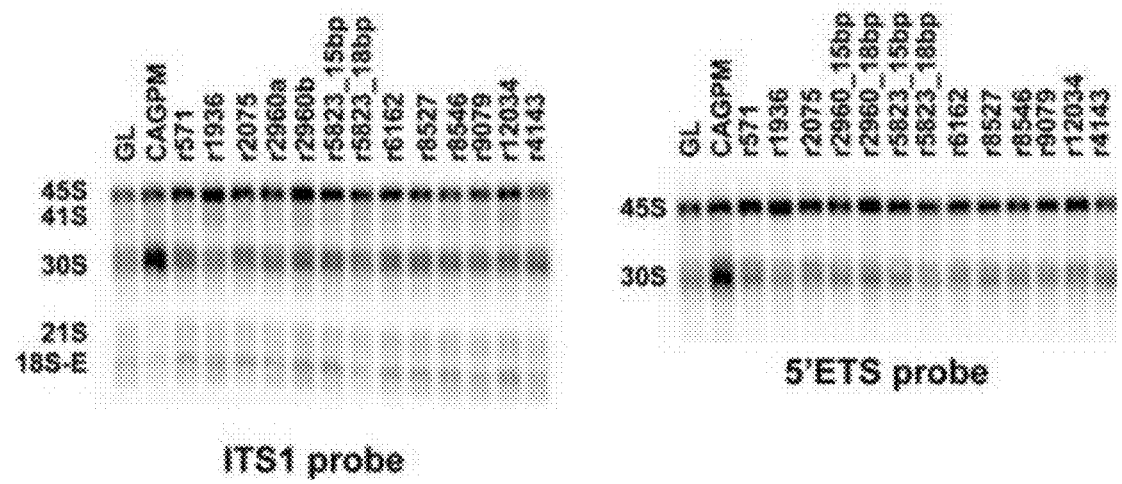
Figure 24C
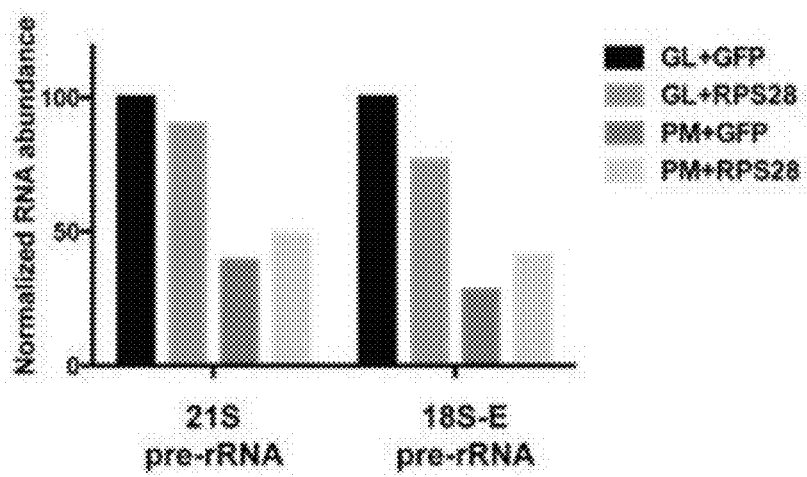

FIGURE 25
Figure 25A
Figure 25B
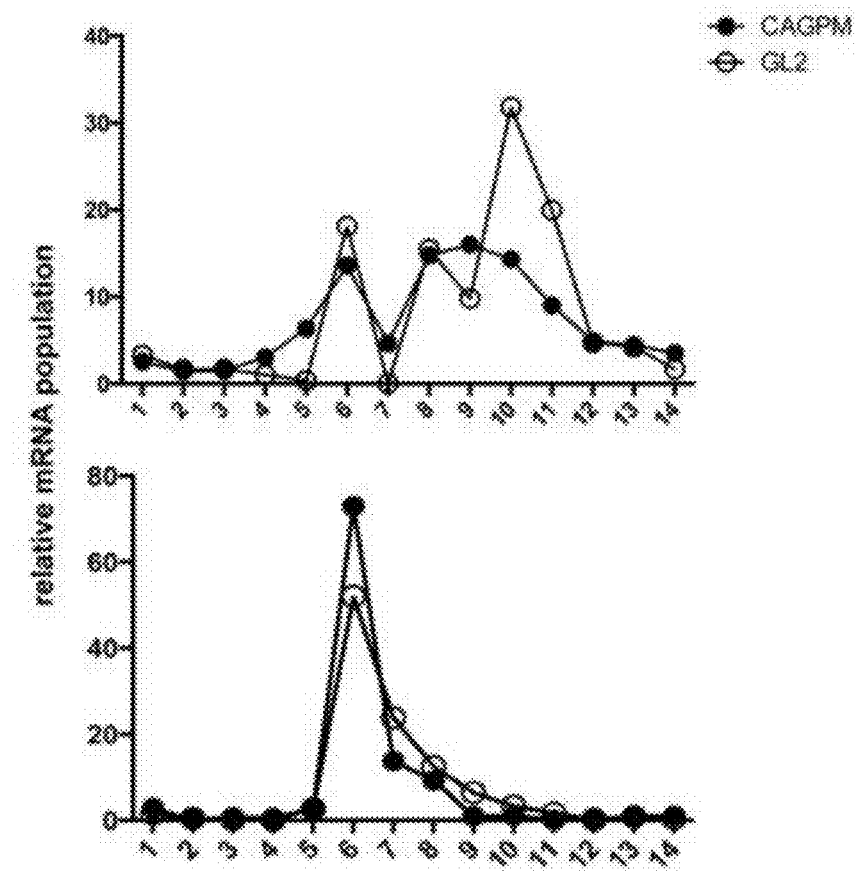

FIGURE 26

| Cell line | Gene | Locus | sample1 | sample2 | Test status | FPKM of sample1 (A) | FPKM of sample2 (B) | log2(B/A) | Test stat | p value | q value | Significant |
|---|---|---|---|---|---|---|---|---|---|---|---|---|
| | PRDM10 | chr11:129769600-129875381 | CAGPM | CAGMM | OK | 9.80217 | 2.70613 | -1.85687 | 3.69712 | 0.000218059 | 0.00604809 | yes |
| | RN5-8S1 | chrUn_gl000220:155996-156152 | CAGPM | CAGMM | OK | 19.4024 | 290.382 | 3.90365 | -4.93891 | 7.86E-07 | 4.36E-05 | yes |
| | SERF1A | chr5:70196489-70214357 | CAGPM | CAGMM | OK | 0.210349 | 14.6821 | 6.12513 | -4.45229 | 8.50E-06 | 0.00036091 | yes |
| HCT-116 | SNORA24 | chr4:119199916-119200978 | CAGPM | CAGMM | OK | 448.828 | 3401.16 | 2.92179 | -3.74523 | 0.000180232 | 0.00515351 | yes |
| | CHRAC1 | chr8:141521396-141527252 | CAGPM | GL2 | OK | 36.092 | 7.27289 | -2.31108 | 3.52186 | 0.000428536 | 0.0108258 | yes |
| | NCRNA00241 | chr6:161551056-161695107 | CAGPM | GL2 | OK | 2.25452 | 0.059315 | -5.24828 | 3.16507 | 0.00155046 | 0.0321354 | yes |
| | PRDM10 | chr11:129769600-129875381 | CAGPM | GL2 | OK | 9.80217 | 2.29213 | -2.09641 | 3.20317 | 0.00135924 | 0.0287553 | yes |
| | ANXA8 | chr10:48255224-48271368 | CAGPM | CAGMM | OK | 4.97334 | 0.546279 | -3.1865 | 3.48641 | 0.00048955 | 0.0121219 | yes |
| | CHRAC1 | chr8:141521396-141527252 | CAGPM | CAGMM | OK | 37.6902 | 8.38014 | -2.16914 | 3.20498 | 0.0013507 | 0.0286302 | yes |
| | IFFO1 | chr12:6648693-6665249 | CAGPM | CAGMM | OK | 0.943509 | 0.0984071 | -3.2612 | 3.21617 | 0.00129912 | 0.0277014 | yes |
| | NOTCH3 | chr19:15270443-15311792 | CAGPM | CAGMM | OK | 0.862768 | 0.0331455 | -4.70209 | 3.63295 | 0.000280198 | 0.00749413 | yes |
| | POMT1 | chr9:134378288-134406662 | CAGPM | CAGMM | OK | 3.54195 | 0.431033 | -3.03867 | 3.84693 | 0.000119609 | 0.00361911 | yes |
| Hela | PRDM10 | chr11:129769600-129875381 | CAGPM | CAGMM | OK | 6.22038 | 1.93959 | -1.68125 | 3.03177 | 0.00243124 | 0.0467227 | yes |
| | ATP5J | chr21:27096790-27144771 | CAGPM | GL2 | OK | 29.1165 | 102.069 | 1.80963 | -3.10292 | 0.00191624 | 0.0382866 | yes |
| | GAGE12D | chrX:49344540-49351917 | CAGPM | GL2 | OK | 66.9014 | 20.3104 | -1.71982 | 3.52082 | 0.000430212 | 0.0108587 | yes |
| | IFIT3 | chr10:91087601-91100725 | CAGPM | GL2 | OK | 40.7549 | 14.4314 | -1.49776 | 3.33695 | 0.000847025 | 0.0193277 | yes |
| | PRDM10 | chr11:129769600-129875381 | CAGPM | GL2 | OK | 6.22038 | 1.99156 | -1.64311 | 3.3735 | 0.000742182 | 0.017292 | yes |

TRNA DERIVED SMALL RNAS (TSRNAS) INVOLVED IN CELL VIABILITY

CROSS-REFERENCE TO RELATED APPLICATIONS

This application is a continuation of U.S. patent application Ser. No. 15/216,546, filed Jul. 21, 2016, which is a continuation of U.S. patent application Ser. No. 14/214,032, filed Mar. 14, 2014, now U.S. Pat. No. 9,428,537, which claims the benefit of U.S. Provisional Application No. 61/798,871, filed Mar. 15, 2013, the disclosure of which is incorporated herein by reference in its entirety for all purposes.

STATEMENT AS TO RIGHTS TO INVENTIONS MADE UNDER FEDERALLY SPONSORED RESEARCH OR DEVELOPMENT

This invention was made with Government support under contract DK78424 awarded by the National Institutes of Health. The Government has certain rights in this invention.

BACKGROUND OF THE INVENTION tRNA-derived small RNA (tsRNA) are small RNAs that are derived from the cleavage of tRNA. tRNA fragments of 30-35 nucleotides have been identified in bacteria, fungi, plants, and animals (Lee and Collins, *J. Biol. Chem.*, 280: 42744-9 (2005); Haiser et al. *Nucleic Acids Res.* 36:732-41 (2008); Jochl et al. *Nucleic Acids Res.* 36:2677-89 (2008); Kawaji et al BMC Genomics 9:157 (2008); Li et al. *Nucleic Acids Res.* 36:6048-55 (2008); Thompson et al. *RNA* 14:2095-103 (2008); and Zhang et al. *Plant Physiol.* 150: 378-87 (2009)). There are numerous different tsRNAs in the cell and the functions of how each of these small RNAs interact and function with other cellular components is not completely known.

Mature tRNAs are essential for mRNA translation in their role of transferring amino acids to a growing polypeptide chain. However, tRNA fragments have recently been identified as a source of non-coding RNAs (reviewed in (Martens-Uzunova et al., 2013; Sobala and Hutvágner, 2011)). tRNA fragments are classified into two classes based on their sizes. The longer 30-35 nt RNA species are called tRNA halves and generated by the endonuclease angiogenin. There is growing evidence that tRNA halves are involved in cellular stress response, cell proliferation, and apoptosis.

The other 18-26 nt non-coding RNAs are called small tRNA fragments (tRF) or tRNA-derived small RNA (tsRNA), which have been classified into three groups: 5'tsRNA (tRF-5 or 5'tRF), type I tsRNA (3'tsRNA, tRF-3, or 3'CCAtRF), and type II tsRNA (tRF-1 or 3'U tRF) (Haussecker et al., 2010; Lee et al., 2009). The 5' and 3'tsRNAs are derived from the 5' and 3' end of mature tRNAs, respectively. The 3'tsRNA contains the CCA sequence added to 3'end during tRNA maturation. The tsRNA type II is processed from the 3' precursor of tRNA, which ends in polyuridine due to termination by RNA polymerase III.

The biogenesis of tsRNAs is not clear. For the generation of type II tsRNAs and 5'tsRNAs there are mixed reports supporting the role of dicer, and one study supporting the role of the tRNA processing enzyme RNaseZ and tRNA 3'-endonuclease, ELAC2, in type II generation (Babiarz et al., 2008; Cole et al., 2009; Haussecker et al., 2010; Lee et al., 2009), while the generation of the 3'tsRNAs (type I) is unlikely related to dicer processing (Babiarz et al., 2008; Li et al., 2012).

The biological role of tsRNAs is not well understood and there have been attempts to establish whether tsRNAs are associated with Ago (Argonaute) proteins, the key component in RISC (RNA-induced silencing complex) (reviewed in (Bartel, 2004; Croce and Calin, 2005; Kim and Kim, 2012; Pederson, 2010)). The evidence for the presence of tsRNA in RISC comes from studies showing that certain tsRNAs can associate with over-expressed Argonaute proteins (Haussecker et al., 2010; Maute et al., 2013). Furthermore, HisGTG and LeuCAG3'tsRNA as well as GlyGCC3'tsRNA have been found to be associated with endogenous Ago2 protein (Li et al., 2012; Maute et al., 2013). In addition, there is some implication that the over-expressed GlyGCC3'tsRNA from a miRNA hairpin or genomic tRNA can reduce endogenous gene expression through base-pairing with complementary target mRNAs in the 3'UTR (Maute et al., 2013). Synthetic S'tsRNAs can inhibit protein translation regardless of their ability to base-pair with complementary target mRNAs, implying that the cellular function of S'tsRNA differs from microRNA (Sobala and Hutvágner, 2013).

tRNA-derived small RNAs are also found in lower organisms. In *Tetrahymena*, a 18-22 nt fragment of the 3'tRNA is associated with Twi12 (Tetrahymena Piwi12), which is essential for cell growth, and does not have trans-gene silencing activity (Couvillion et al., 2010). Twi12 activates Xrn2 for RNA processing in the nucleus (Couvillion et al., 2012). In *Haloferax volcanii*, the Val5'tsRNA binds to the ribosome, and a synthetic Val5'tsRNA was shown to inhibit translation (Gebetsberger et al., 2012). All of these various findings suggest that some of these tsRNAs play important roles in various aspects of cellular function.

Unlike the type II tsRNAs, the 5'tsRNAs and 3'tsRNAs (type I tsRNAs) are derived from mature tRNAs making their sequences more highly conserved between species. As reported herein, these tsRNAs play an important role in cell viability. Specifically, when tsRNAs are depleted, cells undergo apoptosis.

Apoptosis is a genetically programmed cellular event that is characterized by well-defined morphological features, such as cell shrinkage, chromatin condensation, nuclear fragmentation, and membrane blebbing. Kerr et al. *Br. J. Cancer*, 26, 239-257 (1972); Wyllie et al. *Int. Rev. Cytol.*, 68, 251-306 (1980). It plays an important role in normal tissue development and homeostasis, and defects in the apoptotic program are thought to contribute to a wide range of human disorders ranging from neurodegenerative and autoimmunity disorders to neoplasms. Thompson, *Science*, 267, 1456-1462 91995); Mullauer et al. *Mutat. Res*, 488, 211-231 (2001).

For example, as reported herein, cells in which LeuCAG3'tsRNA is depleted undergo apoptosis by an unusual mechanism that involves tsRNA-mediated depletion of 40S ribosomal subunits. Thus, methods of regulating tsRNAs can be used to regulate apoptosis and control disease.

BRIEF SUMMARY OF THE INVENTION

In various embodiments, the present invention provides an oligonucleotide that is complementary to a tRNA-derived small RNA (tsRNA) comprising at least one locked nucleic acid. In an embodiment, the oligonucleotide is of a structure according to Formula (I).

$$(A)_x\text{-}(B)_y\text{-}(C)_z \qquad \text{Formula (I)}$$

wherein x, y, and z are integers that are greater than or equal to 1, A is a locked or unmodified nucleic acid. When x is greater than 1, each A is independently selected and A is the 5' end of the oligonucleotide. When B is a locked or unmodified nucleic acid and y is greater than 1, each B is independently selected. When C is a locked or unmodified nucleic acid and z is greater than 1, each C is independently selected and C is the 3' end of the oligonucleotide. In an exemplary embodiment, A and C are locked nucleic acids, and B is one or more unmodified nucleic acids.

In an exemplary embodiment, the oligonucleotide is selected from the group consisting of: (a) tGTcAGgAgTgg-GaT (SEQ ID NO: 2); and (b) GGTGtcaggagtggGATT (SEQ ID NO: 11), where the uppercase letters represent locked nucleic acids and lowercase letters represent unmodified nucleic acids. In an exemplary embodiment, the oligonucleotide is complementary to a tsRNA molecule or a 3' end of a mature tRNA molecule. In an exemplary embodiment, the oligonucleotide is complementary to a group selected from leucine-CAG tsRNA and leucine-CAG tRNA. In an exemplary embodiment, the oligonucleotide comprises a pharmaceutically acceptable carrier.

In various embodiments, the present invention provides a method of inhibiting viability of a cell, the method comprising administering to the cell an oligonucleotide of the present invention. An exemplary method comprises inhibiting the function of leucine-CAG tsRNA. In an exemplary embodiment, the method inhibits cell proliferation, induces apoptosis, or induces cellular necrosis. In an exemplary embodiment, the inhibiting induces apoptosis.

In various embodiments, the present invention provides a method comprising treating a disease in a subject, the method comprising administering to the subject an oligonucleotide of the present invention. In an embodiment, the disease is one or more of cancer, autoimmune disease, a non-malignant state, or an excessive vascular state. In an embodiment, the non-malignant state is a hyperplasia and the excessive vascular state is macular degeneration.

BRIEF DESCRIPTION OF THE DRAWINGS

FIGS. 2A illustrates target sequences of oligonucleotides comprising locked nucleic acids (LNA) against leuCAG mature tRNA. Actual oligonucleotides are complementary to target sequences. Bold and underlined characters are LNA and remaining characters represent DNA. Boxed characters are LNA mis-match of leu3tsRNA. FIG. 2B shows the target sequences of LNA-containing oligonucleotides. Actual oligonucleotides are complementary to target sequences. Table 6 provides the representative sequence identifiers. FIG. 2C shows inhibition of leuCAG3tsRNA by the leu3ts GAPmer oligonucleotide (SEQ ID NO: 11). Mature leu tRNA is used as loading control.

FIGS. 3A-3H show that the depletion of LeuCAG3'tsRNA impairs cell viability and illustrates inactivation of tsRNA by mixmer oligonucleotides. FIG. 3A shows the sequence and predicted structure of mature human LeuCAG tRNA. The underlined sequences are the target of each indicated LNA. Closed and open triangles indicate 5' end of LeuCAG3'tsRNA and 3'end of LeuCAG5'tsRNA, respectively. FIG. 3B shows the depletion of 3'tsRNA (CAGPM) from LeuCAG impairs HeLa and HCT-116 cell viability, whereas depletion of 3'tsRNA from AspGTC (As- pPM), SerGCT (SerPM), MetCAT tRNA (MetiPM) does not. To determine cell viability, 3 days post-transfection, colorimetric cell proliferation assay (MTS assay) was performed. X-axis is transfected LNA and y-axis is the relative MTS value normalized to the MTS value from GL2 transfection as a control. FIG. 3C shows that LNA directed against the 3'tsRNA does not affect mature tRNAs. LNA directed against the anticodon loop (CAGcodon) or 5'end (CAGS'tsPM) of LeuCAG tRNA as well as LeuCAG3'tsRNA with different 2nt mismatches (CAGMM or CAGMM2) does not affect HeLa and HCT-116 cell viability. Cell viability was determined as in FIG. 3B. FIG. 3D shows the specific down-regulation of tsRNA by mixmer LNA oligonucleotides. Specifically, FIG. 3D illustrates the down regulation of leuCAG3tsRNA by leu3ts15PM (CAGPM) (SEQ ID NO: 2). LNA knockdown of LeuCAG3'tsRNA occurs in a sequence specific manner. After transfection of indicated LNA for 24 hrs, total RNA was subjected to northern blotting. LeuCAG3'tsRNA is bound to CAGPM and is not detected by the probe. U6 snRNA is the loading control. FIG. 3E shows gapmer LNAs, which induce RNase H activity, sequence specifically cleaves LeuCAG3'tsRNA, whereas the mature tRNA is not cleaved. After transfection of indicated gapmer LNAs for 24 hrs, northern hybridization was done as in FIG. 3D. FIG. 3F shows that depletion of LeuCAG3'tsRNA decreased the number of viable HeLa cells. Day post-The cell number normalized to day zero versus day post transfection. The normalized value at day 0 was set at 100. FIG. 3G shows that single stranded LeuCAG3'ts 18bp and 21bp rescues the LNA-induced decrease in cell viability. LNAs (GL2 (black bar) or CAGPM (grey bar)) and indicated single-stranded tsRNA were separately transfected into HeLa cells for 72 hrs. X-axis is single-stranded tsRNA; y-axis is the relative MTS value normalized to the MTS value from each GL2 transfection as a control. Cell viability was determined as in FIG. 3B. Each experiment was performed in triplicate and repeated twice. *P<0.01 compared with GL2 transfected cells untreated; GL2, control LNA complementary to firefly luciferase gene from pGL2 vector (Elbashir et al., 2001); CAGPM, LNA complementary to LeuCAG3'tsRNA; CAGMM, LNA complementary to LeuCAG3'tsRNA with 2 nt mis-match; CAGMM2, LNA complementary to LeuCAG3'tsRNA with 2 nt mis-match (mis-match position is different from CAGMM); CAG5'tsPM, LNA complementary to LeuCAG5'tsRNA; CAGcodon, LNA complementary to LeuCAG tRNA anti-codon; AspPM, LNA complementary to 3' end of AspGTC tRNA; SerPM, LNA complementary to SerGCT tRNA; MetiPM, LNA complementary to MetCAT initiator tRNA; Gap_GL2, gapmer LNA complementary to firefly luciferase gene; Gap_5'tsPM, gapmer LNA complementary to LeuCAG5'tsRNA; Gap_codonPM, gapmer LNA complementary to LeuCAG tRNA codon; Gap_3'tsPM, gapmer LNA complementary to LeuCAG3'tsRNA. Error bars represent the standard deviation. FIG. 3H illustrates the specific down-regulation of tsRNA by mixmer LNA oligonucleotides, specifically the down regulation of serGCT3tsRNA by Ser15GCTPM oligonucleotide (SEQ ID NO: 7).

FIG. 4 illustrates that leu3ts15PM (CAGPM) does not function through canonical miRNA/RNAi pathway. The graph shows normalized Renilla luciferase activity. SCRinCodonN represents scramble sequences that are located 6 bp downstream from the ATG start codon of the Renilla luciferase gene. CAGinCodonN represents perfect complementary sequences located 6bp downstream from the ATG start codon of the Renilla luciferase gene. SCRin3UTR represents scramble sequences that are located in 3'UTR of Renilla luciferase gene. CAGin3UTR represents perfect complementary sequences of SEQ ID NO: 2 located in the 3'UTR of the Renilla luciferase gene. LNACAG15PM is SEQ ID NO:2.

FIG. 7 illustrates that inactivation of leuCAG3tsRNA by LNA mixmer impairs cell viability. A) Inactivation of leuGAC3tsRNA impairs HeLa cell viability. X axis is transfected LNA and y axis is normalized MTT value. B) Inactivation of leuCAG3tsRNA impairs HCT cell viability. X axis is transfected LNA and y axis is normalized MTT value. C and D) Inactivation of leuCAG3tsRNA impairs cell viability. X axis is transfected LNA and y axis is normalized MTT value.

FIGS. 8A and 8B illustrate the inactivation of leuCAG3tsRNA and the resulting apoptosis. FIG. 8A illustrates that inactivation of leuCAG3tsRNA by LNA mixmer impairs cell viability. X axis is the day at which the cell number was counted; Y axis is the relative cell number normalized by cell number at day 0. FIG. 8B illustrates the induction of apoptosis from leuCAG3tsRNA inactivation as shown by PARP cleavage. CAG15PM is SEQ ID NO: 2.

FIGS. 9A-9D show that the depletion of LeuCAG3'tsRNA induces apoptosis. FIGS. 9A and 9B show the depletion of LeuCAG3'tsRNA increased cell populations undergoing apoptosis. Apoptosis in HeLa cells was measured using Annexin V-FITC and PI (propidium iodide) staining every 24 h post-transfection. FIG. 9A shows a representative result of the apoptosis assay wherein the number in each gate represents the percentage of cells in the gate. Accordingly, FIG. 9A illustrates that inactivation of leuCAG3tsRNA induces apoptosis. FIG. 9B shows a representative graph of each cell population from FIG. 9A. Values are means +/−SD (n=3). GL is GL2c, MM is CAGMM1, PM is CAGPM from Table 6. FIG. 9B shows an average cell population of apoptosis assay done in triplicate. Healthy cells are stained with neither Annexin V nor PI (Q1), early apoptotic cells are stained with only Annexin V (Q4), late apoptotic cells are stained with both Annexin V and PI (Q3), and dead cells are stained with only PI (Q2). Annexin V and PI staining indicates that the HeLa cell population undergoing early apoptosis (Q4) and late apoptosis (Q3), increased in days following transfection of CAGPM. FIG. 9C shows that depletion of LeuCAG3'tsRNA causes DNA fragmentation, another apoptosis marker. TUNEL assay in HeLa cells was performed at 24 h post LNA transfection. DNase I is a positive control. Nuclei were stained with DAPI (blue). TUNEL positive cells are shown in red. Merge is a merged image of DAPI and TUNEL staining. FIG. 9D shows that depletion of LeuCAG3'tsRNA causes PARP protein. Total protein extracts from HeLa and HCT-116 cells were prepared 24 h post-transfection, separated on 4-12% SDS PAGE and analyzed with indicated antibodies. The closed triangle indicates 116 kDa PARP protein, the open triangle indicates 89 kDa cleaved PARP protein. GAPDH is the loading control.

FIGS. 10A and 10B illustrate TUNEL assays 24 and 48 hours post transfection. FIGS. 10A and 10B present three columns (column from left to right: DIC, DAPI and TUNEL). The term "GL2c" refers to control LNA targeting a sequence not represented in HCT116 cells. The term "leu3ts-MM" (CAGMM1) refers to LNA bearing two mismatches with LNA3ts-PM. The term "LNA3ts-PM" (CAGPM) refers to LNA with complementary sequence of leutsRNA. The term "DNase I" refers to the positive control.

FIG. 11 illustrates cell cycle analysis of BrdU against propidium iodide staining. The bottom portion illustrates cell cycle analysis using flow cytometry showing that the G1 phase is accumulated in HCT cells after inactivation of leuCAG3tsRNA. The top portion illustrates a representative graph of each cell population. PM is CAGPM as listed in Table 6.

FIGS. 12A and 12B illustrate that global protein synthesis is not repressed by inactivation of leuCAG3tsRNA in HeLa or HCT116 cells 16 hours post transfection. Untreated represents untreated cells and mock represents cells treated with lipofectamine alone. 15 MM is CAGMM1; 15PM is CAGPM as listed in Table 6. FIG. 12A shows images of HeLa cells. FIG. 12B shows images of HCT116 cells.

FIGS. 13A-13C show that depletion of LeuCAG3'tsRNA does not affect global protein synthesis and the function of mature LeuCAG tRNA. FIG. 13A shows a global protein synthesis assay using Click-iT® AHA Alexa Fluor® 488 assay in HeLa cells was performed 24 h post-transfection of indicated LNA. The nucleus was stained with DAPI, blue color. Protein synthesis was measured with Click-iT® AHA, green color. Merge represents the merged image with DAPI and Click-iT® AHA. Un, untreated cells; mock, transfection of Lipofectamine 2000 without LNA; CHX, cycloheximide-treated positive control. Each used LNA is described in FIG. 3. FIG. 13A shows that global protein synthesis is not repressed by inactivation of leuCAG3tsRNA (PM is CAGPM as listed in Table 6). FIG. 13B shows a lobal protein synthesis assay using [35S]-methionine metabolic labeling in HeLa cells. 24 h post-transfection. HeLa cells were grown in media including [35S]-methionine for 10 minutes. Cells were lysed and equal amount of proteins were resolved on 4-12% SDS PAGE, stained with Coomassie brilliant blue (left) as a loading control; gels were scanned to measure incorporated radioactivity (right) showing the newly synthesized protein. Each cell number multiplied by $10^5$ represents the number of cell plated on 6 well culture dish at 24 hrs prior to transfection. Error bars represent the standard deviation. FIG. 13C shows that depletion of LeuCAG3'tsRNA does not affect the ability of mature LeuCAG tRNA to decode the CUG codon (mRNA) to Leucine (amino acid). Luciferase assay was done 24 h after co-transfection of indicated LNA and luciferase plasmid. CUG plasmid has unmodified Renilla and firefly luciferase gene. The CUC plasmid contains the unmodified Renilla and codon-modified firefly gene where all eleven CUG codons were replaced with CUC codons. Renilla luciferase activity was normalized to firefly luciferase activity expressed from the same plasmid, and was normalized to Renilla/firefly activity from the GL2 control transfections. Each value is a mean of three transfections. X-axis is transfected LNA; y-axis is normalized Renilla luciferase activity. Error bars represent the standard deviation.

FIGS. 14A and 14B illustrate codon modification of luciferase assay in HeLa and HCT116 cells. FIG. 14A shows data from HeLa cells. FIG. 14B shows data from HCT116 cells. Mock represents cells treated with lipofectamine alone. Original (left bar of each set) represents original psiCHECK2 dual-luciferase construct. Modified (right bar of each set) represents psiCHECK2 construct with leucine codon CAG switched to AAG or GAG.

FIGS. 15A-15C show that LeuCAG3'tsRNA does not have trans-gene silencing activity. FIG. 15A shows that LeuCAG3'tsRNA does not repress luciferase gene expression containing two copies of perfect complementary target sites in its 3'UTR or 5'UTR of firefly gene from pGL3 plasmid. A luciferase assay was performed 24h after co-transfection of either LNA GL2 or CAGPM, indicated firefly luciferase plasmid (pGL3), and *Renilla* luciferase plasmid (pRL). Each value from firefly luciferase plasmid was first normalized to the *Renilla* luciferase value from the co-transfected *Renilla* luciferase plasmid, and was normalized to the normalized firefly/*Renilla* value from a scrambled control plasmid co-transfected with either GL2 or CAGPM LNA. Each value is a mean of three transfections. X-axis is the target sequence; y-axis is normalized firefly luciferase activity. Scramble, scrambled sequences in 3'UTR, a negative control; LeuCAG3'tsPM in 3'UTR, two copies of perfect complementary sequences of LeuCAG3'tsRNA in 3'UTR; LeuCAG3'tsPM in 5'UTR, two copies of perfect complementary sequences of LeuCAG3'tsRNA in 5'UTR; Let-7 PM is a positive control of luciferase assay, a perfect complementary sequences of Let-7 in 3'UTR of firefly gene whose luciferase activity is repressed by endogenous Let-7 in HeLa cells. Error bars represent the standard deviation. FIG. 15B shows that LeuCAG3'tsRNA does not affect global gene expression. Scatter plots comparing gene expression (loge (FPKM+1)) of two RNA-Seq datasets from samples 24 h after transfection of indicated LNA. Pearson correlation coefficient is indicated by an r on each plot. FIG. 15C shows a subset of 5'tsRNA and 3'tsRNA does not co-sediment with polysomal fractions and mRNA undergoing active translation. Cytoplasmic lysates from HeLa cells were treated with cycloheximide and separated by ultracentrifugation in 10-50% sucrose gradients. Total RNAs were extracted from each fraction, separated on denaturing 15% acrylamide gel, transferred to membrane, and northern hybridization was performed. Each northern was performed as a duplicate. Left upper graph is ribosomal profile detected at 254 nm UV showing sucrose gradient discriminate 40S subunit, 60S subunit, 80S ribosome, and polysomes across sucrose gradient. The open triangle in each northern blot indicates detected tsRNA.

FIGS. 16A-16E show that LeuCAG3'tsRNA is required for ribosome biogenesis. FIGS. 16A and 16B show that depletion of LeuCAG3'tsRNA decreases amount of 40S ribosomal subunits and 80S ribosomes. FIG. 16A shows that the polysome profile was analyzed 24 h post-transfection of indicated LNA. Cytoplasmic lysates from HeLa cells were treated with cycloheximide and separated in 10-50% sucrose gradients. FIG. 16B shows that HeLa cells were treated with 2 mM puromycin for 15 min on ice and 10 min at 37° C., and processed as in FIG. 16A. FIG. 16C shows that depletion of LeuCAG3tsRNA decreases steady-state levels of 18S rRNA. Northern hybridization was performed with total RNA from HeLa cells prepared at 24 h post-transfection. Each number on top of image represents the cell number plated on 6-well culture dish the day prior to transfection. FIG. 16D shows that pre-rRNA processing pathways in human cells. 45S primary transcript (pre-45S) is divided into 5' external transcribed spacers (5'ETS), mature 18S rRNA, internal transcribed spacer 1 (ITS1), mature 5.8S rRNA, internal transcribed spacer 2 (ITS2), mature 28S rRNA, and 3' external transcribed spacers (3'ETS). There are two alternative processing pathways. Depletion of LeuCAG3'tsRNA prohibits processing from the 30S intermediate to 21S intermediate form in pathway B. Arrowhead and number indicate cleavage sites. Adapted from (Choesmel et al., 2008; Hadjiolova et al., 1993). FIG. 16E shows that depletion of LeuCAG3'tsRNA suppressed removal of the 5'-external transcribed spacer (5'-ETS) during 18S biogenesis. Northern hybridization was performed with total RNA from HeLa cells prepared at 24 h after transfection of indicated LNA and siRNA. ITS1 probe detects 45S primary transcript and intermediate form of mature 18S rRNA including the 41S, 30S, 21S, and 18S-E intermediate forms. 5'ETS probe detects 45S primary transcript and 30S intermediate form of mature 18S rRNA. ITS2 probe detects 45S, and 12S and 28S intermediate form of mature 5.8S and 28S rRNA.

FIGS. 17A-17E show that depletion of LeuCAG3'tsRNA down-regulates RPS28 protein level without affecting its mRNA level, whose depletion causes apoptosis. FIG. 17A shows that depletion of LeuCAG3'tsRNA down-regulates RPS23 and RPS28 protein level. HeLa cells were transfected with indicated LNA for 24 h and protein levels were determined by immunoblotting. GAPDH is the loading control. The relative signal to each GL2 transfection is listed. FIG. 17B shows that depletion of LeuCAG3'tsRNA does not change nuclear-cytoplasmic subcellular localization of RPS6 and RPS28 proteins. HeLa cells were transfected with indicated LNA for 24h and each protein level was determined by immunoblotting. Histone3 and c-Myc proteins are localized to the nucleus. GAPDH and tubulin are found in the cytoplasm. Total, total extracts; C, cytoplasm; N, nucleus. FIG. 17C shows that decreased RPS28 protein level induces apoptosis. HeLa cells were transfected with indicated siRNA for 24 h and 89 kDa, cleaved PARP protein was determined by immunoblotting. FIG. 17D shows that depletion of LeuCAG3'tsRNA does not alter RPS28 mRNA levels. Real time PCR was performed with total RNA purified at 24 h after transfection of indicated LNA. Each mRNA level was normalized by GAPDH mRNA. FIG. 17E shows that RPS28 over-expression restores 18S ribosomal RNA processing. After co-transfection of indicated plasmid (GFP expression plasmid or RPS28 expression plasmid) and LNA with HCT-116 cell lines for 24 h, total RNA and protein were extracted. Northern hybridization was performed with ITS1 probe and 18S rRNA probe (left). Western blotting was performed (right). GFP expression plasmid is the control.

FIGS. 18A-18D show that the depletion of LeuCAG3'tsRNA suppresses RPS28 translation in elongation phase. FIG. 18A shows that depletion of LeuCAG3'tsRNA specifically alters distribution of RPS28 mRNA within the sucrose gradient. The polysome profile was analyzed 24 h post-transfection. Cytoplasmic lysates from HeLa cells were treated with cycloheximide and separated in 10-50% sucrose gradients. Total RNAs were extracted from each fraction, separated on denaturing 0.9% agarose gel, transferred and northern hybridization was performed. The indicated base pairs (bp) provided to the left of the labeled gene name indicates the size of the coding sequences. The polysome profile is the same as shown in 16A. Methylene blue staining picture (Top) indicates the fractions containing 40S, 60S, 80S, and polysome. FIG. 18B shows that relative distribution of mRNA populations of FIG. 18A across sucrose gradient. Amounts of mRNAs for each fraction were normalized using the sum of the mRNA across all fractions. X-axis is the fraction number; y-axis is % of mRNA abundance. FIG. 18C shows that Harringtonine treatment after depletion of LeuCAG3'tsRNA stalls RPS28 mRNA at the 80S monosome suggesting that RPS28 translation is suppressed during elongation phase. The polysome profile was analyzed 24 h after transfection of LNA followed by treatment of harringtonine. Lysate preparation, separation in sucrose gradient, and northern were processed as in FIG. 18A. FIG. 18D shows a model for apoptosis resulting from LeuCAG3'tsRNA. The removal of the tsRNA results in a slowing of RPS28 mRNA elongation. Partial loss of RPS28 protein inhibits ribosomal RNA maturation. As a result, fewer 40S ribosomal subunits are produced, inducing cellular apoptosis.

FIGS. 19A-19E show that depletion of LeuCAG3'tsRNA impairs cell viability. FIGS. 19A and 19B shows images that are representative scans of the plates after the MTT assay (FIGS. 3B and 3C) at 3 day post-transfection respectively. FIG. 19C shows that each LNA directed to 3'tsRNA portion of mature tRNA sequence specifically binds to their intended target. LeuCAG tRNA (Leu) is detected by a probe that was designed to detect the 3'tsRNA (3'tsRNA probe). The same is true for the SerGCT (Ser) and MetCAT (Meti). 5'tsRNA probes used to detect the 5'tsRNA (5'tsRNA probe). After transfection of the indicated LNA for 24 hrs, total RNA was resolved on 15% acrylamide gel, transferred onto membrane, and hybridized with the indicated $^{32}$P labeled oligonucleotide probe. U6 is a loading control. Based on the result in FIG. 19D, the LNA actually binds to denatured mature tRNA during RNA extraction, and not the highly structured tRNA inside cells. FIG. 19D shows that the LNA mixmer binds to mature tRNA during the extraction of total RNA. GL2 and CAGPM LNA were not transfected, instead, both of them (RNA+GL2 or RNA+CAGPM) were mixed during the extraction of total RNA from HeLa cells. Each RNA was detected as in FIG. 19C. FIG. 19E shows that LeuCAG3'tsRNA knockdown decreased viable HCT-116 cells number. The x-axis is the day at which the cell number was counted post-transfection; y-axis is the relative cell number normalized by cell number at day 0.

FIGS. 21A and 21B show that depletion of LeuCAG3'tsRNA induces apoptosis. FIG. 21A shows that the knockdown of LeuCAG3'tsRNA increased cell population undergoing apoptosis. Apoptosis in HCT-116 cells was measured using Annexin V-FITC and PI (propidium iodide) staining at 24 h post-transfection. Average cell population of triplicate apoptosis assays. FIG. 21B shows that the knockdown of LeuCAG3'tsRNA causes DNA fragmentation, one of the hallmark of apoptosis. A TUNEL assay in HCT-116 cells was performed at 24 h (left) or 48 h (right) post-transfection. DNase I is a positive control. The nucleus was stained with DAPI, blue color. Tunel positive cells are stained as red color. Merge is a merged image of DAPI and TUNEL staining.

FIGS. 22A and 22B show that LeuCAG3'tsRNA does not have trans-gene silencing activity. FIG. 22A shows that AspGTC3'tsRNA and SerGCT3'tsRNA do not repress luciferase gene expression containing two copies of perfect complementary target sites in its 3'UTR, respectively. A luciferase assay was performed as in FIG. 15A. X-axis, target sites in 3'UTR; y-axis, normalized luciferase activity as in FIG. 15A. FIG. 22B shows that LeuCAG3'tsRNA does not regulate PRDM10 gene expression through binding to 5'UTR of PRDM10 and 3'UTR of PRDM10. A luciferase assay was performed as in FIG. 15A. X-axis, target sites in 3'UTR; y-axis, normalized luciferase activity as in FIG. 15A.

FIGS. 23A and 23B show that LeuCAG3'tsRNA is required for ribosome biogenesis. FIG. 23A shows that the knockdown of LeuCAG5'tsRNA (5'end of LeuCAG tRNA), SerGCT3'tsRNA (3'end of SerGCT tRNA), and MetiCAT3'tsRNA (3'end of MetiCAT tRNA) does not change the ribosome/polysomal profiles. 24 h post-transfection cytoplasmic lysates from HeLa cells were treated with cycloheximide and separated in 10-50% sucrose gradients. The polysomal profile was analyzed as in FIG. 15C. FIG. 23B shows that the knockdown of LeuCAG3'tsRNA suppressed 5'-external transcribed spacer (5'-ETS) processing in 18S biogenesis. Northern hybridization was performed with total RNA from HCT-116 and 293T cells prepared at 24 h post-transfection, ITS1 probe detects 45S primary transcript and intermediate form of mature 18S rRNA including 41S, 30S, 21S, and 18S-E intermediate form. 5'ETS probe detects 45S primary transcript and 30S intermediate form of mature 18S rRNA.

FIGS. 24A-24C show that depletion of LeuCAG3'tsRNA down-regulates RPS28 protein level without affecting its mRNA level, whose depletion causes apoptosis. FIG. 24A shows a schematic picture of putative LeuCAG3'tsRNA and LNA CAGPM binding sites on 45S pre-rRNA. To identify the tsRNA binding sites in 45S pre-rRNA, the RNAhybrid program was used and analyzed with 18 bp, 20 bp, and 21 bp sequences from the 3'end of LeuCAG tRNA as a LeuCAG3'tsRNA, resulting in 5 putative binding sites that were positioned in the 5'ETS, 1 site in ITS1, 1 site in ITS2, 3 sites in 28S rRNA, and 1 site in 3'ETS. Putative LeuCAG3'tsRNA binding site is indicated as a black bar. Putative LNA CAGPM binding site is indicated as a red bar. FIG. 24B shows that LeuCAG3'tsRNA and LNA CAGPM does not bind to 45S pre-rRNA. To inhibit the interaction between LeuCAG3'tsRNA and 45S pre-rRNA, each designed LNA, based on the FIG. 24A result, was transfected with HeLa cells for 24 hrs and Northern hybridization was performed. The sequences of each LNA are listed in Table 1. FIG. 24C shows the normalized ribosomal RNA abundance of FIG. 17E. Since 21S and 18S-E pre-rRNA are processed from 30S pre-rRNA, the signal from the 21S and 18S-E pre-rRNA was normalized to the signal from each 30S pre-rRNA and was again normalized to each normalized value from the GL2-GFP control transfection. The signal from the mature 18S rRNA could not be directly compared to the precursors because a different probe was used.

FIGS. 25A and 25B show that depletion of LeuCAG3'tsRNA suppresses RPS28 translation in elongation phase. FIG. 25A shows that Harringtonine treatment stalls RPS28 and GAPDH mRNA at 80S complex. The polysomal profile was analyzed followed by treatment of harringtonine. Lysate preparation, separation in sucrose gradient, and northern blots were processed as in FIG. 18A. Harringtonine (−), only cycloximide treatment shows RPS28 mRNA sedimentation across the gradient. Harringtonine, Harringtonine treatment shows that it blocks the first peptidyl transfer and stalls mRNA at 80S complex. FIG. 25B shows the relative mRNA distrivution of FIG. 18C. Upper graph shows RPS28 mRNA distribution after treatment of indicated LNA with only cycloheximide (FIG. 18C, top). Bottom graph shows RPS28 mRNA distribution after treatment of indicated LNA and harringtonine (FIG. 18C, bottom). Amounts of mRNAs for each fraction were normalized using the sum of the mRNA across all fractions. X-axis is the fraction number; y-axis is % of mRNA abundance.

FIG. 26 is the list of significant differential gene expression from FIG. 15.

DETAILED DESCRIPTION OF THE INVENTION

Introduction

Figure 1:
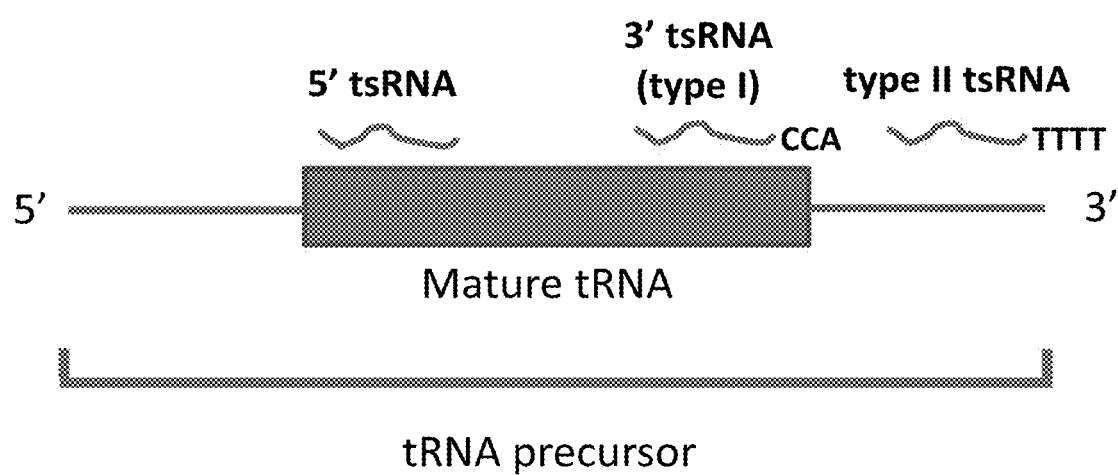
FIG. 1 provides an overview of tRNA-derived small RNAs.

In various embodiments, the invention described herein features compositions and methods that down regulate tRNA-derived small RNAs (tsRNAs). Accordingly, the present invention provides compositions and methods directed to oligonucleotides that are complementary to tsRNAs. In some embodiments, the tsRNA is leuCAG3tsRNA, which is derived from the mature leuCAG tRNA.

Surprisingly, the down regulation of tsRNAs, in particular leuCAG3tsRNA, by oligonucleotides of the present invention that employ different inhibitory mechanisms, results in the induction of apoptosis. The compositions and methods accordingly provide a new approach to causing cell death and offer new treatments for disease, for example, cancer, autoimmune disease, overgrowth of non-malignant states, and excessive vascular states.

Definitions

As used herein, "tRNA-derived small RNAs" or "tsRNA" or tsRNAs" refers to small RNAs that are derived from the cleavage of, and there "sense" to, a tRNA.

As used herein, "leuCAGtsRNA" refers to a tsRNA derived from leuCAG tRNA; "leuCAG3tsRNA" refers to a tsRNA derived from the 3' end of leuCAG tRNA, and "leuCAG5tsRNA" refers to a tsRNA derived from the 5' end of leuCAG tRNA.

As used herein, "tRNA" or "transfer RNA" refers to an RNA molecule that serves as the physical link between the nucleotide sequence of nucleic acids and the amino acid sequence of proteins.

As used herein, the term "target tsRNA" encompasses tsRNA derived from a tRNA molecule. The specific hybridization of an oligomeric compound with its target tsRNA interferes with the normal function of the tsRNA. This modulation of function of a tsRNA by compounds, which specifically hybridize to it, is generally referred to as "complementary" or "antisense."

As used herein, "oligonucleotide" refers to a single stranded nucleic acid molecule. An oligonucleotide can comprise ribonucleotides, deoxyribonucleotides, modified nucleotides (e.g. nucleotides with 2' modification, 3' modifications, synthetic base analogs, locked nucleic acids, etc.), or combinations thereof. Modified oligonucleotides are preferred in some embodiments over native forms having unmodified nucleotides because of properties including, for example, enhanced binding properties, increased stability in the presence of nucleases, and enhanced cellular uptake.

As used herein, "complementary oligonucleotides" or "antisense oligonucleotides" or "oligonucleotide that is complementary" refers to an RNA or DNA molecule that binds to another RNA or DNA (target RNA, DNA). For example, if it is an RNA oligonucleotide it binds to another RNA target by means of RNA-RNA interactions and alters the activity of the target RNA. A complementary oligonucleotide can upregulate or downregulate expression and/or function of a particular polynucleotide. The definition is meant to include any foreign RNA or DNA molecule which is useful from a therapeutic, diagnostic, or other viewpoint.

The term "nucleic acid" refers to deoxyribonucleotides or ribonucleotides and polymers thereof in either single- or double-stranded form, and complements thereof. The term refers to all forms of nucleic acids (e.g., gene, pre-mRNA, mRNA, tRNA) and their polymorphic variants, alleles, mutants, and interspecies homologs. The term nucleic acid is used interchangeably with gene, cDNA, mRNA, oligonucleotide, and polynucleotide. The term encompasses nucleic acids that are naturally occurring or recombinant. Nucleic acids can (1) code for an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N terminal end or the C-terminal end. Truncated versions of nucleic acid or polypeptide sequences can be naturally occurring or recombinantly created.

"Modified nucleic acids" can contain known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, locked nucleic acids (LNAs), and peptide-nucleic acids (PNAs). Modified bases include nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles. An unmodified nucleic acid as used herein refers to DNA.

As used herein, "locked nucleic acid" or "LNA" refers to a modified nucleotide where the ribose moiety is modified with an extra bridge connecting the 2' oxygen and 4' carbon. See, e.g. Koshkin et al. *Tetrahedron* 54:3607-30 (1998).

The term "identical" or "identity" or "percent identity," or "sequence identity" in the context of two or more nucleic acids or polypeptide sequences that correspond to each other refer to two or more sequences or subsequences that are the same or have a specified percentage of amino acid residues or nucleotides that are the same (e.g., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical" and are embraced by the term "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists for a specified entire sequence or a specified portion thereof or over a region of the sequence that is at least about 25 amino acids or nucleotides in length, or more preferably over a region that is 50-100 amino acids or nucleotides in length. A corresponding region is any region within the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted (e.g., by the local homology algorithm of Smith & Waterman, *Adv. AppL Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection, e.g., *Current Protocols in Molecular Biology* (Ausubel et al., eds. 1995 supplement)).

An exemplary algorithm suitable for determining percent sequence identity and sequence similarity are the BLAST and BLAST 2.0 algorithms, which are described in Altschul et al., *Nuc. Acids Res.* 25:3389-3402 (1977) and Altschul et al., *J Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

As used herein, "apoptosis" or "programmed cell death" is the physiological process for the killing and removal of unwanted cells and the mechanism whereby chemotherapeutic agents kill cancer cells. Apoptosis is characterized by distinctive morphological changes within cells that include condensation of nuclear chromatin, cell shrinkage, nuclear disintegration, plasma membrane blebbing, and the formation of membrane-bound apoptotic bodies (Wyllie et al., Int. Rev. Cytol., 68: 251, 1980). The translocation of phosphatidylserine from the inner face of the plasma membrane to the outer face coincides with chromatin condensation and is regarded as a cellular hallmark of apoptosis (Koopman, G. et al., Blood, 84:1415, 1994). The actual mechanism of apoptosis is known to be mediated by the activation of a family of cysteine proteases, known as caspases.

As used herein, "cell necrosis" or "necrosis" refers to a form of traumatic cell death that results from acute cellular injury.

As used herein "cell proliferation" refers to cellular growth.

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pincaloma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, gastric cancer, premalignant skin lesions, non-malignant states such as warts or nevi, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer. A nonmalignant state is a non-cancerous state also referred to as benign tumors. Nonmalignant tumors can grow but do not spread to other parts of the body.

As used herein, an "autoimmune disorder" refers to a disease or disorder that arises from an inappropriate immune response against antigens that are present and functionally normally within an organism. Non-limiting examples of autoimmune disorders are Addison's disease, Amyotrophic lateral sclerosis, Atopic allergy, Cushing's Syndrome, Diabetes mellitus type 1, Eczema, Endometriosis. Lupus erythematosus, multiple sclerosis, and rheumatoid arthritis.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate cancer biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis. Compounds can be inhibitors, activators, or modulators of a tsRNA, and are used to refer to activating, inhibitory, or modulating molecules identified using in vitro and in vivo assays of the tsRNA. Inhibitors are compounds that, e.g., bind to, partially or totally block activity, decrease, prevent, delay activation, inactivate, desensitize, or down regulate the activity or expression of a tsRNA, e.g., antagonists. Activators are compounds that increase, open, activate, facilitate, enhance activation, sensitize, agonize, or up regulate tsRNA activity, e.g., agonists.

As used herein, the term "pharmaceutically acceptable carrier" refers to various solvents as described herein which can be employed in the preparation of the formulations of the present invention.

As used herein, "patient" or "subject" refers broadly to any animal who is in need of treatment either to alleviate a disease state or to prevent the occurrence or reoccurrence of a disease state. Also, "Patient" as used herein, refers broadly to any animal who has risk factors, a history of disease, susceptibility, symptoms, signs, was previously diagnosed, is at risk for, or is a member of a patient population for a disease. The patient may be a clinical patient such as a human or a veterinary patient such as a companion, domesticated, livestock, exotic, or zoo animal. The term "subject" may be used interchangeably with the term "patient." In preferred embodiments, a patient is a human.

The term "treating" (or "treat" or "treatment") means slowing, interrupting, arresting, controlling, stopping, reducing, or reversing the progression or severity of a symptom, disorder, condition, or disease, but does not necessarily involve a total elimination of all disease-related symptoms, conditions, or disorders. The terms "treating," "treatment," and "therapy" as used herein refer to curative therapy, prophylactic therapy, and preventative therapy.

In certain embodiments, the therapy is designed to inhibit the development or progression of apoptotic diseases. The term "inhibit" means the ability to substantially antagonize, prohibit, prevent, restrain, slow, disrupt, eliminate, stop, reduce, or reverse the biological effects of leuCAGtsRNA.

The term "effective amount" refers to the amount or dose of a compound of the present invention which, upon single or multiple dose administration to a patient, provides the desired treatment or prevention. A therapeutically effective amount for any individual patient can be determined by the health care provider by monitoring the effect of the compound(s) on a biomarker, such as a cell cycle, inflammation, apoptotic, or cancer biomarker. Analysis of the data obtained by these methods permits modification of the treatment regimen during therapy so that optimal amounts of compound(s), whether employed alone or in combination with one another therapeutic agent, are administered, and so that the duration of treatment can be determined as well. In this way, the dosing/treatment regimen can be modified over the course of therapy so that the lowest amounts of compound(s) used alone or in combination that exhibit satisfactory tumor reducing effectiveness are administered, and so that administration of such compounds is continued only so long as is necessary to successfully treat the patient.

In certain embodiments, the therapy is designed to treat developmental defects (Xue and Barna, 2012), malignant processes (Bywater et al., 2013), Treacher Collins syndrome (TCS), Shwachman-Bodian-Diamond syndrome (SBDS), Dyskeratosis congenita, 5q⁻ syndrome, and Diamond Blackfan anemia (DBA) (reviewed in (Freed et al., 2010). In ceratin embodiments, the therapy is direct at diseases associated with and/or caused by apoptotic defects. In ceratin embodiments, the therapy is direct at diseases associated with and/or caused by ribosome biogenesis defects. In certain embodiments, the therapy is cancer therapy. In certain embodiments the therapy is used to treat an autoimmune disease, a non-maligant state, or an excessive vascular state. In certain embodiments, the therapy is used to treat hyperplasia or macular degeneration.

The term "tumor" refers to all neoplastic cell growth and proliferation, whether malignant or benign, and all precancerous and cancerous cells and tissues. The terms "cancer", "cancerous", and "tumor" are not mutually exclusive as used herein.

The terms "cancer" and "cancerous" refer to or describe the physiological condition in mammals that is typically characterized by aberrant cell growth/proliferation. Examples of cancers include, but are not limited to, carcinomas, lymphomas, blastomas, sarcomas, and leukemias. The terms "cancer" and "cancerous" further refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. "Mammal" for purposes of treatment refers to any animal classified as a mammal, including humans, domestic and farm animals, nonhuman primates, and zoo, sports, or pet animals, such as dogs, horses, cats, cows, etc.

In certain embodiments wherein the compound(s) of the invention are used in cancer therapy, they are used in combination with one or more additional anti-cancer agents. In certain embodiments, the anti-cancer agent is a chemotherapeutic agent.

A "chemotherapeutic agent" is a chemical compound useful in the treatment of conditions like cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin ($\gamma_1^I$ and calicheamicin $2^I_1$, see, e.g., Angew Chem Intl. Ed. Engl. 33:183-186 (1994); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In certain embodiments wherein the compound(s) of the invention are used in a therapy (e.g., cancer therapy, proliferative disease therapy, or anti-inflammatory therapy), they are used in combination with one or more additional anti-inflammatory agents. In certain embodiments, the anti-inflammatory agents are selected from a group comprising sufasalazine, mesalamine, NSAIDs, ImSAIDs, and corticosteroids.

In certain embodiments wherein the compound(s) of the invention are used in a therapy (e.g., cancer therapy, proliferative disease therapy, or anti-inflammatory therapy), they are used in combination with one or more additional antibiotic (i.e., antibacterial) agents.

tRNA-Derived Small RNAs

The present invention provides oligonucleotides complementary to tRNA-derived small RNAs (tsRNAs). A tsRNA can be any member of a non-coding regulatory RNA derived from tRNA. A tsRNA is thus usually "sense" to the tRNA from which it is derived. A tsRNA is usually 20-30 nucleotides in length, but can be shorter in length, e.g. 15 nucleotides, 10 nucleotides, or even 5 nucleotides or less. A tsRNAs can be longer in length, e.g. 35 nucleotides, 40 nucleotides, 45 nucleotides, or 50 or more nucleotides in length.

tsRNAs of the present invention can be referred to by any known phraseology used in the art. For example, tsRNAs can include tRNA halves, which are usually 28-36 nucleotides in length and are mainly generated by anticodon nucleases in bacteria (Ogawa et al. *Science* 283:2097-2100 (1999)), Rnylp in yeast (Thompson and Parker, *Cell* 138: 215-219 (2009), and angiogenin in humans (Fu et al. *FEBS Lett.* 583:437-442 (2009). tsRNAs of the present invention can also include tRNA fragments (tRFs), which are usually 14-22 nucleotides in length (Lee et al., *Genes. Dev.* 23 :2639-2649 (2009)). A tsRNA can be a 5'tsRNA, and 3' tsRNA (type I), or a tsRNA derived from the 3' end of a tRNA precursor.

Accordingly, tsRNAs can be any cleaved sequence of nucleotide derived from a tRNA. In an embodiment, the tsRNA can be any tsRNA derived from leuCAG tRNA, including but not limited to, leuCAG3tsRNA, leuCAG5tsRNA, and leuCAG3tsRNA. In other embodiments, the tsRNA is derived from aspGTC tRNA, serGCT tRNA, and metI tRNA.

A tsRNA can be derived from any organism, including but not limited to, *E. coli, T. thermophila, S. coelicor, A. fumigatus, S. cerevisiae, G. lamblia, T. cruzi, D. melanogaster, A. thaliana, C. maxima,* and any mammalian cell. A tsRNA can have any endogenous function as known in the art, including but not limited to, gene silencing; phage infection; reduction of uncharged tRNA; cell cycle progression; essential amino acid regulation; cell differentiation; conidiogenesis; down-regulation of protein synthesis; encystation; stress maintenance including oxidative stress, heat shock, UV hyperosmolarity, nutritional stress; and translational inhibition.

The tsRNAs of the present invention can be post-translationally modified either endogenously within a cell, or in vitro. Such modification can include any known post-translational modification, for example, methylation.

tsRNA Oligonucleotides

In an embodiment, oligonucleotides are provided against tsRNAs. The oligonucleotides can be complementary, antisense, or reverse-complementary to both a tsRNA derived from a tRNA, or the tRNA itself, which are terms known in the art. In an embodiment, the oligonucleotides are complementary to a tsRNA.

In some embodiments the oligonucleotide has a length of 7-25 (contiguous) nucleotides, such as 8, 9, 10, 11, 12, 13, 14, 15, 16, 17, 18, 19, 20, 21, 22, 23, or 24 (contiguous) nucleotides. In some embodiments, the oligonucleotide is fully complementary to a sub-sequence of contiguous nucleotides present in the tsRNA target. In some embodiments, the oligonucleotide comprises one or more mismatch with the complement of a sub-sequence of contiguous nucleotides present in said tsRNA target.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligonucleotide can have 1, 2, 3, 4, 5, or more mismatches. Thus, the oligonucleotides of the present invention can comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. As such, an oligonucleotide that is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the an. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., (1981) 2, 482-489). Methods of producing oligonucleotides are well known in the art, and can utilize, for example, an Expedite 8900/MOSS synthesizer (Multiple Oligonucleotide Synthesis System). LNA monomer building blocks and derivatives can be prepared by any method well known in the art, for example, as in WO 03/095467.

As such the oligonucleotide is an antisense oligonucleotide in that it is either fully complementary to the (corresponding) target sequence, or comprises one or more mismatches with the target sequence.

In some embodiments, the oligonucleotides are mixmers, which comprise both naturally occurring unmodified, and non-naturally occurring nucleotides (e.g. locked nucleic acids (LNAs)), where, as opposed to gapmers, tailmers, headmers and blockmers, there is no contiguous sequence of unmodified naturally occurring nucleotides, such as DNA units. As known in the art, mixmers effectively and specifically bind to their target, and the use of mixmers as therapeutic oligomers are considered to be particularly effective in decreasing the target RNA. In some embodiments the oligonucleotide can be a totalmer, which only comprise modified nucleotides. In some embodiments, the oligonucleotide can be a gapmer, which is a series of contiguous unmodified nucleic acids flanked on both sides by a series of contiguous nucleotides that are modified, such as with LNAs.

In some embodiments, the oligonucleotide binds to a target tsRNA and cleaves the target by RNAse mediated degradation. In some embodiments, the oligonucleotide binds to a target tsRNA and prevents the tsRNA from associating with any other molecule.

In some embodiments, the mixmer comprises or consists of a contiguous nucleotide sequence of repeating pattern of nucleotide analogue and naturally occurring nucleotides, or one type of modified nucleotide analogue and a second type of modified nucleotide analogues. The repeating pattern, may, for instance be every second or every third nucleotide is a nucleotide analogue, such as LNA, and the remaining nucleotides are naturally occurring nucleotides, such as DNA. It is recognized that the repeating pattern of nucleotide analogues, such as LNA units, may be combined with nucleotide analogues at fixed positions e.g. at the 5' or 3' termini.

The oligonucleotide of claim 1, wherein the oligonucleotide is of a structure according to Formula (I).

$(A)_x\text{-}(B)_y\text{-}(C)_z$  Formula (I)

In Structure 1, x, y, and z are integers that are greater than or equal to 1. A is a modified or unmodified nucleic acid. When x is greater than 1, each A is independently selected and A is the 5' end of the oligonucleotide. B is a modified or unmodified nucleic acid. When y is greater than 1, each B is independently selected. C is a modified or unmodified nucleic acid. When z is greater than 1, each C is independently selected and C is the 3' end of the oligonucleotide.

Accordingly, an embodiment of Structure 1 can include both mixmer and gapmer oligonucleotides. For example, when A is either a single modified nucleic acid, or A comprises two or more nucleic acids that are each a modified nucleic acid; and when B is either a single unmodified nucleic acid, or B comprises two or more nucleic acids that are each unmodified nucleic acids; and when C is either a single modified nucleic acid, or C comprises two or more nucleic acids that are each modified nucleic acids; then the oligonucleotide is a gapmer. In contrast, when each A is independently selected as either a modified or unmodified nucleic acid, when each B is independently selected as either a modified or unmodified nucleic acid, when each C is independently selected as either a modified or unmodified nucleic acid, and when at least one of A, B, or C comprises at least one modified and one unmodified nucleic acid, then the oligonucleotide is a mixmer.

In some embodiments, the first 5' nucleotide of the oligonucleotide is modified, for example, is LNA. In some embodiments, the first four nucleotides of the oligonucleotide are modified, for example, are LNA. In some embodiments, the last nucleotide of the oligonucleotide is modified, for example, is LNA. In some embodiments, the last four nucleotides of the oligonucleotides are modified, for example, are LNA. In some embodiments, a gapmer oligonucleotide has 10 unmodified nucleotides (e.g. is B of Structure 1). In some embodiments, the second, third, fifth, sixth, eighth, tenth, thirteenth, and fifteenth nucleotide from the 5' end of a 15 nucleotide mixmer oligonucleotide is modified, e.g. is LNA, and the first, fourth, seventh, ninth, eleventh, twelfth, and fourteenth nucleotide from the 5' end of a 15 nucleotide mixer oligonucleotide is unmodified, e.g., is DNA.

Exemplary oligonucleotides of the present invention are the mixmer oligonucleotide 5' tGTcAGgAgTggGaT 3' (SEQ ID NO: 2) and the gapmer oligonucleotide 5' GGTGtcag-gagtggGATT 3' (SEQ ID NO: 11) wherein uppercase letters represent a modified nucleic acid, e.g. LNA, and lowercase letters represent unmodified nucleic acids, e.g. DNA. Additional oligonucleotides that are exemplary to the present invention are provided in Table 5 and Table 6.

In an embodiment, the modified nucleic acid can be any modified nucleic acid known in the art, which can include, but is not limited to, a 2'-O-alkyl-RNA unit, a 2'-OMe-RNA unit, a 2'-amino-DNA unit, a 2'-fluoro-DNA unit, a 2'-MOE-RNA unit, a LNA unit, a PNA unit, a HNA unit, or an INA unit.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarily to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

Pharmaceutical Compositions

In various embodiments, a pharmaceutical formula comprises an oligonucleotide of the present invention in a pharmaceutically acceptable carrier. Appropriate pharmaceutically acceptable carriers are determined in part by the particular composition being administered (e.g., the oligonucleotides comprising modified nucleic acids as described herein), as well as by the particular method used to administer the composition. Accordingly, there are a wide variety of suitable formulations of pharmaceutical compositions of the present invention (see, e.g., Remington's Pharmaceutical Sciences, 17th ed., 1989).

Pharmaceutical formulations within the scope of the present invention can also contain other compounds, which can be biologically active or inactive. Pharmaceutical compositions can generally be used for prophylactic and therapeutic purposes.

Formulations suitable for oral administration can consist of (a) liquid solutions, such as an effective amount of the nucleic acid diluted in a diluent, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Formulations suitable for parenteral administration, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials. Methods for preparing such dosage forms are understood by those skilled in the art (see, e.g., REMINGTON'S PHARMACEUTICAL SCIENCES, 18$^{th}$ Ed., Mack Publishing Co., Easton, Pa. (1990)).

Pharmaceutical compositions can also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention can be formulated as a lyophilizate. Compounds can also be encapsulated within liposomes using well known technology.

Injection solutions and suspensions can be prepared from sterile powders, granules, and tablets of the kind previously described. Cells transduced by nucleic acids for ex vivo therapy can also be administered intravenously or parenterally as described above.

Inducing Apoptosis

In various embodiments, the invention provides a method to induce apoptosis or necrosis via the specific down regulation of a tsRNA, e.g., leuCAG3tsRNA (FIGS. 8-10).

The compositions and methods accordingly provide a new approach to causing cell death and offer new treatments for diseases caused by abnormalities in the control of apoptosis, which can result in either a pathological increase in cell number (e.g. cancer) or a damaging loss of cells (e.g. degenerative diseases). As non-limiting examples, the methods and compositions of the present invention can be used to prevent or treat a subject having the following apoptosis-associated diseases and disorders. Exemplary disorders include neurological/neurodegenerative disorders (e.g., Alzheimer's, Parkinson's, Huntington's, Amyotrophic Lateral Sclerosis (Lou Gehrig's Disease), autoimmune disorders (e.g., rheumatoid arthritis, systemic lupus erythematosus (SLE), multiple sclerosis), Duchenne Muscular Dystrophy (DMD), motor neuron disorders, ischemia, heart ischemia, chronic heart failure, stroke, infantile spinal muscular atrophy, cardiac arrest, renal failure, atopic dermatitis, sepsis and septic shock, AIDS, hepatitis, glaucoma, diabetes (type 1 and type 2), asthma, retinitis pigmentosa, osteoporosis, xenograft rejection, and burn injury.

Once made, the compositions of the invention find use in inhibiting cell viability. In an embodiment, viability of a cell is inhibited by administering to the cell the oligonucleotides of the present invention. In an embodiment, inhibiting a tsRNA inhibits the viability of a cell. In an embodiment, inhibiting a tsRNA induces apoptosis. In an embodiment, inhibiting leuCAG3tsRNA induces the viability of a cell. In an embodiment, inhibiting leuCAG3tsRNA induces apoptosis.

In an embodiment, the viability of a cell is inhibited by administering to the cell an oligonucleotide as described herein. One of skill in the art would understand that the oligonucleotides described herein function as mixmers with modified nucleic acids such as LNA, as gapmers with modified nucleic acids such as LNA, or oligonucleotides with unmodified nucleic acids, such as DNA. Accordingly, one of skill in the art would understand that an oligonucleotide can inhibit its target by more than mode of action, e.g. by RNAase degradation wherein the oligonucleotide binds to a target tsRNA and cleaves the target; or by binding to a target tsRNA and preventing the tsRNA from associating with any other molecule.

In an embodiment, the viability of a cell is inhibited, or apoptosis is induced, by administering to a cell any compound or modulator of a tsRNA. In an embodiment, the viability of a cell inhibited, or apoptosis is induced, by administering to a cell any compound or modulator of leuCAG3tsRNA.

Modulation of a tsRNA such as leuCAG3tsRNA can be assessed using a variety of in vitro and in vivo assays, including cell-based models as described herein. Such assays can be used to test for inhibitors and activators of a tsRNA such as leuCAG3tsRNA.

Assays to identify compounds with tsRNA-modulating activity, such as leuCAG3tsRNA, can be performed in vitro. In an exemplary assay, the tsRNA is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the tsRNA.

A high throughput binding assay can be performed in which the tsRNA thereof is contacted with a potential modulator and incubated for a suitable amount of time. In one embodiment, the potential modulator is bound to a solid support, and the tsRNA is added. A wide variety of modulators can be used, as described below, including small organic molecules, peptides, antibodies, etc.

In an embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (e.g., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *I Amer. Chem. Soc.* 116:2661 (1994)), oligocarbamates (Cho et al., *Science* 261:1303 (1993)), and/or peptidyl phosphonates (Campbell et al., *I Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853), small organic molecule libraries (see, e.g., benzodiazepines, Baum C & E N, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., Chem-Star, Ltd, Moscow, RU, 3D Pharmaceuticals, Exton, Pa., Martek Biosciences, Columbia, Md., etc.).

Methods of Treatment

The compositions of the invention find use in methods of treatment. In an embodiment, the present invention provides methods of treating a disease in a subject. The oligonucleotide or pharmaceutical formula thereof, is typically administered to the subject in a therapeutically effective dose, which may for example be determined by a dose which is sufficient to down-regulate the target tsRNA, or activity thereof, to a significant level over the time period between successive administration dosages, such as a level which is a therapeutic benefit to the subject. In some embodiments, the target tsRNA, or activity thereof is down-regulated by at least 10%, such as at least 20%, at least 30%, at least 40%, at least 50%, at least 60%, at least 70% or at least 80% or at least 90% during the time period between successive administration dosages. In an embodiment, the method of treatment includes inhibiting the function of a tsRNA. In an embodiment, the tsRNA is leuCAG3tsRNA. The compositions can include any oligonucleotide described herein, including those with and without modified nucleic acids.

Administration of the compositions of the present invention with a suitable pharmaceutical excipient can be carried out via any accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. Administration can be targeted directly to pancreatic tissue, e.g., via injection.

The compositions of the invention may be administered repeatedly, e.g., at least 2, 3, 4, 5, 6, 7, 8, or more times, or the composition may be administered by continuous infusion. Suitable sites of administration include, but are not limited to, dermal, mucosal, bronchial, gastrointestinal, anal, vaginal, and ocular. The formulations may take the form of solid, semi-solid, lyophilized powder, or liquid dosage forms, such as, for example, tablets, pills, lozenges, capsules, powders, solutions, suspensions, emulsions, suppositories, retention enemas, creams, ointments, lotions, gels, aerosols, or the like, preferably in unit dosage forms suitable for simple administration of precise dosages.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient. In some embodiments, the dosage of the compound administered at each dosing, such as unit dose, is within the range of about 0.01 mg/kg to about 25 mg/kg. In some embodiments, the dosage, such as unit dose, of the compound administered at each dosing is within the range of about 0.05 mg/kg to about 20 mg/kg. In some embodiments, the dosage (such as unit dose) of the compound administered at each dosing is within the range of about 0.1 mg/kg to about 15 mg/kg. In some embodiments, the (such as unit dose) dosage of compound administered at each dosing is within the range of about 1 mg/kg to about 15 mg/kg. In some embodiments, the dosage of the compound administered at each dosing is within the range of about 1 mg/kg to about 10 mg/kg. In some embodiments, the dosage (such as unit dose) of the compound administered at each dosing is within the range of about 0.01 mg/kg to about 25 mg/kg, such as about 0.01, 0.05, 0.1, 0.2, 0.3, 0.4, 0.5, 0.6, 0.7, 0.8, 0.9, 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12, 12.25, 12.5, 12.75, 13, 13.25, 13.5, 13.75, 14, 14.25, 14.5, 14.75, 15, 16, 17, 18, 19, 20, 21, 22, 23, 24 or such as about 25 mg/kg, each of which are individual embodiments.

In another approach to treatment, modified and unmodified nucleic acids can be used for transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acids, under the control of a promoter, then express a polypeptide of the present invention, thereby mitigating the effects of a disease associated with reduced insulin production.

Embodiments of the present invention can be used to treat sarcomas and carcinomas including, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pincaloma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, gastric cancer, premalignant skin lesions, non-malignant states such as warts or nevi, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

Embodiments of the present invention can be used to treat diseases associated with mis-regulation of apoptosis including, but not limited to neurological/neurodegenerative disorders (e.g., Alzheimer's, Parkinson's, Huntington's, Amyotrophic Lateral Sclerosis (Lou Gehrig's Disease), autoimmune disorders (e.g., rheumatoid arthritis, systemic lupus erythematosus (SLE), multiple sclerosis), Duchenne Muscular Dystrophy (DMD), motor neuron disorders, ischemia, heart ischemia, chronic heart failure, stroke, infantile spinal muscular atrophy, cardiac arrest, renal failure, atopic dermatitis, sepsis and septic shock, AIDS, hepatitis, glaucoma, diabetes (type 1 and type 2), asthma, retinitis pigmentosa, osteoporosis, xenograft rejection, and burn injury.

The methods and compositions of the present invention have use as gene therapy treatments. The ability to express artificial genes in humans facilitates the prevention and/or cure of many important human diseases, including many diseases which are not amenable to treatment by other therapies (for a review of gene therapy procedures, see Anderson, *Science,* 256:808-813 (1992); Nabel et al., *TIBTECH,* 11:211-217 (1993); Mitani et al., *TIBTECH,* 11:162-166 (1993); Mulligan, *Science,* 926-932 (1993); Dillon, *TIBTECH,* 11:167-175 (1993); Miller, *Nature,* 357: 455-460 (1992); Van Brunt, *Biotechnology,* 6(10):1149-1154 (1998); Vigne, *Restorative Neurology and Neuroscience,* 8:35-36 (1995); Kremer et al., *British Medical Bulletin,* 51(1):31-44 (1995); Haddada et al., in *Current Topics in Microbiology and Immunology* (Doerfler & Bohm eds., 1995); and Yu et al., *Gene Therapy,* 1:13-26 (1994)).

For delivery of nucleic acids, including oligonucleotides comprising modified nucleic acids such as locked nucleic acids, or oligonucleotides comprising only unmodified nucleic acids, viral vectors may be used. Suitable vectors include, for example, herpes simplex virus vectors as described in Lilley etal., *Curr. Gene Ther* 1(4):339-58 (2001), alphavirus DNA and particle replicons as described in e.g., Polo et al., *Dev. Biol.* (Basel), 104:181-5 (2000), Epstein-Barr virus (EBV)-based plasmid vectors as described in, e.g., Mazda, *Curr. Gene Ther.,* 2(3):379-92 (2002), EBV replicon vector systems as described in e.g., Otomo et al., *J. Gene Med.,* 3(4):345-52 (2001), adeno-virus associated viruses from rhesus monkeys as described in e.g., Gao et al., *PNAS USA.,* 99(18):11854 (2002), adenoviral and adeno-associated viral vectors as described in, e.g., Nicklin et al., *Curr. Gene Ther* 2(3):273-93 (2002). Other suitable adeno-associated virus (AAV) vector systems can be readily constructed using techniques well known in the art (see, e.g., U.S. Pat. Nos. 5,173,414 and 5,139,941; PCT Publication Nos. WO 92/01070 and WO 93/03769; Lebkowski et al., *Mol. Cell. Biol.,* 8:3988-3996 (1988); Vincent et al. (1990) Vaccines 90 (Cold Spring Harbor Laboratory Press); Carter, *Current Opinion in Biotechnology* 3:533-539 (1992); Muzyczka, *Current Topics in Microbiol. and Immunol.,* 158:97-129 (1992); Kotin, *Human Gene Therapy,* 5:793-801 (1994); Shelling etal., *Gene Therapy,* 1:165-169 (1994); and Zhou et al., *J. Exp. Med.,* 179:1867-1875 (1994)). Additional suitable vectors include E1B gene-attenuated replicating adenoviruses described in, e.g., Kim et al., *Cancer Gene Ther* 9(9):725-36 (2002) and nonreplicating adenovirus vectors described in e.g., Pascual et al., *J. Immunol.,* 160(9):4465-72 (1998). Exemplary vectors can be constructed as disclosed by Okayama et al., *Mol. Cell. Biol.,* 3:280 (1983).

Molecular conjugate vectors, such as the adenovirus chimeric vectors described in Michael et al., *J. Biol. Chem.,* 268:6866-6869 (1993) and Wagner et al., *Proc. Natl. Acad. Sci.* USA, 89:6099-6103 (1992), can also be used for gene delivery according to the methods of the invention.

Retroviruses can provide a convenient and effective platform for gene delivery systems. Retroviruses can be used to express the oligonucleotides of the present invention, including oligonucleotides comprising modified nucleic acids such as locked nucleic acids, or oligonucleotides comprising only unmodified nucleic acids. A selected nucleotide sequence encoding a polypeptide of the invention is inserted into a vector and packaged in retroviral particles using techniques known in the art. The recombinant virus can then be isolated and delivered to a subject. Suitable vectors include lentiviral vectors as described in e.g., Scherr et al., *Curr. Gene Ther.,* 2(1):45-55 (2002). Additional illustrative retroviral systems have been described (e.g., U.S. Pat. No. 5,219,740; Miller et al., *BioTechniques,* 7:980-990

(1989); Miller, *Human Gene Therapy*, 1:5-14 (1990); Scarpa et al., *Virology*, 180:849-852 (1991); Burns et al., *Proc. Natl. Acad. Sci. USA*, 90:8033-8037 (1993); and Boris-Lawrie et al., *Curr. Opin. Genet. Develop.*, 3:102-109 (1993)).

Other known viral-based delivery systems are described in, e.g., Fisher-Hoch et al., *Proc. Natl. Acad. Sci. USA*, 86:317-321 (1989); Flexner et al., *Ann. N.Y. Acad. Sci.*, 569:86-103 (1989); Flexner et al., *Vaccine*, 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques*, 6:616-627 (1988); Rosenfeld et al., *Science*, 252:431-434 (1991); Kolls et al., *Proc. Natl. Acad. Sci. USA*, 91:215-219 (1994); Kass-Eisler et al., *Proc. Natl. Acad. Sci. USA*, 90:11498-11502 (1993); Guzman et al., *Circulation*, 88:2838-2848 (1993); Guzman et al., *Cir. Res.*, 73:1202-1207 (1993); and Lotze et al., *Cancer Gene Ther.*, 9(8):692-9 (2002).

EXAMPLES

The methods system herein described are further illustrated in the following examples, which are provided by way of illustration and are not intended to be limiting.

Cell culture and transfection: Hela, HCT-116, and HEK293T cells were grown in Dulbecco's modified Eagle's medium (DMEM; GIBCO-BRL®) with 2 mM of L-glutamine, and 10% heat-inactivated fetal bovine serum with antibiotics. All transfection assays were done with Lipofectamine 2000 (Invitrogen®) according to the manufacturer's protocol. Locked nucleic acids (LNA) oligos were synthesized by Exiqon, which are listed on Table 1. 2'-o-methylated single strand RNAs were synthesized by IDT® (Integrated DNA Technologies), which are listed on Table 1. The siRNAs were purchased from Dharmacon® or Life Technologies®.

TABLE 1

The list of Locked nucleic acid (LNA) and 2'O-methylated single stranded RNA, Related to FIG. 3 and 24. LNA bases are upper-case letter and DNA bases are lower-case letter. All bases of 2'O-methylated single stranded RNA are 2'-o-methylated.

| LNA | Sequences |
| --- | --- |
| GL2c | GtaCgCgGaaTaCTtC |
| CAGPM | tGTcAGgAgTggGaT |
| CAGMM | tCTcACgAgTggGaT |
| CAGMM2 | tGTcAAgAcTggGaT |
| CAG5'tsPM | gcTcgGcCaTCcTgA |
| CAGcodon | GaGacTgcGAccTGa |
| AspPM | CCCgtcggggaatcgaACC |
| SerPM | cgACgAGgAtGggAt |
| MetiPM | TagCaGAgGAtgGTt |
| GAP_GL2 | CGTAcgcggaatacTTCG |
| GAP_5'tsPM | GACCgctcggccatccTGAC |
| GAP_3'tsPM | GGTGtcaggagtggGATT |
| GAP_codonPM | GACTgcgacctgaacGCAG |
| r571 | +CG + CA + CC + CC + ACG + CC + TTC + CC |
| r1936 | C + C + CGA + CA + CG + CC + CG + C + AC + CA + C |
| r2075 | +AT + CC + C + AC + CG + CC + AC + AGA + C + AC |
| r2960a | +CC + AC + CC + CC + CG + AC + C + CG |
| r2960b | +CC + CC + AC + CC + CC + CG + AC + CCG + G |
| r5823a | C + CG + CG + CC + CG + CCG + A + CA |
| r5823b | +CG + CC + CG + CCG + AC + A + CC + C + AC + GT |
| r6162 | +AC + C + AC + CG + CCC + C + CG + AC |
| r8527 | +CC + CA + CC + CC + CG + CA + CC + C |
| r8546 | +CCG + A + CC + CC + AC + CC + C + CG |
| r9079 | +CG + CC + CCG + CC + CC + CCG + A + C |
| r12034 | +CG + CC + AG + A + AG + CG + AG + AG |
| r4143 | +GG + TC + GG + GA + GT + GG + GT |

TABLE 1-continued

The list of Locked nucleic acid (LNA) and 2'O-methylated single stranded RNA, Related to FIG. 3 and 24. LNA bases are upper-case letter and DNA bases are lower-case letter. All bases of 2'O-methylated single stranded RNA are 2'-o-methylated.

| LNA | Sequences |
|---|---|
| 2'-o-methylated single strand RNA | |
| Control | UACGGACUUAAGCGGCUAC |
| LeuCAG3'ts18mer | AUCCCACUCCUGACACCA |
| LeuCAG3'ts21mer | UCGUAUCCCACUCCUGACACCA |
| LeuCAG3'ts26mer | GGGUUCGAAUCCCACUCCUGACACCA |

Dual-Luciferase Reporter Assay and cloning: 100 ng of pGL3 control reporter plasmids and 20 ng of pRL reporter plasmids was transfected with 60 nM of LNA into Hela or HCT-116 cells in 24 well plates. FF-luciferase and RL-luciferase activities were measured 24 hr after transfection by using Promega's dual-luciferase kit protocol and detected by a Modulus Microplate Luminometer (Turner BioSystems). Each complementary sequences of tested small RNAs were cloned into 3'UTR or 5'UTR of pGL3 control luciferase plasmid using XbaI and EcoRI or HindIII and NcoI enzymes respectively. All complementary sequences of tsRNA, Let-7, and control sequences were obtained from dimerization of each sense and anti-sense primers respectively, synthesized by IDT (Integrated DNA Technologies) (Table 2). PRDM10 5'UTR or 3'UTR was amplified from HeLa cell line cDNA and cloned into 5'UTR or 3'UTR of pGL3 control luciferase vector respectively (Table 3). The firefly gene, of which all CUG codons were replaced by CUC codons, from psicheck 2 luciferase vector was synthesized from Life Technologies. All required primers are listed on Table 3.

TABLE 3

| Oligonucleotide for Northern probe. | |
|---|---|
| SerGCT5'ts Northern probe | aACCACTCGGCCACCTCGTC |
| SerGCT3'ts Northern probe | CGACGAGGGTGGGATTCG |
| AspGTC3'ts Northern probe | CTCCCCGTCGGGGAATCG |
| leuCAG5'ts Northern probe | TAGACCGCTCGGCCATCCTGAC |
| leuCAG3'ts Northern probe | GTGTCAGGAGTGGGATTCG |
| MetCAT I 3'ts Northern probe | GTAGCAGAGGATGGTTTCGA |
| MetCAT e 3'ts Northern probe | GTGCCCCGTGTGAGGATCGA |

TABLE 2

DNA oligonucleotides for target sequences in luciferase vector, Related to the Experimental Procedures.

| scramble S (sense) | 5'-ACACGTCGACGTATATAGCTCATTCatgcatACACGTCGACGT ATATAGCTCATTC-3' |
|---|---|
| scramble AS (anti sense) | 5'-GAATGAGCTATATACGTCGACGTGTatgcatGAATGAGCTATA TACGTCGACGTGT-3' |
| LeuCAG3'tsPM S | 5'-TGGTGTCAGGAGTGGGATTCGAACCatgcatTGGTGTCAGGAG TGGGATTCGAACC-3' |
| LeuCAG3'tsPM AS | 5'-GGTTCGAATCCCACTCCTGACACCAatgcatGGTTCGAATCCC ACTCCTGACACCAT-3' |
| SerGCT3'tsPM S | 5'-TGGCGACGAGGATGGGATACGAACCCagtcTGGCGACGAGG ATGGGATACGAACCC-3' |
| SerGCT3'tsPM AS | 5'-GGGTTCGTATCCCATCCTCGTCGCCAgactGGGTTCGTATCCC ATCCTCGTCGCCA-3' |
| AspGTC3'tsPM S | 5'-TGGCTCCCCGTCGGGGAATCGAACCCagtcTGGCTCCCCGT CGGGGAATCGAACCCC-3' |
| AspGTC3'tsPM AS | 5'-GGGGTTCGATTCCCCGACGGGGAGCCAgactGGGGTTCGATT CCCCGACGGGGAGCCA-3' |
| Let-7PM S | 5'-CTAGAAACTATACAACCTACTTTTATAG-3' |
| Let-7PM AS | 5'-AATTCTGAGGTAGTAGGTTGTATAGTTT-3' |

TABLE 3-continued

Oligonucleotide for Northern probe.

| | |
|---|---|
| miR-15a Northern probe | acaaaccattatgtgctgcta |
| let-7 Northern probe | AACTATACAACCTACTACCTCA |
| miR-92a Northern probe | gACAGGCCGGGACAAGTGCAATA |
| 28S Northern probe | AACGATCAGAGTAGTGGTATTTCACC |
| 18S Northern probe | CGGAACTACGACGGTATCTG |
| ETS1 Northern probe | gagagcacgacgtcaccacatcgatcacgaagagc |
| 5'-ITS1 Northern probe | gcctcgccctccgggctccgttaatgatc |
| ITS2b Northern probe | gCTGCGAGGGAACCCCCAGCCGCGCA |

RNA isolation and northern blotting: Hela and HCT-116 cells in 6 cm dishes were transfected with each 60 nM of LNA. Total RNA was isolated at 24 h after transfection with TRIZOL reagent (Life Technologies®) according to the manufacturer's instructions. Total RNA was resolved by electrophoresis on 15% (w/v) polyacrylamide gel with 7 M urea for detection of small RNA whose size is smaller than 200 bp or on 0.9% agarose denaturing gel for detection of large RNA whose size is bigger than 200 bp. After transfer onto Hybond-N+ nylon membrane (Amersham). P32-labeled oligonucleotide or amplified cDNA probes were hybridized to the membrane in PerfectHyb™ Plus hybridization buffer (Sigma®). All oligonucleotides for northern probes are listed on Table 3. All oligonucleotides for cDNAs as northern probes are listed on Table 4.

TABLE 4

DNA oligonucleotides for PCR amplification, Related to the Experimental Procedures.

| | |
|---|---|
| PRDM10 5'UTR forward | atgca GAGCTC AACATAGCAAGGTAGATATCAC |
| PRDM10 5'UTR reverse | atgca GCTAGC TTTAAACAGCTCAGGCAGGCTG |
| PRDM10 3'UTR forward | atgcaGATATCcttccaccctggagcttgaatc |
| PRDM10 3'UTR reverse | atgcaCTGCAGgcttcacacatacaaacatg |
| NOP10_cDNA forward | at gtttctccag tattacctc |
| Nop10_cDNA reverse | tcagaggacagggcgcggttgc |
| RPS28_cDNA forward | gccgcc atggacacc agccgtgtgc |
| RPS28_cDNA reverse | tcagcgcaacctccgggcttc |
| RPS6_cDNA forward | atgcat gatatc atgaagctgaacatctccttc |

TABLE 4-continued

DNA oligonucleotides for PCR amplification, Related to the Experimental Procedures.

| | |
|---|---|
| RPS6_cDNA reverse | atgcat gaattc ttatttctgactggattcagac |
| RPS23_cDNA forward | atgcat gatatc atgggca agtgtcgtgg ac |
| RPS23_cDNA reverse | atgcat gaattc ttatgatcttggtctttccttc |
| RPS13_cDNA forward | TCGGCTTTACCCTATCGACG |
| RPS13_cDNA reverse | CAAACGGTGAATCCGGCTCT |

Measurement of cell proliferation: Cell proliferation was measured with CellTiter 96 nonradioactive cell proliferation assay kit (MTT assay; Promega®) according to the manufacturer's instructions. All experiments were performed in triplicates, from which average and standard deviation were calculated and plotted.

Apoptosis assay: The cell apoptosis assay was performed by measuring translocation of membrane phospholipid phosphatidylserine using an Annexin V-FITC apoptosis detection kit (BD Pharmingen®) according to the manufacturer's protocol. Cells were analyzed by FACScalibur instrument using FowJo software (Tree Star®). For the TUNEL assay, the apoptotic responses were identified 24 h post-transfection using Invitrogen's Click-iT® TUNEL Alexa Fluor® 594 Imaging Assay kit according to the manufacturer's protocol.

Western Blotting: 24 h post-transfection, cell lysates were prepared using 1× cell lysis buffer (Cell Signaling) with 1 mM PMSF (Cell Signaling®). 15 ug of protein lysate was run on 4-20% SDS PAGE and transferred to Hybond-P membrane (GE Healthcare®). The membrane was incubated for 20 min at room temperature (RT) in 4% BSA (Omnipur®) solution, washed, and incubated for over night (O/N) at 4° C. with one of the following antibodies. After washing and incubation for 1 hr at RT with secondary antibody, protein signal was detected using Pierce ECL2 substrate (Thermoscientific®) according to manufacturer's protocol. Antibodies for immunoblotting were as follows: anti-PARP rabbit monoclonal Ab (clone 46D11; Cell Signaling®), anti-cleaved PARP (Asp214) rabbit monoclonal Ab (clone D64E10; Cell Signaling®), anti-GAPDH-peroxidase mouse Ab (Sigma®), anti-RPS13 rabbit polyclonal Ab (Abnova®), anti-RPS7, 10, 16, 19, 24, and 28 Ab (Abcam®), RPL7, 13a, 26, and XRN2 Ab (Abcam®), anti-RPS6 mouse monoclonal Ab (Cell signal®).

High throughput large RNA sequencing: After transfection for 24 hrs, total RNA was isolated using TRIZOL reagent. Residual DNA contamination and ribosomal sequences were removed from total RNA using TURBO DNA-free™ Kit (Life technologies) and Rib o-Zero Gold™ kit (Epicentre) according to manufacturer's instructions respectively. A total of 150-200 ng of purified RNA was subjected to strand-specific RNAseq using the ScriptSeq v2 mRNA-SEQ library preparation kit (Epicentre), which uses a random-hexamer method of cDNA synthesis according to manufacturer's instructions. 50 bp paired-end reads were generated on an Illumina HiSeq 2000 machine yielding a total of between 18 and 40 million paired-end reads. Sequences were mapped to the human hg19 genome using TopHat version 1.4.1 with the following parameters: -r 180, -mate-std-dev 130 -library-type fr-secondstrand (Trapnell et al., 2009). FPKM values were calculated using the CuffDiff program version 1.3.0 (Trapnell et al., 2012; 2010) using refGene transcripts as an input file for comparison of gene expression levels.

Polysome gradient and RNA preparation: Polysome gradient and RNA preparation were performed as described previously (Fuchs et al., 2011) with modifications. After transfection for 24hrs, cells were treated with 100 jig/ml cycloheximide for 5 min, and cells were lysed in buffer containing 15 mM Tris-HCl (pH 7.5), 150 mM KCl, 5 mM MgCl2, 500 u/ml RNasin (Promega), 20 u/ml SUPERaseIn (Life Technologies) and 1% Triton X-100. For harringtonine treatment, after transfection for 24 hrs, cells were treated with 2 ug/ml harringtonine for 2 min, followed by treatment of 100 ug/ml cycloheximide for 5 min, and then lysed. The cleared lysates were loaded onto 10-50% sucrose gradients [15 mM Tris-HCl (pH 7.5), 150 mM KCl, 5 mM MgCl2, 20 u/ml SUPERaseIn (Life Technologies), and 100 jig/ml cycloheximide] with a 60% sucrose cushion. Gradients were centrifuged at 35,000 rpm at 4° C. for 2 hr 45 min and fractionated with a Teledyne Isco Foxy R1 Retriever/UA-6 detector system. The gradient fractions were sequentially treated for 30 min at 37° C. with 0.5 mg/ml proteinase K (New England Biolabs) in the presence of 5 mM EDTA. RNAs were extracted with an equal volume of phenol-chloroform-isoamylalcohol (25:24:1; Life Technologies). Aqueous phases were re-extracted with chloroform and precipitated with 3 M sodium acetate, 1 µl of 15 mg/ml glycogen (Life Technologies), 100% ethanol at −20° C. overnight, washed with 75% ethanol, and resuspended in DEPC-water.

Puromycin gradients: Puromycin gradients were performed as described previously (Fuchs et al., 2011) with modifications. After transfection for 24 hr, cells were lysed in buffer containing 15 mM Tris-HCl (pH 7.5), 500 mM KCl, 2 mM MgCl2, 2 mM puromycin, 500 u/ml RNasin (Promega), 20 u/ml SUPERaseIn (Life Technologies), and 1% Triton X-100. Following incubation on ice for 15 min, 80S ribosome subunits were separated at 37° C. for 10 min. Following centrifugation, cleared lysates were loaded onto 10-50% sucrose [500 mM KCl, 15 mM Tris-HCl (pH 7.5), 2 mM MgCl2, and 20 u/ml SUPERaseIn (Life Technologies)] with a 60% sucrose cushion. Gradients were centrifuged at 35,000 rpm at 4° C. for 2 hr 45 min. As control, cells were lysed and separated in gradients containing 15 mM Tris-HCl (pH 7.5), 500 mM KCl, 15 mM MgCl2, 20 u/ml SUPERaseIn (Life Technologies), 100 ug/ml cycloheximide. The lysis buffer also contained 1% Triton X-100.

Metabolic labeling of cell proteins with [$^{35}$S]-Methionine: After transfection of indicated LNA for 24 hrs, cells were washed twice with PBS and were grown in DMEM media without Cystine and Methionine (DMEM-Cys-Met) (Life Technologies) for 30 min at 37° C. The media was removed and DMEM-Cys-Met plus 100 uCi protein labeling mix (Perkin Elmer) was added for 10 min at 37° C. Cells were washed twice with cold PBS, harvested, and lysed with RIPA buffer. Equal amount of proteins were resolved on 4-12% SDS PAGE, stained with coomasie brilliant blue, the gel was dried and the incorporated radioactivity was scanned using PMI (Personal Molecular Imager).

Immunoprecipitation: Antibodies were incubated with protein A/G UltraLink Resin (Thermo Scientific) for o/n at 4° C. Cells were lysed with IP buffer (25 mM Tris pH7.5, 150 mM Kcl, 0.5% NP40, 0.02 mM EDTA) containing RNasin® plus (promega) and cOmplete Protease Inhibitor Cocktail Tablets (Roche) and incubated with prepared protein A/G conjugated Antibodies for 2 hrs at 4° C. All samples were washed with IP buffer 3 times. Immunoprecipitated RNAs were extracted using TRIZOL (Life Technologies) according to the manufacturer's protocol. Immunoprecipitated proteins were separated from protein A/G UltraLink resin by adding RIPA buffer and boiling for 5 min. Antibodies for immunoprecipitation were as follows: anti-Ago1 monoclonal Ab (clone 1F2; Wako), anti-Ago2 monoclonal Ab (clone 2D4; Wako), and anti-Ago3 monoclonal Ab (clone 1C12; Wako).

Example 1

GAPmer Antisense Oligonucleotides Inhibit leuCAG3tsRNA

GAPmer oligonucleotides were designed to comprise a series of 5' and 3' locked nucleic acids (LNAs) flanking a sequence of DNA nucleotides (Table 5). GAPmer oligonucleotides provided in Table 5 are complementary to the tRNA structure shown in FIGS. 2A and 2B.

TABLE 5

GAPmer oligonucleotides. Nucleotides with capital letters are LNA nucleotides and nucleotides with lowercase letters are DNA nucleotides.

| SEQ ID NO | name | complementary to | sequence |
|---|---|---|---|
| 9 | AspPM | AspGTC tRNA | CCCgtcggggaatcgaACC |
| 10 | GL2b | GL2b (fire fly luciferase) | TCGaagtattccgcgtACG |
| 11 | leu3ts | leuCAG3tsRNA | GGTGtcaggagtggGATT |
| 12 | leu5ts | leuCAG5tsRNA | GACCgctcggccatcCTGAC |
| 13 | leuA | leuCAGtsRNA | ACGCagcgccttagACCG |
| 14 | leuB | leuCAGtsRNA | GACTgcgacctgaacGCAG |
| 15 | leuC | leuCAGtsRNA | CGCCtccaggggagACTG |
| 16 | leuD | leuCAGtsRNA | GGGAttcgaacccacGCCT |
| 17 | leuD-6bp | leuCAGtsRNA | CGAAcccacgcctccAGGG |
| 18 | leuD-4bp | leuCAGtsRNA | TTCGaacccacgcctCCAG |
| 19 | leuD-2bp | leuCAGtsRNA | GATTcgaacccacgcCTCC |

Different GAPmer oligonucleotides were tested for the ability to inhibit leuCAGtsRNA. Total RNA was purified by Trizol at 48 hours after transfection into HeLa or 293 T cells using 10 nM of each GAPmer oligonucleotide shown in Table 5. 5 µg of total RNA was loaded on 15% denaturing gels and transferred to positively charged nylon membranes. The results demonstrate that the leu3ts GAPmer oligonucleotide effectively inhibits leuCAG3tsRNA (FIG. 2). The leu3ts GAPmer oligonucleotide bindings to leu3tsRNA and cleaves the target by RNAse H mediated degradation.

Example 2

MIXmer Antisense Oligonucleotides Inhibit leuCAG3tsRNA

Mixmer oligonucleotides were designed to comprise LNAs interdigitized with DNA nucleotides (Table 6). Mixmer oligonucleotides provided in Table 5 are complementary to the tRNA structure shown in FIG. 2A.

TABLE 6

MIXmer oligonucleotides. Nucleotides with capital letters are LNA nucleotides and nucleotides with lowercase letters are DNA nucleotides.

| SEQ ID NO | name | complementary | to sequence |
|---|---|---|---|
| 1 | GL2c | GL2 (fire fly luciferase) | GtaCgCgGaaTaCTtC |
| 2 | leu3ts15PM (CAGPM) | leuCAG3tsRNA | tGTcAGgAgTggGaT |
| 3 | leu3ts15MM1 (CAGMM1) | leuCAG3tsRNA with 2nt mismatch | tCTcACgAgTggGaT |
| 4 | leu3ts15MM2 (CAGMM2) | leu3CAG3tsRNA with 2nt mismatch | tGTcAAgAcTggGaT |
| 5 | leu5ts15PM (CAG5ts) | leuCAG5tsRNA | gcTcgGcCaTCcTgA |
| 6 | CAGcodon | leuCAG tRNA codon region | GaGacTgcGAccTGa |
| 7 | ser15GCTPM (SerPM) | SerGCT3tsRNA | cgACgAGgAtGggAt |
| 8 | meti15PM (MetiPM) | Meti3tsRNA | TagCaGAgGAtgGTt |

Different Mixmer oligonucleotides were tested for the ability to inhibit leuCAG3tsRNA. The Mixmer oligonucleotides shown in Table 6 were transfected at 60 nM into HeLa and HCT cells. Northern hybridization analysis was performed 24 hours later. 5 μg of total RNA was loaded on 15% denaturing gels and transferred to positively charged nylon membranes. U6snRNA was used as a loading control. The results demonstrate that the CAGPM oligonucleotide effectively inhibits leuCAG3tsRNA (FIG. 3). CAGPM binds leu3tsRNA and prevents the target RNA from functioning with other molecules (FIG. 3).

Example 3

Mode of Oligonucleotide Action Compared to Known Silencing Pathways

The MIXmer oligonucleotides shown to effectively inhibit leuCAG3tsRNA were tested for activity through known gene silencing pathways. A luciferase assay was performed at 24 hours after co-transfection of indicated luciferase construct and 60 nM of oligonucleotide. Each experiment was performed in triplicate. The graph shown in FIG. 4 show that the CAGPM oligonucleotide did not affect gene expression containing perfect complementary sites in its codon or 3'UTR of leuCAG3tsRNA.

Figure 5:
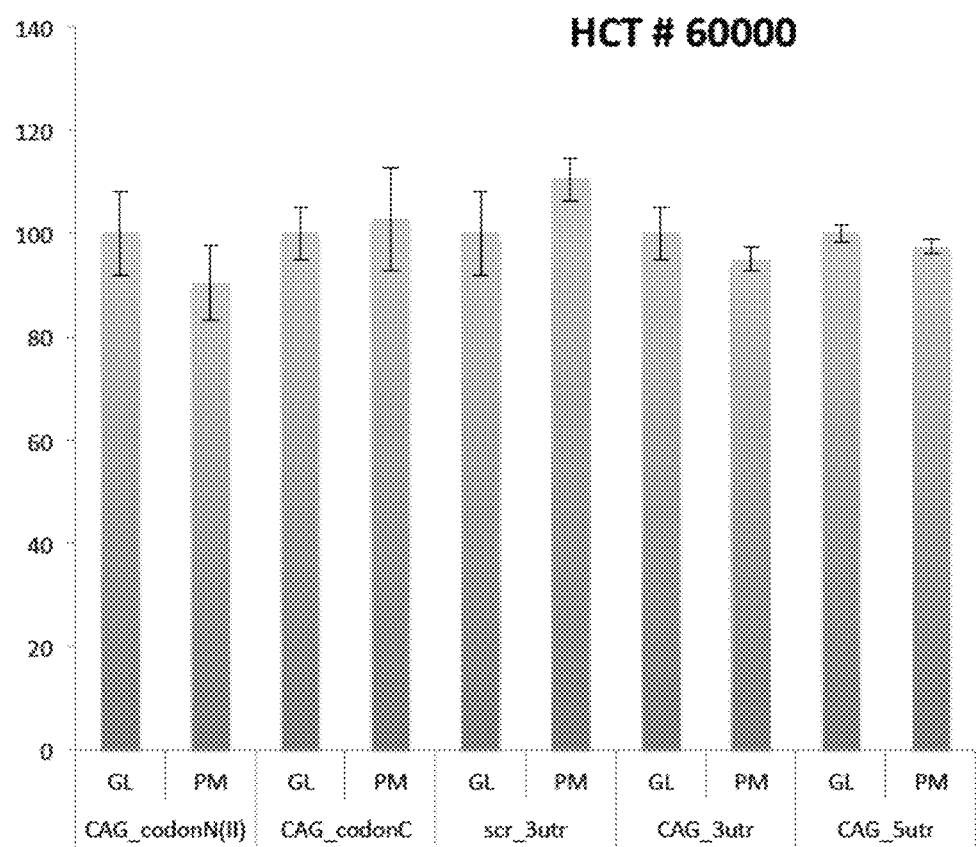
FIG. 5 illustrates that leuCAG3tsRNA does not have trans-gene silencing activity similar to microRNA. All constructs have 2 copies of perfect complementary sites of 18 bp of leuCAG3tsRNA. codon(II): leuCAG 3tsRNA binding sites in N-terminal codon; codonC: leuCAG 3tsRNA perfect complementary sites in C-terminal codon; scr_3utr: scramble sequence in 3utr; CAG_3utr: leuCAG 3tsRNA perfect complementary sites in 3'UTR; CAG_5utr: leuCAG 5tsRNA binding sites in 5'UTR
Figure 6:
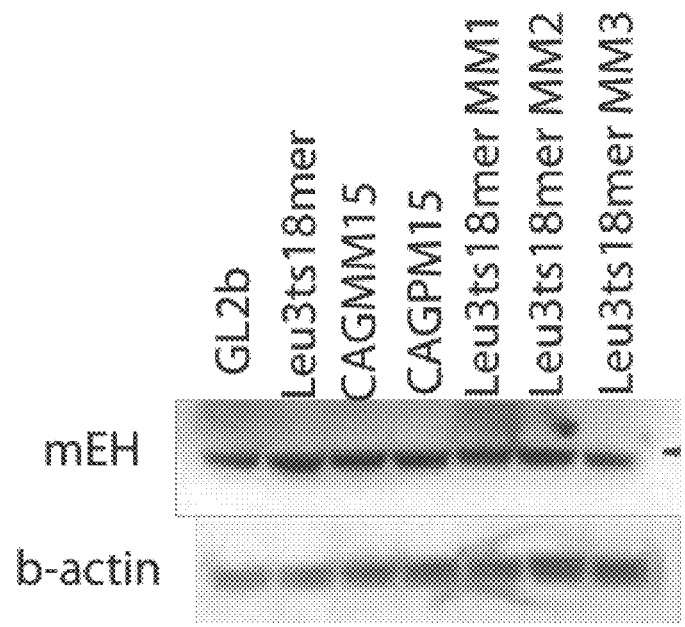
FIG. 6 illustrates that an LNA15bp mixmer does not affect endogenous genes with similar LNA target sequences.

LeuCAG3tsRNA was tested to determine if leuCAG3tsRNA has trans-gene silencing activity similar to known microRNA mechanisms. Luciferase assays were performed at 24 hours after co-transfection of indicated luciferase construct and 60 nM of oligonucleotide. The results show that leuCAG3tsRNA does not have trans-gene silencing activity similar to known microRNA mechanisms (FIG. 5). The graph in FIG. 5 shows the normalized Renilla luciferase activity. Each construct had two copies of perfect complementary sites of leuCAG3tsRNA or leuCAG5tsRNA.

LeuCAG3tsRNA was tested to determine whether endogenous genes with similar target sequences would be affected. The epoxide hydrolase gene has 1 mis-match complementary site in its open reading frame. After transfection of each 60 nM of indicated oligonucleotide, total extract was prepared after 24 hours and loaded on SDS PAGE gels. Immunoblot were performed with the indicated antibody. The results show that leuCAG3tsRNA did not affect endogenous genes with similar target sequences.

Example 4

Inactivation of leuCAGtsRNA Impairs Cell Viability

Cell proliferation was monitored using an MTT assay kit 72 hours after transfection of 60 nM of each antisense oligonucleotide in HeLa cells indicated in FIG. 7A. All experiments were performed in triplicate. The CAGPM oligonucleotide effectively impaired cell viability in HeLa cells.

Cell proliferation was monitored using an MTT assay kit 72 hours after transfection of 60 nM of each antisense oligonucleotide in HCT cells indicated in FIG. 7B. All experiments were performed in triplicate. The CAGPM oligonucleotide effectively impaired cell viability in HCT cells.

The CAGPM oligonucleotide specifically impaired cell viability among several different oligonucleotides. Cell proliferation was monitored using an MTT assay kit 72 hours after transfection of 60 nM of each antisense oligonucleotide in HCT cells indicated in FIGS. 7C and D. All experiments were performed in triplicate.

To validate the MTT assay results, cell numbers were counted after transfection of each oligonucleotide. After transfection of each 60 nM of indicated oligonucleotide, the cell number was counted using a hematocytometer at the day indicated. All experiments were performed in triplicate at results of validation shown in FIG. 8A.

Example 5

Inactivation of leuCAGtsRNA Induces Apoptosis

The effect of antisense oligonucleotides against leuCAGtsRNA on apoptosis was determined. Poly (ADP-ribose) polymerase (PARP) is a family of protein involved in DNA repair and apoptosis. A key initiation element of the apoptotic pathway is the activation of caspases followed by cleavage of caspase substrates. Detection of an 89 kDa or 24 kDa caspase cleavage fragment of PARP-1 by caspase 3 and 7 is a hallmark of apoptosis. The apoptotic markers PARP, Casp-3, 7, and 9 were measured following transfection of 60 nM of each indicated oligonucleotide. Protein extracts were prepared at each indicated day. The CAGPM oligonucleotide induces apoptosis as indicated by cleaved PARP, Caspase 7, and 9 (FIG. 8B).

Annexin V and propidium iodide (PI) was measured to determine apoptotic effects of different antisense oligonucleotides. Other morphological features of apoptosis include loss of plasma membrane asymmetry and attachment, condensation of the cytoplasm and nucleus, and internucleosomal cleavage of DNA. The membrane phospholipid phosphatidylserine (PS) is translocated from the inner to outer leaflet of the plasma membrane. Annexin V is a 35-36 kDa Ca2+ dependent phospholipid-binding protein that binds to cells with exposed PS. Viable cells with intact membranes exclude PI, whereas membranes of dead and damaged cells are permeable to PI.

Cells were stained with annexin V and PI at each day after transfection of 60 nM of indicated antisense oligonucleotide. Apoptosis was measured using flow cytometry. All experiments were performed in triplicate. FIG. 9 show that CAGPM induces apoptosis as determined by annexin V and PI staining.

Cells were stained with Brdu and PI at 24 hours after transfection of 60 nM of each indicated oligonucleotide and cell cycle analysis was performed using flow cytometry. The results shown in FIG. 11 show that the G1 phase is accumulated in HCT cells after inactivation of leuCAG3tsRNA by the CAGPM oligonucleotide.

TUNEL assays were performed to measure apoptotic cell death. Cells were grow in DMEM media with 100% FBS before treatment with 60 nM of the indicated oligonucleotides using lipofectamine transfection. The TUNEL assay was performed at 24 hours (FIG. 10A) and 48 hours (FIG. 10B) post-transfection. The results show that CAGPM induces apoptosis.

Example 6

Effect of Antisense Oligonucleotides on Global Translation

Figures 13, 13A:
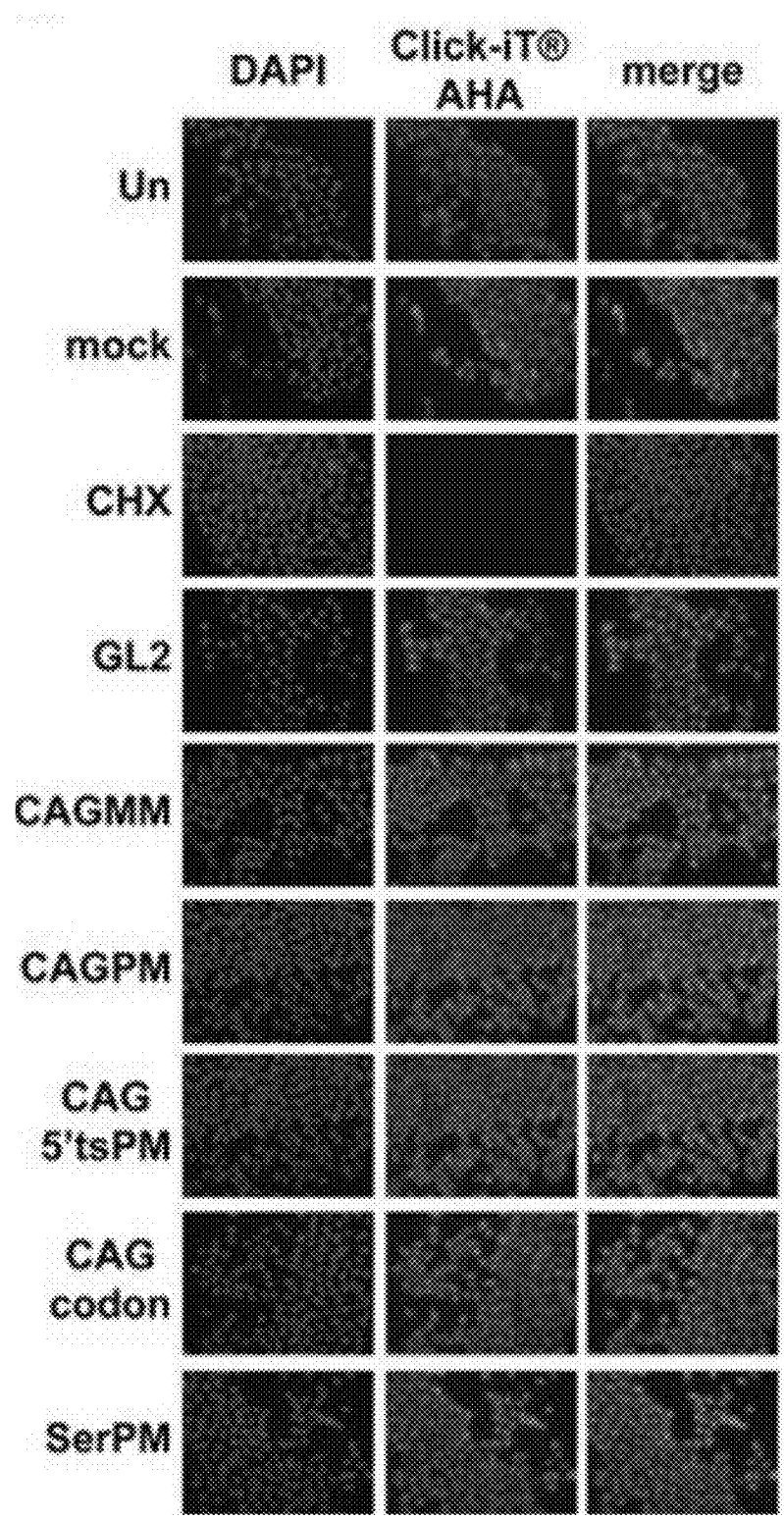

The effect of oligonucleotides against leuCAGtsRNA on global translation was determined. Different numbers of cells were grown in medium containing S35 methionine for 10 minutes at 24 hours after transfection of each 60 nM of indicated oligonucleotide, and protein extracts were prepared in RIPA buffer. 10 µg of protein extract for each oligonucleotide were run on an SDS PAGE gel, stained with coomassie blue, and exposed on a phosphor screen. The results show that global translation is not repressed by inactivation of leuCAG3tsRNA (FIG. 13).

Cells were also treated with cycloheximide to determine the effect of leuCAGtsRNA downregulation on global protein function. Cells were grown in DMEM with 10% FBS before lipofectamine transfection with indicated oligonucleotides, and protein synthesis assays were performed 16 hours after transfection and 30 minutes after cycloheximide treatment. FIG. 12A and FIG. 12B show that downregulation of leuCAG3tsRNA by CAGPM does not affect global translation in HeLa and HCT116 cells, respectively.

The effect of codon modification was determined to investigate production of proteins having specific codons. Luciferase constructs were designed to detect the effect of anti-leuCAG3tsRNA oligonucleotides on serCAG tRNA function. The leucine codon CTG on the Renilla gene was replaced by the alternative leucine codon CTT or CTC to avoid using leuCAG tRNA. Renilla gene expression was compared in various treatment conditions by taking the ratio of modified v. original construct. Cells were grown in DMEM with 10% FBS before transfection with psi-CHECK2 dual-luciferase constructs. The oligonucleotides were administered 24 hours later. Cells were lysed 24 hours after transfection to perform dual luciferase assays. Renilla luciferase activity was normalized by Firefly luciferase. The results (FIGS. 14A and 14B) show that downregulation of leuCAGtsRNA does not affect the production of proteins containing the leucine tRNA.

Example 7

LeuCAG3'tsRNA is an Essential Non-Coding RNA for Cell Viability

In order to begin to dissect the biological role of 5'tsRNAs and 3'tsRNAs (type I tsRNAs) in mammals, the abundance of specific tsRNA species was reduced using complementary locked nucleic acid/DNA-mixed antisense oligonucleotides (LNA) (FIG. 3A). The LNA forms a highly stable complex with the target RNA in a sequence specific manner, essentially inhibiting its ability to interact with their biological targets (Jepsen et al., 2004; Kurreck et al., 2002). These molecules are commonly used for inhibition of microRNA activity in vivo and in vitro (Elmén et al., 2008a; 2008b; Obad et al., 2011). After LNA-mediated depletion of LeuCAG, SerGCT, AspGTC, and MetCATi (initiator) 3'tsRNA in HeLa and HCT-116 cell lines, reduction of the LeuCAG3'tsRNA (CAGPM) was observed, but none of the others nor the GL2 control caused reduced cell viability (FIGS. 3B and 19A), using the MTS (3-(4,5-dimethylthiazol-2-yl)-5-(3-carboxymethoxyphenyl)-2-(4-sulfophenyl)-2H-tetrazolium) cell viability assay (Berridge et al., 2005).

To examine the effect observed with the LeuCAG3'tsRNA-specific LNA (CAGPM), two different 2-nt LeuCAG3'tsRNA mismatched LNAs (CAGMM and CAGMM2) were included in a set of cell viability assays (FIGS. 3C and 19B) and northern hybridization (FIG. 3D). The mismatched LNAs, and control (GL2) had no effect on cell viability (FIGS. 3C and 19B) and did not bind to LeuCAG3'tsRNA, whereas the CAGPM was bound to LeuCAG3'tsRNA, as established by the lack of a northern signal due to the strong association of LNA and tsRNA (FIG. 3D).

In concordance with the MTT assay, it was found that a reduction in the number of viable cells (determined by cell counting) in both HeLa and HCT-116 cell lines in response to the CAGPM (LeuCAG3'tsRNA knockdown), but not the GL2 and CAGMM LNAs (FIGS. 3F and 19E).

To examine whether the phenotypic effect of the LNAs was the result of tsRNA, but not of mature tRNA sequestration, northern blot analysis was performed. While RNA blots can indicate the specificity of LNAs, they can be misleading because LNAs may block the binding of competing probes as shown in FIG. 3D. The mature LeuCAG tRNA from CAGPM-transfected HeLa cells was not detected by the northern probe complementary to the LeuCAG3'tsRNA (FIG. 3D), while a northern probe complementary to the 5' end of LeuCAG tRNA detected two different sized mature tRNAs, the larger band presenting LeuCAG tRNA-LNA complexes (Elmén et al., 2008b; Lanford et al., 2010). Other mature tRNAs such as SerGCT and MetCATi, were similarly detected as two bands after transfection of SerGCTPM and MetCATiPM respectively (Fig S1C). Since no change in cell viability was observed when LNAs complementary to the 3'tsRNAs derived from SerGCT, AspGTC, or MetCATi tRNAs, (SerPM, AspPM, and MetiPM)-were transfected into cells (FIG. 3B), these results suggest that LNAs directed against tsRNAs did not functionally affect the general tRNA pool and put into question the interpretation of the northern results suggesting an association of the LNA and highly structured mature tRNA in cells (FIG. 3D).

Multiple additional approaches were used to further establish that the anti-LeuCAG3'tsRNA LNAs had no effect on the mature tRNA function in living cells. First, LNA/DNA gapmer antisense (Gap-3tsPM) oligonucleotides were used that, unlike their mixmer counterparts, can induce RNAse H-mediated cleavage of the target RNA (Kurreck et al., 2002). A gapmer LNAs against the 5'tsRNA (Gap_5'tsPM), anti-codon (GAP_codonPM), and 3'tsRNA (Gap_3'tsPM) region of LeuCAG tRNA was designed (FIG. 3E). It was found that the LNA gapmer directed against the 3'tsRNA only eliminated the LeuCAG3'tsRNA and not the corresponding mature tRNA (FIG. 3E), indicating that the LNA is unlikely to be associated with highly structured mature tRNA inside cells. It was also found that when the CAGPM (LNA mixmer) was added into the total RNA extract, it competed with the northern probe interfering with the ability to detect a tRNA signal by northern blotting (FIG. 19D). These results confirm that the CAGPM (LNA mixtmer) can inactivate the tsRNA but not mature tRNA inside cells.

Figure 20:
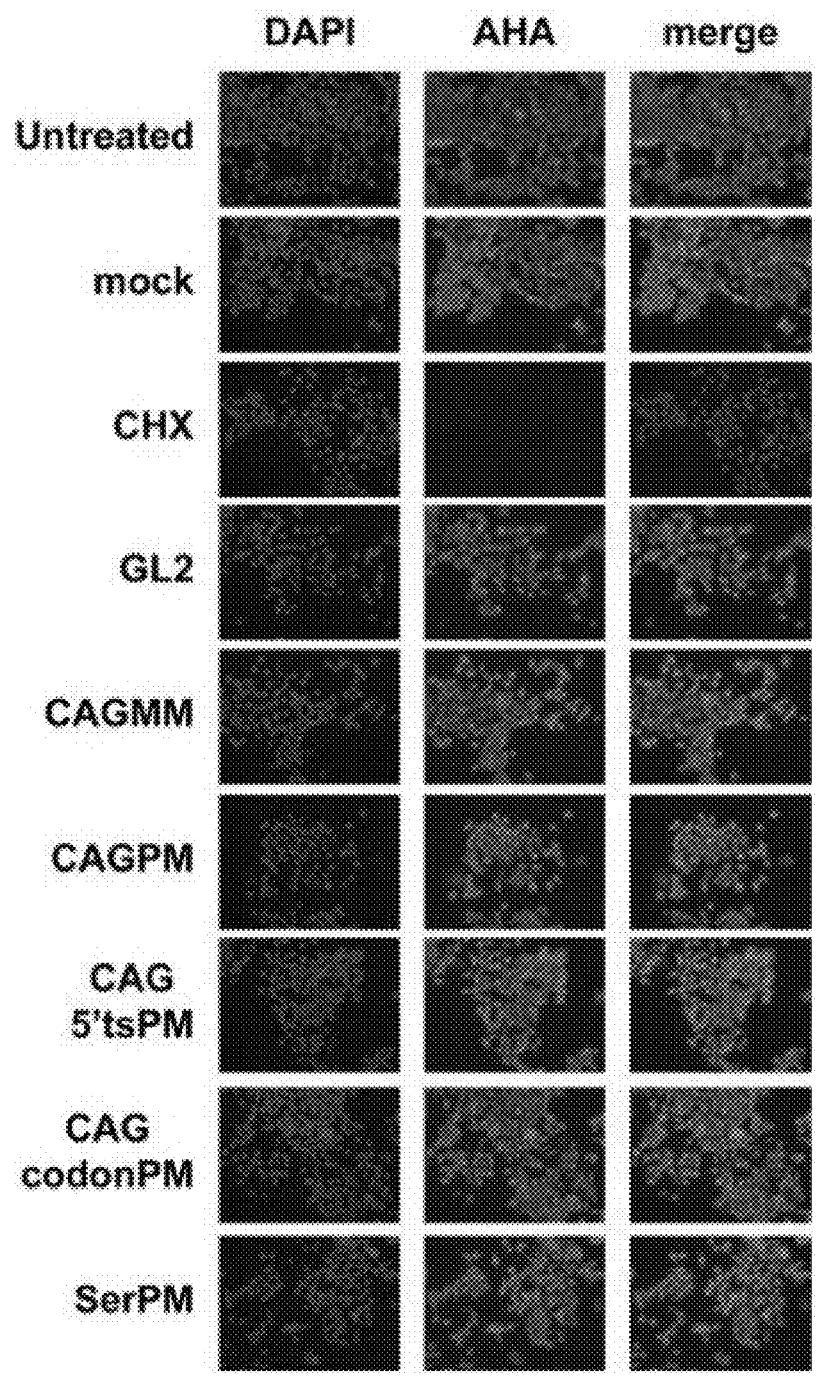
FIG. 20 shows that depletion of LeuCAG3'tsRNA does not affect global protein synthesis and the function of mature LeuCAG tRNA. Global protein synthesis assay using Click-iT® AHA Alexa Fluor® 488 assay in HCT-116 cells was performed at 24 hrs after transfection of indicated LNA. The nucleus was stained with DAPI, blue color. Protein synthesis was measured with Click-iT® AHA, green color. Merge is merged image with DAPI and Click-iT® AHA. Un, untreated cells; mock, transfection of Lipofectamine 2000 without LNA; CHX, cycloheximide treated positive control. Each LNA is described in the legend to FIG. 3.

The question of whether LNAs directed against other regions of the mature LeuCAG tRNA might interfere with its function was also addressed. Specifically, LNAs complementary to the 5'end and anticodon region of mature LeuCAG tRNA (CAG5'tsPM and CAGcodon) were transfected into cells (FIGS. 3B and 19B). Neither CAG5'tsPM nor CAGcodon LNAs impaired cell viability (FIGS. 3C). Second, it was possible to reverse the cell viability phenotype resulting from LeuCAG3'tsRNA depletion by addition of an 18nt, 21nt but not 26nt single strand RNA corresponding to the 3' end of the LeuCAG tRNA (FIGS. 3G). The fact that the 26 nt RNA did not reverse the phenotype strongly suggests the phenotypic correction with the 18 nt and 21 nt RNAs did not result from competitive binding with the complementary LNAs. Third, there were no LNA-induced changes in global protein synthesis determined by using two independent amino acid incorporation assays, Click-iT® AHA chemistry (FIGS. 13A and 20A) and $^{35}$S-methionine incorporation (FIG. 13B). Fourth, the LeuCUG codons were substituted with Leu non-CUG codons in the coding region of the psicheck2 Renilla gene while leaving the firefly luciferase gene unmodified. Thirteen of the 22 Leucine codons are recognized by the LeuCAG tRNA. After replacement of CUG with non CUG-leucine (e.g. CUC) codons, it was found that *Renilla* luciferase expression was similar regardless of the LNA (controls vs CAGPM) used for transfection (FIG. 13C). All of these experiments showed that the CAGPM LNA does not affect the function of mature tRNA, and that the inactivation of the LeuCAG3'tsRNA was responsible for the observed decrease in cell viability.

Example 8

Depletion of LeuCAG3'tsRNA Induces Apoptosis

The finding that LeuCAG3'tsRNA depletion caused the cells in culture to round up and detach from the plate (data not shown) suggested an apoptotic process (Falcieri et al., 1994).

To distinguish whether LeuCAG3'tsRNA depletion caused apoptosis or decreased cell proliferation, three different apoptosis assays were performed: Annexin V and PI (Propidium iodide) staining, Tunel (Terminal dUTP Nick End-Labeling), and PARP (poly(ADP-ribose) polymerase) cleavage (reviewed in (Elmore, 2007)) assays. After LNA transfection, cells were stained with Annexin V and PI, and analyzed by flow cytometry. (FIGS. 9A, 9B, and 21A). Three days after transfection, the percentage of LeuCAG3'tsRNA depleted HeLa cells (CAGPM) undergoing early and late apoptosis were 21.5±4.6% and 24.5±2.7, respectively, compared to 5.7±1.4% and 4.6±1.2% from control cells (GL2) (FIGS. 9A and 9B). An increase in apoptotic cells was also observed from LeuCAG3'tsRNA depleted HCT-116 cells (CAGPM) (FIG. 21A). Induction of apoptosis was further confirmed in both HeLa and HCT-116 cells by TUNEL (FIGS. 9B and 21B), and PARP cleavage (FIG. 9C) assays. This data strongly suggests that the inactivation of this specific tsRNA impairs cell viability by inducing apoptosis.

Example 9

LeuCAG3'tsRNA does not Induce Gene Repression Activity by a miRNA-Mediated Mechanism A recent report has suggested that tRNA-derived RNAs had a modest effect on mRNA expression through a miRNA-mediated mechanism (Maute et al., 2013). To determine whether the LeuCAG3'tsRNA might function through a similar process, two different experiments were pursued.

First, a luciferase assay was performed after co-transfection of an LNA and a luciferase vector containing two perfect complementary sequences of the LeuCAG3'tsRNA in tandem within the 5'UTR or 3'UTR of luciferase gene (FIG. 15A). Regardless of the location of the complementary target sequence in the mRNA neither the CAGPM nor the GL2 control LNA had an effect on luciferase expression. Similar results were obtained with other LNAs and their corresponding targets AspGTC and SerGCT3'tsRNA positioned in the 3' region of the luciferase mRNA (FIG. 22A). Furthermore, co-immunoprecipitate the 5' and 3'tsRNAs from LeuCAG, SerGCT, and AspGTC tRNA with endogenous Ago 1, 2, and 3 proteins did not occur suggesting that these tsRNAs are not associated with Ago proteins (data not shown). Collectively, these results suggest that at least a subset of 5' or 3' tsRNAs do not have trans-gene silencing activity through an Ago-mediated miRNA base-pairing mechanism.

Example 10

Depletion of Leu3tsRNA does not Change Steady State Level of Global Gene Expression In order to evaluate the effect of tsRNA depletion on global gene expression, RNAseq on LNA-treated cells was performed (FIG. 15B). High-throughput RNA sequence data was compared from HeLa and HCT-116 cells treated with the two control LNAs, GL2 and CAGMM, and the specific LNA against LeuCAG3'tsRNA (CAGPM) (FIG. 15B). Of a total of 30-40 million and 18-24 million, 50 base pair paired-end reads from HeLa and HCT-116 cells, respectively, ~75% mapped to the human genome (Table 7). The mRNA expression patterns were similar between the two control (GL2 and CAGMM) LNA-treated HeLa or HCT-116 cells with an r value (Pearson correlation coefficient) of 0.9945 and 0.9916 respectively (FIG. 15B).

TABLE 7

Sequenced sample from FIG. 15.

| Cell Line | Hela | | | HCT-116 | | |
|---|---|---|---|---|---|---|
| Transfected LNA | GL2 | CAGMM | CAGPM | GL2 | CAGMM | CAGPM |
| # of Raw reads | 39607876 | 33641365 | 30592282 | 23563831 | 22706074 | 18113883 |
| # of genomic mapped reads | 30289377 | 25684785 | 22952197 | 17846458 | 17129415 | 13408081 |
| % of mapped reads | 76.5 | 76.3 | 75.0 | 75.7 | 75.4 | 74.0 |

The mRNA expression patterns in CAGPM versus control LNA transfected HeLa and HCT-116 cells were remarkably similar with only a small number of differences. The r value between GL2-CAGPM and CAGMM-CAGPM was 0.9882 and 0.9868 from HeLa, and 0.9883 and 0.9863 from HCT-116 cells, respectively. Only the PRDM10 gene was consistently up-regulated in CAGPM vs control LNA-transfected HeLa and HCT-116 cells (FIG. 26). To test whether the CAGPM affected PRDM10 expression, the PRDM10 5'UTR and 3'UTR of the PRDM10 mRNA was cloned into the 5'UTR or 3'UTR of luciferase gene and found, as done in earlier experiments, that the CAGPM LNA had no effect on luciferase activity (FIG. 22B). Furthermore, siRNA-mediated knockdown of the PRDM10 gene did not induce apoptosis (FIG. 17C). Therefore, it appears unlikely that the LeuCAG3'tsRNA has a major effect on gene expression at the mRNA level.

Example 11

Polysomal Distribution of tsRNAs

Previous studies suggested that tsRNAs are primarily localized in the cytoplasm (Haussecker et al., 2010). Because of the role that tRNAs play in translation, experiments were designed and perfomed to determine if the tsRNAs are associated with actively translated mRNAs by examining their distribution following polysome gradient fractionation. Cytoplasmic extracts from cycloheximide-treated HeLa cells were separated in 10-50% sucrose gradients, fractionated, and each fraction was subjected to sequential RNA northern blot analysis. The sedimentation of a subset of mature tRNAs, microRNAs, GAPDH mRNA (messenger RNA), and tsRNAs was examined (FIG. 15C). GAPDH mRNA, mature LeuCAG and MetCAT e (elongator) tRNA were predominantly associated with the heavy polysome fractions, while the mature MetCAT i (initiator) tRNA was predominantly associated with the 80S initiation complex, as expected. In addition, the sedimentation of microRNAs let-7, miR-15, and miR-92a showed a similar distribution to the mature tRNAs and GAPDH mRNAs, suggesting that microRNAs are predominantly associated with polysomal mRNAs. While the 5'tsRNAs from LeuCAG and SerGCT tRNA, and 3'tsRNAs from LeuCAG, SerGCT, AspGTC, and MetCATi were predominantly found in the light sucrose fractions, the LeuCAG3'tsRNA was distributed between both the light and heavy sucrose gradient fractions (FIG. 15C). The functional significance of the observed distribution pattern is not known.

Example 12

Depletion of LeuCAG3'tsRNA Impairs Ribosome Biogenesis

The cellular polysome profile after depletion of LeuCAG3'tsRNA was studied. Remarkably, the proportion of the 40S and 80S ribosomal complexes was strikingly decreased, while the relative abundance of the 60S subunit was increased in CAGPM versus the GL2 LNA-treated cells (FIG. 16A). To determine the relative abundance of total 40S and 60S ribosomal subunits in the LNA-treated cells, cell lysates were treated with puromycin to dissociate 80S and polysomal ribosomes into free 40S and 60S subunits (Blobel and Sabatini, 1971) (FIG. 16B). In CAGPM-treated cells the amount of 40S subunits was substantially decreased to 58.1±1.1%, whereas the amount of 60S subunits were 90.7±5.7% of the control (GL2). In agreement with the decrease in 40S ribosomal subunits 18S mature rRNA (ribosomal RNA) abundance was strikingly decreased (FIG. 16C).

The decrease in 40S ribosomal subunits only occurred with the anti-3'tsRNA, CAGPM LNA. LNAs directed against the CAG5'tsPM (directed to 5' end of LeuCAG tRNA), SerPM (directed to 3' end of SerGCT tRNA), or MetiPM (directed to 3' end of Meti CAT tRNA) (FIG. 23A) did not alter the polysome profile.

To distinguish whether the CAGPM LNA reduced rRNA transcription or affected pre-rRNA processing, the different pre- and mature rRNA sequences by northern blotting using several antisense oligo probes was examined (FIG. 16D). Following depletion of LeuCAG3'tsRNA, the 30S pre-rRNA accumulated, while the 41S, 21S and 18S-E pre-rRNA signals were decreased. In addition, the LNA did not significantly affect 28S mature rRNA processing, and the 45S pre-rRNA signal was unchanged (FIG. 16E). This result was consistent in both HCT-116 and 293 cells (FIG. 23B). The accumulation of 30S and the reduction of both 21S and 18S-E pre-rRNAs combined with unchanged steady-state levels of the 45S primary transcript suggest that removal of the 5'ETS from the 30S intermediate is impaired, hence leading to the reduction in the 40S ribosomal subunits.

Interestingly, while reduction of the endonuclease and exonuclease required for rRNA processing, including XRN2, did not specifically block 5'ETS processing (FIG. 16E) (Sloan et al., 2013), the accumulation of 30S and the reduction of 21S and 18S-E, and 18S rRNA levels, has been reported to occur when expression of specific small ribosomal proteins (RPS) such as RPS6, 7, 13, 16, 24, or 28 is reduced (Choesmel et al., 2008; Flygare et al., 2007; Robledo et al., 2008).

To examine a correlation between RPS abundance and LeuCAG3'tsRNA depletion on ribosomal RNA processing, siRNAs were used to deplete RPS6, RPS10, RPS13, or RPS28. As controls, siRNAs that target the large ribosomal protein RPL7, XRN2, PRDM10, or c-MYC were used (FIG. 16E). The XRN2, 5'-3' exonuclease, is required for rRNA processing, while PRDM10 was the only gene up-regulated in LeuCAG3'tsRNA depleted HeLa and HCT-116 cell lines. C-MYC was included because it is another regulator of ribosome biogenesis (Arabi et al., 2005; Grandori et al., 2005; Grewal et al., 2005; Oskarsson and Trumpp, 2005).

Depletion of RPS6, RPS13, or RPS28 phenocopied the 5'ETS processing defect (FIG. 16E), while knockdown of RPS10, RPL7, XRN2, PRDM10, and c-MYC did not (FIG. 16E). The finding that reducing LeuCAG3'tsRNA and/or a subset of the RPS proteins have similar phenotypic effects suggests the possibility that the effects could be interrelated.

Example 13

Depletion of LeuCAG3'tsRNA Down Regulates RPS28 Protein Abundance at a Post-Transcriptional Step A computational prediction method using an RNA-hybrid program (Rehmsmeier et al., 2004) using a minimum free energy between LeuCAG3'tsRNA and 45S pre-rRNA revealed five, one, one, three and one putative LeuCAG3'tsRNA binding sites positioned in the 5'ETS, ITS1, ITS2, 28S rRNA, and 3'ETS, respectively (FIG. 24A). Two putative CAGPM LNA binding sites were also found to be nearly complementary to 45S pre-rRNA. To establish if binding to these regions of the rRNAs affected rRNA processing, LNAs against eleven of the putative tsRNA binding sites and two of the CAGPM LNA binding sites were designed. None of these LNAs affected 18S rRNA processing (FIG. 24B) suggesting that neither the LeuCAG3'tsRNA nor the CAPGPM LNA were binding to the rRNA LNA were binding to the rRNA precursors.

Next, the abundance of several ribosomal proteins were measured after depletion of LeuCAG3'tsRNA (FIG. 17A) by western blot. RPS15, 17, 19, 25, and 26 were excluded because they are not known to be associated with the 5'ETS processing defect. All of RPL proteins were also excluded since they are required for 28S not 18S rRNA maturation (Choesmel et al., 2008; Doherty et al., 2010; Flygare et al., 2007; Robledo et al., 2008).

Of the ribosomal proteins evaluated only RPS28 was notably down regulated after depletion of LeuCAG3'tsRNA, while RPS10 and RPS16 were only slightly reduced. RPS6, RPS7, RPS13, RPS19, RPS24, RPL13a, RPL7, RPL26, and XRN2 were unchanged (FIGS. 17A and 17B). The nuclear-cytoplasmic localization of RPS6 and RPS28 was also not altered (FIG. 17B). Reduction in the expression of some RPS, including RPS19, RPL11, and RPS13 or other defects in rRNA biogenesis are known to cause apoptosis (reviewed in (Dianzani and Loreni, 2008; Donati et al., 2012; Holmberg Olausson et al., 2012)). It was also found by a PARP cleavage assay that knockdown of RPS10, RPS13, or RPS28 induced apoptosis (FIG. 17C). However, RPS10 and RPS13 were eliminated from further study because RPS10 is not required for 5'ETS processing (Doherty et al., 2010), and the amount of RPS13 remained unchanged after depletion of LeuCAG3'tsRNA (FIG. 17A). Since the reduced levels of mature 18S rRNA induced by depletion of the LeuCAG3'tsRNA was recovered by over-expressing RPS28 (FIG. 17A), the rRNA processing was examined by measuring the relative abundance of 18S rRNA precursors (FIGS. 17E and 24C). CAGPM caused a 62% and 72% drop in 21S and 18S-E precursors, respectively. Over-expression of RPS28 increased the levels of 21S and 18S-E by 26% and 45%, respectively (FIGS. 17E and 24C). This together with the partial recovery of 18S rRNA strongly suggests that it is the loss of RPS28 protein that causes the disruption of ribosome biogenesis. Collectively, depletion of LeuCAG3'tsRNA reduced RPS28 protein abundance, and disrupted 5'ETS processing during pre-18S rRNA maturation, either of which can induce apoptosis (FIG. 17C).

Example 14

Depletion of LeuCAG3'tsRNA Suppress RPS28 Translational Elongation

To determine the cause for reduced RPS28 protein abundance, RPS28 mRNA abundance was measured after transfection of CAGPM LNAs. RPS28 mRNA abundance was not altered (FIG. 17D), even though RPS28 protein abundance was reduced (FIGS. 17A and 17B). To determine if the translation of the RPS28 mRNA was altered by CAGPM, the sedimentation of mRNAs encoding several ribosomal proteins and another mRNAs (NOP10) was evaluated with open reading frames of similar length to RPS28 (FIGS. 18A-18C). CAGPM transfection selectively shifted the RPS28 mRNA into lighter sucrose gradient fractions compared to the other RPS, NOP10, and GAPDH mRNAs (FIGS. 18A and 18B) suggesting that RPS28 mRNA is translationally regulated. Based on the polysomal distribution pattern translation of RPS28 mRNA could be inhibited at the initiation or elongation step. To distinguish between the two possibilities, LNA-treated cells were incubated with harringtonine, a compound that prevents the first peptide bond formation (Fresno et al., 1977; Ingolia et al., 2012), thereby essentially freezing the mRNA-ribosome complex in an 80S state at the initiation site (FIG. 25A). If RPS28 mRNA translation initiation was suppressed, the RPS28 mRNA should accumulate in sucrose gradient fractions lighter than 80S; however, if elongation was affected, the RPS28 mRNA would co-sediment with the 80S monosome. The results (FIGS. 18C and 25B) show that upon depletion of LeuCAG3'tsRNA and harringtonine treatment the RPS28 mRNA accumulates and co-sediments with the 80S monosome (FIG. 18C, fraction 6) strongly suggesting that RPS28 translation elongation is suppressed.

Results tRNA-derived small RNAs (tsRNAs) of 18-26 nucleotides in length are an abundant class of small non-coding RNAs. As shown in the examples set forth above, antisense oligonucleotide (LNA)-mediated depletion of a specific 3'tsRNA, derived from LeuCAG-tRNA, induces apoptosis. The apoptotic phenotype was reversible by complementation with the specific tsRNA through a non-miRNA-mediated mechanism. Depletion of the tsRNA slowed ribosomal protein S28 (RPS28) mRNA translational elongation and resulted in a decrease in RPS28 protein abundance. Loss of RPS28 protein caused a block in pre-18S ribosomal RNA processing, decrease in 40S ribosomal subunits, ultimately causing apoptosis. Furthermore, the examples set forth above show that overexpression of RPS28 in LNA-treated cells restored 18S rRNA processing. These findings indicate that this particular tsRNA plays an important role in normal ribosome biogenesis by regulating RPS28 protein abundance, and the onset of apoptosis. Accordingly, this group of small non-coding RNAs can fine tune gene regulation through unique mechanisms.

In the examples set forth above, programmed cell death (PCD) and ribosomal biogenesis defect was the result of CAG3'tsRNA depletion. First, the PCD effect was not observed with any of the control LNAs or those directed against other 5' and 3'tsRNAs (FIGS. 3B and 3C); secondly, cell viability could be restored with the addition of an 18 and 21 bp tsRNA, but not a larger RNA containing the same sequence (FIG. 3G); thirdly, LNA treatment had no general effect on protein synthesis, or mature LeuCAG tRNA function in cells (FIGS. 13A and 13B) and on mRNA expression (FIG. 15B).

Aberrant ribosome biogenesis (nucleolar or ribosomal stress) by inhibition of RNA polymerase I or mutation in ribosome biogenesis factors, including ribosomal proteins and pre-ribosomal factors can cause cell cycle arrest and apoptosis pathways in a p53-dependent or -independent manner in vivo and in vitro (reviewed in (Deisenroth and Zhang, 2010; Dianzani and Loreni, 2008; Donati et al., 2012; Holmberg Olausson et al., 2012)). In addition, knockdown of RPS19 has been shown to impair 18S rRNA maturation and formation of 40S subunit, and to induce apoptosis in HeLa cells (Choesmel et al., 2007).

The ribosomal protein RPS28 was reduced by the 3'CAGtsRNA or by an independent method (siRNA) and resulted in a block in 5'ETS pre-ribosomal RNA and induced apoptosis. This together with the finding that overexpression of RPS28 overcame the block in 18S rRNA production in LNA-treated cells further supports a cascade of events where 3'CAGtsRNA depletion results in a block in RPS28 translational elongation, reduced RPS28 protein, a block in 5'ETS processing of 45S pre-rRNA, reduced 18S rRNA levels and 40S ribosome subunit production, leading to apoptosis (FIG. 18D).

The importance of RPS28 protein in translation can be inferred from its localization to the head of the small ribosomal subunit where it contacts the 18s RNA and mRNA near or in the exit E-site (Idol et al., 2007; Pisarev et al., 2008). In certain embodiments a ribosome that lacks RPS28 would have detrimental effects on translation making cell death a preferred outcome to the production of ribosomes lacking RPS28. As a result, precise regulatory processes have evolved to regulate the production of this protein. In fact, other tsRNAs may also have subtle effects on the expression of other ribosomal proteins that would not necessarily have a detrimental phenotype in tissue culture cells. This would be consistent with the changing view of the role of ribosome. It is becoming more clear that ribosomes can no longer be considered a ubiquitous and homogenous macromolecular complex with identical function in all cells. Recent studies suggest developmental and cell type specific ribosomal proteins may influence the translation of specific mRNAs and promote specific developmental pathways (reviewed in (Xue and Barna, 2012)) sometimes resulting in subtle developmental defects. Aberrant ribosome biogenesis may also play a role in various malignant processes (reviewed in (Bywater et al., 2013)). Defects in ribosome biogenesis are also associated with disease states such as Treacher Collins syndrome (TCS), Shwachman-Bodian-Diamond syndrome (SBDS), Dyskeratosis congenita, 5q⁻ syndrome, and Diamond Blackfan anemia (DBA) (reviewed in (Freed et al., 2010)). Finally, it is also noted that some ribosomal proteins may have additional functions outside of their role within the ribosome (reviewed in (Lai and Xu, 2007)).

The data presented herein shows that it is possible to reduce the concentration of a tsRNA within a cell and induce an apoptotic phenotype without interrupting tRNA function, thus providing a new therapeutic approach for treating human disease.

REFERENCES

Arabi, A., Wu, S., Ridderstråle, K., Bierhoff, H., Shiue, C., Fatyol, K., Fahlén, S., Hydbring, P., Söderberg, O., Grummt, I., et al. (2005). c-Myc associates with ribosomal DNA and activates RNA polymerase I transcription. Nat. Cell Biol. 7, 303-310.

Babiarz, J. E., Ruby, J. G., Wang, Y., Bartel, D. P., and Blelloch, R. (2008). Mouse ES cells express endogenous shRNAs, siRNAs, and other Microprocessor-independent, Dicer-dependent small RNAs. Genes Dev 22, 2773-2785.

Bartel, D. (2004). MicroRNAs: Genomics, Biogenesis, Mechanism, and Function. Cell 116, 281-297.

Berridge, M. V., Herst, P. M., and Tan, A. S. (2005). Tetrazolium dyes as tools in cell biology: new insights into their cellular reduction. Biotechnol Annu Rev 11, 127-152.

Blobel, G., and Sabatini, D. (1971). Dissociation of Mammalian Polyribosomes Into Subunits by Puromycin. Proc Natl Acad Sci USA 68, 390-394.

Bywater, M. J., Pearson, R. B., McArthur, G. A., and Hannan, R. D. (2013). Dysregulation of the basal RNA polymerase transcription apparatus in cancer. Nat. Rev. Cancer 13, 299-314.

Choesmel, V., Bacqueville, D., Rouquette, J., Noaillac-Depeyre, J., Fribourg, S., Crétien, A., Leblanc, T., Tchernia, G., Da Costa, L., and Gleizes, P.-E. (2007). Impaired ribosome biogenesis in Diamond-Blackfan anemia. Blood 109, 1275-1283.

Choesmel, V., Fribourg, S., Aguissa-Touré, A.-H., Pinaud, N., Legrand, P., Gazda, H. T., and Gleizes, P.-E. (2008). Mutation of ribosomal protein RPS24 in Diamond-Blackfan anemia results in a ribosome biogenesis disorder. Hum. Mol. Genet. 17, 1253-1263.

Cole, C., Sobala, A., Lu, C., Thatcher, S. R., Bowman, A., Brown, J. W. S., Green, P. J., Barton, G. J., and Hutvagner, G. (2009). Filtering of deep sequencing data reveals the existence of abundant Dicer-dependent small RNAs derived from tRNAs. Rna 15, 2147-2160.

Couvillion, M. T., Bounova, G., Purdom, E., Speed, T. P., and Collins, K. (2012). A Tetrahymena Piwi Bound to Mature tRNA 3' Fragments Activates the Exonuclease Xrn2 for RNA Processing in the Nucleus. Mol Cell 48, 509-520.

Couvillion, M. T., Sachidanandam, R., and Collins, K. (2010). A growth-essential Tetrahymena Piwi protein carries tRNA fragment cargo. Genes Dev 24, 2742-2747.

Croce, C. M., and Calin, G. A. (2005). miRNAs, cancer, and stem cell division. Cell 122, 6-7.

Deisenroth, C., and Zhang, Y. (2010). Ribosome biogenesis surveillance: probing the ribosomal protein-Mdm2-p53 pathway. Oncogene 29, 4253-4260.

Dianzani, I., and Loreni, F. (2008). Diamond-Blackfan anemia: a ribosomal puzzle. Haematologica 93, 1601-1604.

Doherty, L., Sheen, M. R., Vlachos, A., Choesmel, V., O'Donohue, M.-F., Clinton, C., Schneider, H. E., Sieff, C. A., Newburger, P. E., Ball, S. E., et al. (2010). Ribosomal protein genes RPS10 and RPS26 are commonly mutated in Diamond-Blackfan anemia. Am. J. Hum. Genet. 86, 222-228.

Donati, G., Montanaro, L., and Derenzini, M. (2012). Ribosome biogenesis and control of cell proliferation: p53 is not alone. Cancer Res 72, 1602-1607.

Elbashir, S. M., Harborth, J., Lendeckel, W., Yalcin, A., Weber, K., and Tuschl, T. (2001). Duplexes of 21-nucleotide RNAs mediate RNA interference in cultured mammalian cells. Nature 411, 494-498.

Elmén, J., Lindow, M., Silahtaroglu, A., Bak, M., Christensen, M., Lind-Thomsen, A., Hedtjärn, M., Hansen, J. B., Hansen, H. F., Straarup, E. M., et al. (2008a). Antagonism of microRNA-122 in mice by systemically administered LNA-antimiR leads to up-regulation of a large set of predicted target mRNAs in the liver. Nucleic Acids Res 36, 1153-1162.

Elmén, J., Lindow, M., tz, S. S. U., Lawrence, M., Petri, A., Obad, S., Lindholm, M., rn, M. H. A., Hansen, H. F., Berger, U., et al. (2008b). LNA-mediated microRNA silencing in non-human primates. Nature 452, 896-899.

Elmore, S. (2007). Apoptosis: a review of programmed cell death. Toxicol Pathol 35, 495-516.

Falcieri, E., Gobbi, P., Zamai, L., and Vitale, M. (1994). Ultrastructural features of apoptosis. Scanning Microsc. 8, 653-65; discussion 665-6.

Findeiss, S., Langenberger, D., Stadler, P. F., and Hoffmann, S. (2011). Traces of post-transcriptional RNA modifications in deep sequencing data. Biol Chem 392, 305-313.

Flygare, J., Aspesi, A., Bailey, J. C., Miyake, K., Caffrey, J. M., Karlsson, S., and Ellis, S. R. (2007). Human RPS19, the gene mutated in Diamond-Blackfan anemia, encodes a ribosomal protein required for the maturation of 40S ribosomal subunits. Blood 109, 980-986.

Freed, E. F., Bleichert, F., Dutca, L. M., and Baserga, S. J. (2010). When ribosomes go bad: diseases of ribosome biogenesis. Mol Biosyst 6, 481-493.

Fresno, M. M., Jiménez, A. A., and Vazquez, D. D. (1977). Inhibition of translation in eukaryotic systems by harringtonine. Febs J 72, 323-330.

Fuchs, G., Diges, C., Kohlstaedt, L. A., Wehner, K. A., and Sarnow, P. (2011). Proteomic analysis of ribosomes: translational control of mRNA populations by glycogen synthase GYS1. J. Mol. Biol. 410, 118-130.

Gebetsberger, J., Zywicki, M., Künzi, A., and Polacek, N. (2012). tRNA-Derived Fragments Target the Ribosome and Function as Regulatory Non-Coding RNA in *Haloferax volcanii*. Archaea 2012, 1-11.

Grandori, C., Gomez-Roman, N., Felton-Edkins, Z. A., Ngouenet, C., Galloway, D. A., Eisenman, R. N., and White, R. J. (2005). c-Myc binds to human ribosomal DNA and stimulates transcription of rRNA genes by RNA polymerase I. Nat. Cell Biol. 7, 311-318.

Grewal, S. S., Li, L., Orian, A., Eisenman, R. N., and Edgar, B. A. (2005). Myc-dependent regulation of ribosomal RNA synthesis during Drosophila development. Nat. Cell Biol. 7, 295-302.

Hadjiolova, K. V., Nicoloso, M., Mazan, S., Hadjiolov, A. A., and Bachellerie, J. P. (1993). Alternative pre-rRNA processing pathways in human cells and their alteration by cycloheximide inhibition of protein synthesis. Eur. J. Biochem. 212, 211-215.

Haussecker, D., Huang, Y., Lau, A., Parameswaran, P., Fire, A. Z., and Kay, M. A. (2010). Human tRNA-derived small RNAs in the global regulation of RNA silencing. Rna 16, 673-695.

Holmberg Olausson, K., Nistér, M., and Lindstrom, M. (2012). p53-Dependent and Independent Nucleolar Stress Responses. Cells 1, 774-798.

Idol, R. A., Robledo, S., Du, H.-Y., Crimmins, D. L., Wilson, D. B., Ladenson, J. H., Bessler, M., and Mason, P. J. (2007). Cells depleted for RPS19, a protein associated with Diamond Blackfan Anemia, show defects in 18S ribosomal RNA synthesis and small ribosomal subunit production. Blood Cells Mol. Dis. 39, 35-43.

Ingolia, N. T., Brar, G. A., Rouskin, S., McGeachy, A. M., and Weissman, J. S. (2012). The ribosome profiling strategy for monitoring translation in vivo by deep sequencing of ribosome-protected mRNA fragments. Nat Protoc 7,1534-1550.

Jepsen, J. S., Sørensen, M. D., and Wengel, J. (2004). Locked nucleic acid: a potent nucleic acid analog in therapeutics and biotechnology. Oligonucleotides 14, 130-146.

Kim, Y., and Kim, V. N. (2012). MicroRNA factory: RISC assembly from precursor microRNAs. Mol Cell 46, 384-386.

Kurreck, J., Wyszko, E., Gillen, C., and Erdmann, V. (2002). Design of antisense oligonucleotides stabilized by locked nucleic acids. Nucleic Acids Res 30, 1911.

Lai, M.-D., and Xu, J. (2007). Ribosomal proteins and colorectal cancer. Curr. Genomics 8, 43-49.

Lanford, R. E., Hildebrandt-Eriksen, E. S., Petri, A., Persson, R., Lindow, M., Munk, M. E., Kauppinen, S., and Ørum, H. (2010). Therapeutic silencing of microRNA-122 in primates with chronic hepatitis C virus infection. Science 327, 198-201.

Lee, Y. S., Shibata, Y., Malhotra, A., and Dutta, A. (2009). A novel class of small RNAs: tRNA derived RNA fragments (tRFs). Genes Dev 23, 2639-2649.

Li, Z., Ender, C., Meister, G., Moore, P. S., Chang, Y., and John, B. (2012). Extensive terminal and asymmetric processing of small RNAs from rRNAs, snoRNAs, snRNAs, and tRNAs. Nucleic Acids Res 40, 6787-6799.

Martens-Uzunova, E. S., Olvedy, M., and Jenster, G. (2013). Beyond microRNA—novel RNAs derived from small non-coding RNA and their implication in cancer. Cancer Lett. 340, 201-211.

Maute, R. L., Schneider, C., Sumazin, P., Holmes, A., Califano, A., Basso, K., and Dalla-Favera, R. (2013). tRNA-derived microRNA modulates proliferation and the DNA damage response and is down-regulated in B cell lymphoma. Proc Natl Acad Sci USA 110, 1404-1409.

Obad, S., Santos, Dos, C. O., Petri, A., Heidenblad, M., Broom, O., Ruse, C., Fu, C., Lindow, M., Stenvang, J., Straarup, E. M., et al. (2011). Silencing of microRNA families by seed-targeting tiny LNAs. Nat. Genet. 43, 371-378.

Oskarsson, T., and Trumpp, A. (2005). The Myc trilogy: lord of RNA polymerases. Nat. Cell Biol. 7, 215-217.

Pederson, T. (2010). Regulatory RNAs derived from transfer RNA? Rna 16, 1865-1869.

Pisarev, A. V., Kolupaeva, V. G., Yusupov, M. M., Hellen, C. U. T., and Pestova, T. V. (2008). Ribosomal position and contacts of mRNA in eukaryotic translation initiation complexes. The EMBO Journal 27, 1609-1621.

Rehmsmeier, M., Steffen, P., Hochsmann, M., and Giegerich, R. (2004). Fast and effective prediction of microRNA/target duplexes. Rna 10, 1507-1517.

Renda, M. J., Rosenblatt, J. D., Klimatcheva, E., Demeter, L. M., Bambara, R. A., and Planelles, V. (2001). Mutation of the methylated tRNA(Lys) (3) residue A58 disrupts reverse transcription and inhibits replication of human immunodeficiency virus type 1. J Virol 75, 9671-9678.

Robledo, S., Idol, R. A., Crimmins, D. L., Ladenson, J. H., Mason, P. J., and Bessler, M. (2008). The role of human ribosomal proteins in the maturation of rRNA and ribosome production. Rna 14, 1918-1929.

Saikia, M., Fu, Y., Pavon-Eternod, M., He, C., and Pan, T. (2010). Genome-wide analysis of N1 methyl-adenosine modification in human tRNAs. Rna 16, 1317-1327.

Sloan, K. E. K., Mattijssen, S. S., Lebaron, S. S., Tollervey, D. D., Pruijn, G. J. M. G., and Watkins, N. J. N. (2013). Both endonucleolytic and exonucleolytic cleavage mediate ITS1 removal during human ribosomal RNA processing. The Journal of Cell Biology 200, 577-588.

Sobala, A., and Hutvágner, G. (2011). Transfer RNA-derived fragments: origins, processing, and functions. Wiley Interdiscip Rev RNA 2, 853-862.

Sobala, A., and Hutvágner, G. (2013). Small RNAs derived from the 5' end of tRNA can inhibit protein translation in human cells. RNA Biology 10, 553-563.

Trapnell, C., Pachter, L., and Salzberg, S. L. (2009). TopHat: discovering splice junctions with RNA-Seq. Bioinformatics 25, 1105-1111.

Trapnell, C., Roberts, A., Goff, L., Pertea, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nat Protoc 7, 562-578.

Trapnell, C., Williams, B. A., Pertea, G., Mortazavi, A., Kwan, G., van Baren, M. J., Salzberg, S. L., Wold, B. J., and Pachter, L. (2010). Transcript assembly and quantification by RNA-Seq reveals unannotated transcripts and isoform switching during cell differentiation. Nat Biotechnol 28, 511-515.

Xue, S., and Barna, M. (2012). Specialized ribosomes: a new frontier in gene regulation and organismal biology. Nature Reviews Molecular Cell Biology 13, 355-369.

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

What is claimed is:

1. A method of treating cancer in a subject, the method comprising administering to the subject a pharmaceutical composition comprising an oligonucleotide that targets a specific tRNA-derived small RNA (tsRNA) comprising:
   (i) 10 to 12 contiguous unmodified nucleic acids having 100% complementarity to the tsRNA and at least three locked nucleic acids at the 5' end and the 3' end of the oligonucleotide,
   (ii) 15 nucleic acids comprising at least 7 unmodified nucleic acids and at least 7 locked nucleic acids wherein no more than two unmodified nucleic acids are contiguous and no more than two locked nucleic acids are contiguous,
   (iii) 10 to 12 contiguous unmodified nucleic acids having 100% complementarity to the tsRNA and at least three modified nucleic acids at the 5' end and the 3' end of the oligonucleotide, wherein said at least three modified nucleic acids are selected from phosphorothioate nucleic acids, sugar modified nucleic acids, and a combination thereof, or
   (iv) 15 nucleic acids comprising at least 7 unmodified nucleic acids and at least 7 modified nucleic acids, wherein no more than two unmodified nucleic acids are contiguous and no more than two modified nucleic acids are contiguous, and wherein said at least 7 modified nucleic acids are selected from phosphorothioate nucleic acids, sugar modified nucleic acids, and a combination thereof,
   wherein the oligonucleotide is complementary to one selected from the group consisting of leucine-CAG tsRNA, tsRNA derived from the 5' end of mature leucine-CAG tRNA (leuCAG5tsRNA), tsRNA derived from the 3' end of mature leucine-CAG tRNA (leuCAG3tsRNA), serine-GCT tsRNA, aspartic acid-GTC tsRNA, and methionine-CAT tsRNA, thereby inhibiting viability of a cell of the cancer in the subject.

2. The method of claim 1, wherein the oligonucleotide is selected from the group consisting of:

(a) GGTGtcaggagtggGATT, (SEQ ID NO: 11)
   (b) GACCgcteggccatccTGAC, (SEQ ID NO: 12)
   (c) ACGCagcgccttagACCG, (SEQ ID NO: 13)
   (d) GACTgcgacctgaacGCAG, (SEQ ID NO: 14)
   (e) CGCCtccaggggagACTG, (SEQ ID NO: 15)
   (f) GGGAttcgaacccacGCCT, (SEQ ID NO: 16)
   (g) CGAAcccacgcctccAGGG, (SEQ ID NO: 17)
   (h) TTCGaacccacgcctCCAG, and (SEQ ID NO: 18)
   (i) GATTcgaacccacgcCTCC, (SEQ ID NO: 19)

wherein uppercase letters represent locked nucleic acids and lowercase letters represent unmodified nucleic acids.

3. The method of claim 1, wherein the oligonucleotide is selected from the group consisting of:

(a) tGTcAGgAgTggGaT, (SEQ ID NO: 2)
   (b) tCTcACgAgTggGaT, (SEQ ID NO: 3)
   (c) tGTcAAgAcTggGaT, (SEQ ID NO: 4)
   (d) gcTcgGcCaTCcTgA, (SEQ ID NO: 5)
   (e) GaGacTgcGAccTGa, (SEQ ID NO: 6)
   (f) cgACgAGgAtGggAt, and (SEQ ID NO: 7)
   (g) TagCaGAgGAtgGTt, (SEQ ID NO: 8)

wherein uppercase letters represent locked nucleic acids and lowercase letters represent unmodified nucleic acids.

4. The method of claim 1, wherein the pharmaceutical composition further comprises a pharmaceutically acceptable carrier.

5. The method of claim 1, wherein inhibiting viability of a cell prevents cell proliferation, induces apoptosis, or induces cellular necrosis.

6. The method of claim 5, wherein inhibiting viability of a cell induces apoptosis.

7. The method of claim 1, wherein the cell is a human cell.

8. The method of claim 1, wherein said oligonucleotide is complementary to one selected from the group consisting of leucine-CAG tsRNA, leuCAG5tsRNA and leuCAG3tsRNA.

9. The method of claim 8, wherein said oligonucleotide is complementary to leucine-CAG tsRNA.

10. The method of claim 1, wherein said oligonucleotide is complementary to leuCAG5tsRNA.

11. The method of claim 1, wherein said oligonucleotide is complementary to leuCAG3tsRNA.

12. A method of inhibiting cell proliferation in a subject, the method comprising administering to the subject a pharmaceutical composition comprising an oligonucleotide that targets a specific tRNA-derived small RNA (tsRNA) comprising:
(i) 10 to 12 contiguous unmodified nucleic acids having 100% complementarity to the tsRNA and at least three locked nucleic acids at the 5' end and the 3' end of the oligonucleotide,
(ii) 15 nucleic acids comprising at least 7 unmodified nucleic acids and at least 7 locked nucleic acids wherein no more than two unmodified nucleic acids are contiguous and no more than two locked nucleic acids are contiguous,
(iii) 10 to 12 contiguous unmodified nucleic acids having 100% complementarity to the tsRNA and at least three modified nucleic acids at the 5' end and the 3' end of the oligonucleotide, wherein said at least three modified nucleic acids are selected from phosphorothioate nucleic acids, sugar modified nucleic acids, and a combination thereof, or
(iv) 15 nucleic acids comprising at least 7 unmodified nucleic acids and at least 7 modified nucleic acids, wherein no more than two unmodified nucleic acids are contiguous and no more than two modified nucleic acids are contiguous, and wherein said at least 7 modified nucleic acids are selected from phosphorothioate nucleic acids, sugar modified nucleic acids, and a combination thereof,
wherein the oligonucleotide is complementary to one selected from the group consisting of leucine-CAG tsRNA, tsRNA derived from the 5' end of mature leucine-CAG tRNA (leuCAG5tsRNA), tsRNA derived from the 3' end of mature leucine-CAG tRNA (leuCAG3tsRNA), serine-GCT tsRNA, aspartic acid-GTC tsRNA, and methionine-CAT tsRNA, thereby inhibiting cell proliferation in the subject.

13. A method of inhibiting viability of a cell in a subject, the method comprising administering to the subject a pharmaceutical composition comprising an oligonucleotide that targets a specific tRNA-derived small RNA (tsRNA) comprising:
(i) 10 to 12 contiguous unmodified nucleic acids having 100% complementarity to the tsRNA and at least three locked nucleic acids at the 5' end and the 3' end of the oligonucleotide,
(ii) 15 nucleic acids comprising at least 7 unmodified nucleic acids and at least 7 locked nucleic acids wherein no more than two unmodified nucleic acids are contiguous and no more than two locked nucleic acids are contiguous,
(iii) 10 to 12 contiguous unmodified nucleic acids having 100% complementarity to the tsRNA and at least three modified nucleic acids at the 5' end and the 3' end of the oligonucleotide, wherein said at least three modified nucleic acids are selected from phosphorothioate nucleic acids, sugar modified nucleic acids, and a combination thereof, or
(iv) 15 nucleic acids comprising at least 7 unmodified nucleic acids and at least 7 modified nucleic acids, wherein no more than two unmodified nucleic acids are contiguous and no more than two modified nucleic acids are contiguous, and wherein said at least 7 modified nucleic acids are selected from phosphorothioate nucleic acids, sugar modified nucleic acids, and a combination thereof,
wherein the oligonucleotide is complementary to one selected from the group consisting of leucine-CAG tsRNA, tsRNA derived from the 5' end of mature leucine-CAG tRNA (leuCAG5tsRNA), tsRNA derived from the 3' end of mature leucine-CAG tRNA (leuCAG3tsRNA), serine-GCT tsRNA, aspartic acid-GTC tsRNA, and methionine-CAT tsRNA, thereby inhibiting viability of a cell in the subject.

* * * * *

SEQUENCE LISTING

```
<160> NUMBER OF SEQ ID NOS: 78

<210> SEQ ID NO 1
<211> LENGTH: 16
<212> TYPE: DNA
<213> ORGANISM: Artificial Sequence
<220> FEATURE:
<223> OTHER INFORMATION: GL2c mixmer oligonucleotide
<220> FEATURE:
<221> NAME/KEY: misc_feature
<222> LOCATION: (1)..(1)
<223> OTHER INFORMATION: n = locked nucleic acid guanine
<220> FEATURE:
<221> NAME/KEY: misc_feature
<222> LOCATION: (4)..(4)
<223> OTHER INFORMATION: n = locked nucleic acid cytosine
<220> FEATURE:
<221> NAME/KEY: misc_feature
<222> LOCATION: (6)..(6)
<223> OTHER INFORMATION: n = locked nucleic acid cytosine
<220> FEATURE:
<221> NAME/KEY: misc_feature
<222> LOCATION: (8)..(8)
<223> OTHER INFORMATION: n = locked nucleic acid guanine
<220> FEATURE:
<221> NAME/KEY: misc_feature
<222> LOCATION: (11)..(11)
<223> OTHER INFORMATION: n = locked nucleic acid thymine
<220> FEATURE:
<221> NAME/KEY: misc_feature
<222> LOCATION: (13)..(13)
<223> OTHER INFORMATION: n = locked nucleic acid cytosine
<220> FEATURE:
<221> NAME/KEY: misc_feature
<222> LOCATION: (14)..(14)
<223> OTHER INFORMATION: n = locked nucleic acid thymine
<220> FEATURE:
<221> NAME/KEY: misc_feature
<222> LOCATION: (16)..(16)
<223> OTHER INFORMATION: n = locked nucleic acid cytosine

<400> SEQUENCE: 1
ntangngnaa nanntn                                                    16

<210> SEQ ID NO 2
<211> LENGTH: 15
<212> TYPE: DNA
<213> ORGANISM: Artificial Sequence
<220> FEATURE:
<223> OTHER INFORMATION: leu3ts15PM mixmer oligonucleotide
<220> FEATURE:
```

```
<221> NAME/KEY: misc_feature
<222> LOCATION: (2)..(2)
<223> OTHER INFORMATION: n = locked nucleic acid guanine
<220> FEATURE:
<221> NAME/KEY: misc_feature
<222> LOCATION: (3)..(3)
<223> OTHER INFORMATION: n = locked nucleic acid thymine
<220> FEATURE:
<221> NAME/KEY: misc_feature
<222> LOCATION: (5)..(5)
<223> OTHER INFORMATION: n = locked nucleic acid adenine
<220> FEATURE:
<221> NAME/KEY: misc_feature
<222> LOCATION: (6)..(6)
<223> OTHER INFORMATION: n = locked nucleic acid guanine
<220> FEATURE:
<221> NAME/KEY: misc_feature
<222> LOCATION: (8)..(8)
<223> OTHER INFORMATION: n = locked nucleic acid adenine
<220> FEATURE:
<221> NAME/KEY: misc_feature
<222> LOCATION: (10)..(10)
<223> OTHER INFORMATION: n = locked nucleic acid thymine
<220> FEATURE:
<221> NAME/KEY: misc_feature
<222> LOCATION: (13)..(13)
<223> OTHER INFORMATION: n = locked nucleic acid guanine
<220> FEATURE:
<221> NAME/KEY: misc_feature
<222> LOCATION: (15)..(15)
<223> OTHER INFORMATION: n = locked nucleic acid thymine

<400> SEQUENCE: 2
tnncnngngn ggnan                                            15

<210> SEQ ID NO 3
<211> LENGTH: 15
<212> TYPE: DNA
<213> ORGANISM: Artificial Sequence
<220> FEATURE:
<223> OTHER INFORMATION: leu3ts15MM1 mixmer oligonucleotide
<220> FEATURE:
<221> NAME/KEY: misc_feature
<222> LOCATION: (2)..(2)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid thymine
<220> FEATURE:
<221> NAME/KEY: misc_feature
<222> LOCATION: (5)..(5)
<223> OTHER INFORMATION: n = locked nucleic acid adenine
<220> FEATURE:
<221> NAME/KEY: misc_feature
<222> LOCATION: (6)..(6)
<223> OTHER INFORMATION: n = locked nucleic acid cytosine
<220> FEATURE:
<221> NAME/KEY: misc_feature
<222> LOCATION: (8)..(8)
<223> OTHER INFORMATION: n = locked nucleic acid adenine
<220> FEATURE:
<221> NAME/KEY: misc_feature
<222> LOCATION: (10)..(10)
<223> OTHER INFORMATION: n = locked nucleic acid thymine
<220> FEATURE:
<221> NAME/KEY: misc_feature
<222> LOCATION: (13)..(13)
<223> OTHER INFORMATION: n = locked nucleic acid guanine
<220> FEATURE:
<221> NAME/KEY: misc_feature
<222> LOCATION: (15)..(15)
<223> OTHER INFORMATION: n = locked nucleic acid thymine

<400> SEQUENCE: 3
tnncnngngn ggnan                                            15
```

<210> SEQ ID NO 4
<211> LENGTH: 15
<212> TYPE: DNA
<213> ORGANISM: Artificial Sequence
<220> FEATURE:
<223> OTHER INFORMATION: leu3ts15MM2 mixmer oligonucleotide
<220> FEATURE:
<221> NAME/KEY: misc_feature
<222> LOCATION: (2)..(2)
<223> OTHER INFORMATION: n = locked nucleic acid guanine
<220> FEATURE:
<221> NAME/KEY: misc_feature
<222> LOCATION: (3)..(3)
<223> OTHER INFORMATION: n = locked nucleic acid thymine
<220> FEATURE:
<221> NAME/KEY: misc_feature
<222> LOCATION: (5)..(6)
<223> OTHER INFORMATION: n = locked nucleic acid adenine
<220> FEATURE:
<221> NAME/KEY: misc_feature
<222> LOCATION: (8)..(8)
<223> OTHER INFORMATION: n = locked nucleic acid adenine
<220> FEATURE:
<221> NAME/KEY: misc_feature
<222> LOCATION: (10)..(10)
<223> OTHER INFORMATION: n = locked nucleic acid thymine
<220> FEATURE:
<221> NAME/KEY: misc_feature
<222> LOCATION: (13)..(13)
<223> OTHER INFORMATION: n = locked nucleic acid guanine
<220> FEATURE:
<221> NAME/KEY: misc_feature
<222> LOCATION: (15)..(15)
<223> OTHER INFORMATION: n = locked nucleic acid thymine

<400> SEQUENCE: 4
tnncnngncn ggnan                                                    15

<210> SEQ ID NO 5
<211> LENGTH: 15
<212> TYPE: DNA
<213> ORGANISM: Artificial Sequence
<220> FEATURE:
<223> OTHER INFORMATION: leu5ts15PM mixmer oligonucleotide
<220> FEATURE:
<221> NAME/KEY: misc_feature
<222> LOCATION: (3)..(3)
<223> OTHER INFORMATION: n = locked nucleic acid thymine
<220> FEATURE:
<221> NAME/KEY: misc_feature
<222> LOCATION: (6)..(6)
<223> OTHER INFORMATION: n = locked nucleic acid guanine
<220> FEATURE:
<221> NAME/KEY: misc_feature
<222> LOCATION: (8)..(8)
<223> OTHER INFORMATION: n = locked nucleic acid cytosine
<220> FEATURE:
<221> NAME/KEY: misc_feature
<222> LOCATION: (10)..(10)
<223> OTHER INFORMATION: n = locked nucleic acid thymine
<220> FEATURE:
<221> NAME/KEY: misc_feature
<222> LOCATION: (11)..(11)
<223> OTHER INFORMATION: n = locked nucleic acid cytosine
<220> FEATURE:
<221> NAME/KEY: misc_feature
<222> LOCATION: (13)..(13)
<223> OTHER INFORMATION: n = locked nucleic acid thymine
<220> FEATURE:
<221> NAME/KEY: misc_feature
<222> LOCATION: (15)..(15)
<223> OTHER INFORMATION: n = locked nucleic acid adenine

<400> SEQUENCE: 5
gcncgncnan ncngn                                                       15

<210> SEQ ID NO 6
<211> LENGTH: 15
<212> TYPE: DNA
<213> ORGANISM: Artificial Sequence
<220> FEATURE:
<223> OTHER INFORMATION: CAGcodon mixmer oligonucleotide
<220> FEATURE:
<221> NAME/KEY: misc_feature
<222> LOCATION: (1)..(1)
<223> OTHER INFORMATION: n = locked nucleic acid guanine
<220> FEATURE:
<221> NAME/KEY: misc_feature
<222> LOCATION: (3)..(3)
<223> OTHER INFORMATION: n = locked nucleic acid guanine
<220> FEATURE:
<221> NAME/KEY: misc_feature
<222> LOCATION: (6)..(6)
<223> OTHER INFORMATION: n = locked nucleic acid thymine
<220> FEATURE:
<221> NAME/KEY: misc_feature
<222> LOCATION: (9)..(9)
<223> OTHER INFORMATION: n = locked nucleic acid guanine
<220> FEATURE:
<221> NAME/KEY: misc_feature
<222> LOCATION: (10)..(10)
<223> OTHER INFORMATION: n = locked nucleic acid adenine
<220> FEATURE:
<221> NAME/KEY: misc_feature
<222> LOCATION: (13)..(13)
<223> OTHER INFORMATION: n = locked nucleic acid thymine
<220> FEATURE:
<221> NAME/KEY: misc_feature
<222> LOCATION: (14)..(14)
<223> OTHER INFORMATION: n = locked nucleic acid guanine

<400> SEQUENCE: 6
nanacngcnn ccnna                                                       15

<210> SEQ ID NO 7
<211> LENGTH: 15
<212> TYPE: DNA
<213> ORGANISM: Artificial Sequence
<220> FEATURE:
<223> OTHER INFORMATION: ser15GCTPM mixmer oligonucleotide
<220> FEATURE:
<221> NAME/KEY: misc_feature
<222> LOCATION: (3)..(3)
<223> OTHER INFORMATION: n = locked nucleic acid adenine
<220> FEATURE:
<221> NAME/KEY: misc_feature
<222> LOCATION: (4)..(4)
<223> OTHER INFORMATION: n = locked nucleic acid guanine
<220> FEATURE:
<221> NAME/KEY: misc_feature
<222> LOCATION: (6)..(6)
<223> OTHER INFORMATION: n = locked nucleic acid adenine
<220> FEATURE:
<221> NAME/KEY: misc_feature
<222> LOCATION: (7)..(7)
<223> OTHER INFORMATION: n = locked nucleic acid guanine
<220> FEATURE:
<221> NAME/KEY: misc_feature
<222> LOCATION: (9)..(9)
<223> OTHER INFORMATION: n = locked nucleic acid adenine
<220> FEATURE:
<221> NAME/KEY: misc_feature
<222> LOCATION: (11)..(11)
<223> OTHER INFORMATION: n = locked nucleic acid guanine
<220> FEATURE:
<221> NAME/KEY: misc_feature
<222> LOCATION: (14)..(14)
<223> OTHER INFORMATION: n = locked nucleic acid adenine

<400> SEQUENCE: 7

```
cgnngnngnt nggnt                                                   15

<210> SEQ ID NO 8
<211> LENGTH: 15
<212> TYPE: DNA
<213> ORGANISM: Artificial Sequence
<220> FEATURE:
<223> OTHER INFORMATION: meti15PM mixmer oligonucleotide
<220> FEATURE:
<221> NAME/KEY: misc_feature
<222> LOCATION: (1)..(1)
<223> OTHER INFORMATION: n = locked nucleic acid thymine
<220> FEATURE:
<221> NAME/KEY: misc_feature
<222> LOCATION: (4)..(4)
<223> OTHER INFORMATION: n = locked nucleic acid cytosine
<220> FEATURE:
<221> NAME/KEY: misc_feature
<222> LOCATION: (6)..(6)
<223> OTHER INFORMATION: n = locked nucleic acid guanine
<220> FEATURE:
<221> NAME/KEY: misc_feature
<222> LOCATION: (7)..(7)
<223> OTHER INFORMATION: n = locked nucleic acid adenine
<220> FEATURE:
<221> NAME/KEY: misc_feature
<222> LOCATION: (9)..(9)
<223> OTHER INFORMATION: n = locked nucleic acid guanine
<220> FEATURE:
<221> NAME/KEY: misc_feature
<222> LOCATION: (10)..(10)
<223> OTHER INFORMATION: n = locked nucleic acid adenine
<220> FEATURE:
<221> NAME/KEY: misc_feature
<222> LOCATION: (13)..(13)
<223> OTHER INFORMATION: n = locked nucleic acid guanine
<220> FEATURE:
<221> NAME/KEY: misc_feature
<222> LOCATION: (14)..(14)
<223> OTHER INFORMATION: n = locked nucleic acid thymine

<400> SEQUENCE: 8
nagnanngnn tgnnt                                                   15

<210> SEQ ID NO 9
<211> LENGTH: 19
<212> TYPE: DNA
<213> ORGANISM: Artificial Sequence
<220> FEATURE:
<223> OTHER INFORMATION: AspPM gapmer oligonucleotide
<220> FEATURE:
<221> NAME/KEY: misc_feature
<222> LOCATION: (1)..(3)
<223> OTHER INFORMATION: n = locked nucleic acid cytosine
<220> FEATURE:
<221> NAME/KEY: misc_feature
<222> LOCATION: (17)..(17)
<223> OTHER INFORMATION: n = locked nucleic acid adenine
<220> FEATURE:
<221> NAME/KEY: misc_feature
<222> LOCATION: (18)..(19)
<223> OTHER INFORMATION: n = locked nucleic acid cytosine

<400> SEQUENCE: 9
nnngtcgggg aatcgannn                                               19

<210> SEQ ID NO 10
<211> LENGTH: 19
<212> TYPE: DNA
<213> ORGANISM: Artificial Sequence
<220> FEATURE:
<223> OTHER INFORMATION: GL2b gapmer oligonucleotide
<220> FEATURE:
```

```
<221> NAME/KEY: misc_feature
<222> LOCATION: (1)..(1)
<223> OTHER INFORMATION: n = locked nucleic acid thymine
<220> FEATURE:
<221> NAME/KEY: misc_feature
<222> LOCATION: (2)..(2)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid guanine
<220> FEATURE:
<221> NAME/KEY: misc_feature
<222> LOCATION: (17)..(17)
<223> OTHER INFORMATION: n = locked nucleic acid adenine
<220> FEATURE:
<221> NAME/KEY: misc_feature
<222> LOCATION: (18)..(18)
<223> OTHER INFORMATION: n = locked nucleic acid cytosine
<220> FEATURE:
<221> NAME/KEY: misc_feature
<222> LOCATION: (19)..(19)
<223> OTHER INFORMATION: n = locked nucleic acid guanine

<400> SEQUENCE: 10
nnnaagtatt ccgcgtnnn                                              19

<210> SEQ ID NO 11
<211> LENGTH: 18
<212> TYPE: DNA
<213> ORGANISM: Artificial Sequence
<220> FEATURE:
<223> OTHER INFORMATION: lue3ts gapmer oligonucleotide
<220> FEATURE:
<221> NAME/KEY: misc_feature
<222> LOCATION: (1)..(2)
<223> OTHER INFORMATION: n = locked nucleic acid guanine
<220> FEATURE:
<221> NAME/KEY: misc_feature
<222> LOCATION: (3)..(3)
<223> OTHER INFORMATION: n = locked nucleic acid thymine
<220> FEATURE:
<221> NAME/KEY: misc_feature
<222> LOCATION: (4)..(4)
<223> OTHER INFORMATION: n = locked nucleic acid guanine
<220> FEATURE:
<221> NAME/KEY: misc_feature
<222> LOCATION: (15)..(15)
<223> OTHER INFORMATION: n = locked nucleic acid guanine
<220> FEATURE:
<221> NAME/KEY: misc_feature
<222> LOCATION: (16)..(16)
<223> OTHER INFORMATION: n = locked nucleic acid adenine
<220> FEATURE:
<221> NAME/KEY: misc_feature
<222> LOCATION: (17)..(18)
<223> OTHER INFORMATION: n = locked nucleic acid thymine

<400> SEQUENCE: 11
nnnntcagga gtggnnnn                                               18

<210> SEQ ID NO 12
<211> LENGTH: 20
<212> TYPE: DNA
<213> ORGANISM: Artificial Sequence
<220> FEATURE:
<223> OTHER INFORMATION: leu5ts gapmer oligonucleotide
<220> FEATURE:
<221> NAME/KEY: misc_feature
<222> LOCATION: (1)..(1)
<223> OTHER INFORMATION: n = locked nucleic acid guanine
<220> FEATURE:
<221> NAME/KEY: misc_feature
<222> LOCATION: (2)..(2)
<223> OTHER INFORMATION: n = locked nucleic acid adenine
```

```
<220> FEATURE:
<221> NAME/KEY: misc_feature
<222> LOCATION: (3)..(4)
<223> OTHER INFORMATION: n = locked nucleic acid cytosine
<220> FEATURE:
<221> NAME/KEY: misc_feature
<222> LOCATION: (17)..(17)
<223> OTHER INFORMATION: n = locked nucleic acid thymine
<220> FEATURE:
<221> NAME/KEY: misc_feature
<222> LOCATION: (18)..(18)
<223> OTHER INFORMATION: n = locked nucleic acid guanine
<220> FEATURE:
<221> NAME/KEY: misc_feature
<222> LOCATION: (19)..(19)
<223> OTHER INFORMATION: n = locked nucleic acid adenine
<220> FEATURE:
<221> NAME/KEY: misc_feature
<222> LOCATION: (20)..(20)
<223> OTHER INFORMATION: n = locked nucleic acid cytosine

<400> SEQUENCE: 12
nnnngctcgg ccatccnnnn                                               20

<210> SEQ ID NO 13
<211> LENGTH: 18
<212> TYPE: DNA
<213> ORGANISM: Artificial Sequence
<220> FEATURE:
<223> OTHER INFORMATION: leuA gapmer oligonucleotide
<220> FEATURE:
<221> NAME/KEY: misc_feature
<222> LOCATION: (1)..(1)
<223> OTHER INFORMATION: n = locked nucleic acid adenine
<220> FEATURE:
<221> NAME/KEY: misc_feature
<222> LOCATION: (2)..(2)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid guanine
<220> FEATURE:
<221> NAME/KEY: misc_feature
<222> LOCATION: (4)..(4)
<223> OTHER INFORMATION: n = locked nucleic acid cytosine
<220> FEATURE:
<221> NAME/KEY: misc_feature
<222> LOCATION: (15)..(15)
<223> OTHER INFORMATION: n = locked nucleic acid adenine
<220> FEATURE:
<221> NAME/KEY: misc_feature
<222> LOCATION: (16)..(17)
<223> OTHER INFORMATION: n = locked nucleic acid cytosine
<220> FEATURE:
<221> NAME/KEY: misc_feature
<222> LOCATION: (18)..(18)
<223> OTHER INFORMATION: n = locked nucleic acid guanine

<400> SEQUENCE: 13
nnnnagcgcc ttagnnnn                                                 18

<210> SEQ ID NO 14
<211> LENGTH: 19
<212> TYPE: DNA
<213> ORGANISM: Artificial Sequence
<220> FEATURE:
<223> OTHER INFORMATION: leuB gapmer oligonucleotide
<220> FEATURE:
<221> NAME/KEY: misc_feature
<222> LOCATION: (1)..(1)
<223> OTHER INFORMATION: n = locked nucleic acid guanine
<220> FEATURE:
<221> NAME/KEY: misc_feature
<222> LOCATION: (2)..(2)
```

```
<223> OTHER INFORMATION: n = locked nucleic acid adenine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (4)..(4)
<223> OTHER INFORMATION: n = locked nucleic acid thymine
<220> FEATURE:
<221> NAME/KEY: misc_feature
<222> LOCATION: (16)..(16)
<223> OTHER INFORMATION: n = locked nucleic acid guanine
<220> FEATURE:
<221> NAME/KEY: misc_feature
<222> LOCATION: (17)..(17)
<223> OTHER INFORMATION: n = locked nucleic acid cytosine
<220> FEATURE:
<221> NAME/KEY: misc_feature
<222> LOCATION: (18)..(18)
<223> OTHER INFORMATION: n = locked nucleic acid adenine
<220> FEATURE:
<221> NAME/KEY: misc_feature
<222> LOCATION: (19)..(19)
<223> OTHER INFORMATION: n = locked nucleic acid guanine

<400> SEQUENCE: 14
nnnngcgacc tgaacnnnn                                                   19

<210> SEQ ID NO 15
<211> LENGTH: 18
<212> TYPE: DNA
<213> ORGANISM: Artificial Sequence
<220> FEATURE:
<223> OTHER INFORMATION: leuC gapmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (2)..(2)
<223> OTHER INFORMATION: n = locked nucleic acid guanine
<220> FEATURE:
<221> NAME/KEY: misc_feature
<222> LOCATION: (3)..(4)
<223> OTHER INFORMATION: n = locked nucleic acid cytosine
<220> FEATURE:
<221> NAME/KEY: misc_feature
<222> LOCATION: (15)..(15)
<223> OTHER INFORMATION: n = locked nucleic acid adenine
<220> FEATURE:
<221> NAME/KEY: misc_feature
<222> LOCATION: (16)..(16)
<223> OTHER INFORMATION: n = locked nucleic acid cytosine
<220> FEATURE:
<221> NAME/KEY: misc_feature
<222> LOCATION: (17)..(17)
<223> OTHER INFORMATION: n = locked nucleic acid thymine
<220> FEATURE:
<221> NAME/KEY: misc_feature
<222> LOCATION: (18)..(18)
<223> OTHER INFORMATION: n = locked nucleic acid guanine

<400> SEQUENCE: 15
nnnntccagg ggagnnnn                                                    18

<210> SEQ ID NO 16
<211> LENGTH: 19
<212> TYPE: DNA
<213> ORGANISM: Artificial Sequence
<220> FEATURE:
<223> OTHER INFORMATION: leuD gapmer oligonucleotide
<220> FEATURE:
<221> NAME/KEY: misc_feature
```

<222> LOCATION: (1)..(3)
<223> OTHER INFORMATION: n = locked nucleic acid guanine
<220> FEATURE:
<221> NAME/KEY: misc_feature
<222> LOCATION: (4)..(4)
<223> OTHER INFORMATION: n = locked nucleic acid adenine
<220> FEATURE:
<221> NAME/KEY: misc_feature
<222> LOCATION: (16)..(16)
<223> OTHER INFORMATION: n = locked nucleic acid guanine
<220> FEATURE:
<221> NAME/KEY: misc_feature
<222> LOCATION: (17)..(18)
<223> OTHER INFORMATION: n = locked nucleic acid cytosine
<220> FEATURE:
<221> NAME/KEY: misc_feature
<222> LOCATION: (19)..(19)
<223> OTHER INFORMATION: n = locked nucleic acid thymine

<400> SEQUENCE: 16
nnnnttcgaa cccacnnnn                                              19

<210> SEQ ID NO 17
<211> LENGTH: 19
<212> TYPE: DNA
<213> ORGANISM: Artificial Sequence
<220> FEATURE:
<223> OTHER INFORMATION: leuD-6bp gapmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (2)..(2)
<223> OTHER INFORMATION: n = locked nucleic acid guanine
<220> FEATURE:
<221> NAME/KEY: misc_feature
<222> LOCATION: (3)..(4)
<223> OTHER INFORMATION: n = locked nucleic acid adenine
<220> FEATURE:
<221> NAME/KEY: misc_feature
<222> LOCATION: (16)..(16)
<223> OTHER INFORMATION: n = locked nucleic acid adenine
<220> FEATURE:
<221> NAME/KEY: misc_feature
<222> LOCATION: (17)..(19)
<223> OTHER INFORMATION: n = locked nucleic acid guanine

<400> SEQUENCE: 17
nnnncccacg cctccnnnn                                              19

<210> SEQ ID NO 18
<211> LENGTH: 19
<212> TYPE: DNA
<213> ORGANISM: Artificial Sequence
<220> FEATURE:
<223> OTHER INFORMATION: leuD-4bp gapmer oligonucleotide
<220> FEATURE:
<221> NAME/KEY: misc_feature
<222> LOCATION: (1)..(2)
<223> OTHER INFORMATION: n = locked nucleic acid thymine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (4)..(4)
<223> OTHER INFORMATION: n = locked nucleic acid guanine
<220> FEATURE:
<221> NAME/KEY: misc_feature
<222> LOCATION: (16)..(17)
<223> OTHER INFORMATION: n = locked nucleic acid cytosine
<220> FEATURE:

```
<221> NAME/KEY: misc_feature
<222> LOCATION: (18)..(18)
<223> OTHER INFORMATION: n = locked nucleic acid adenine
<220> FEATURE:
<221> NAME/KEY: misc_feature
<222> LOCATION: (19)..(19)
<223> OTHER INFORMATION: n = locked nucleic acid guanine

<400> SEQUENCE: 18
nnnnaaccca cgcctnnnn                                                19

<210> SEQ ID NO 19
<211> LENGTH: 19
<212> TYPE: DNA
<213> ORGANISM: Artificial Sequence
<220> FEATURE:
<223> OTHER INFORMATION: leuD-2bp gapmer oligonucleotide
<220> FEATURE:
<221> NAME/KEY: misc_feature
<222> LOCATION: (1)..(1)
<223> OTHER INFORMATION: n = locked nucleic acid guanine
<220> FEATURE:
<221> NAME/KEY: misc_feature
<222> LOCATION: (2)..(2)
<223> OTHER INFORMATION: n = locked nucleic acid adenine
<220> FEATURE:
<221> NAME/KEY: misc_feature
<222> LOCATION: (3)..(4)
<223> OTHER INFORMATION: n = locked nucleic acid thymine
<220> FEATURE:
<221> NAME/KEY: misc_feature
<222> LOCATION: (16)..(16)
<223> OTHER INFORMATION: n = locked nucleic acid cytosine
<220> FEATURE:
<221> NAME/KEY: misc_feature
<222> LOCATION: (17)..(17)
<223> OTHER INFORMATION: n = locked nucleic acid thymine
<220> FEATURE:
<221> NAME/KEY: misc_feature
<222> LOCATION: (18)..(19)
<223> OTHER INFORMATION: n = locked nucleic acid cytosine

<400> SEQUENCE: 19
nnnncgaacc cacgcnnnn                                                19

<210> SEQ ID NO 20
<211> LENGTH: 18
<212> TYPE: DNA
<213> ORGANISM: Artificial Sequence
<220> FEATURE:
<223> OTHER INFORMATION: GAP_GL2 gapmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (2)..(2)
<223> OTHER INFORMATION: n = locked nucleic acid guanine
<220> FEATURE:
<221> NAME/KEY: misc_feature
<222> LOCATION: (3)..(3)
<223> OTHER INFORMATION: n = locked nucleic acid thymine
<220> FEATURE:
<221> NAME/KEY: misc_feature
<222> LOCATION: (4)..(4)
<223> OTHER INFORMATION: n = locked nucleic acid adenine
<220> FEATURE:
<221> NAME/KEY: misc_feature
<222> LOCATION: (15)..(16)
<223> OTHER INFORMATION: n = locked nucleic acid thymine
<220> FEATURE:
<221> NAME/KEY: misc_feature
<222> LOCATION: (17)..(17)
<223> OTHER INFORMATION: n = locked nucleic acid cytosine
```

<220> FEATURE:
<221> NAME/KEY: misc_feature
<222> LOCATION: (18)..(18)
<223> OTHER INFORMATION: n = locked nucleic acid guanine

<400> SEQUENCE: 20
nnnncgcgga atacnnnn                                                 18

<210> SEQ ID NO 21
<211> LENGTH: 19
<212> TYPE: DNA
<213> ORGANISM: Artificial Sequence
<220> FEATURE:
<223> OTHER INFORMATION: GAP_codonPM gapmer oligonucleotide
<220> FEATURE:
<221> NAME/KEY: misc_feature
<222> LOCATION: (1)..(1)
<223> OTHER INFORMATION: n = locked nucleic acid guanine
<220> FEATURE:
<221> NAME/KEY: misc_feature
<222> LOCATION: (2)..(2)
<223> OTHER INFORMATION: n = locked nucleic acid adenine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (4)..(4)
<223> OTHER INFORMATION: n = locked nucleic acid thymine
<220> FEATURE:
<221> NAME/KEY: misc_feature
<222> LOCATION: (16)..(16)
<223> OTHER INFORMATION: n = locked nucleic acid guanine
<220> FEATURE:
<221> NAME/KEY: misc_feature
<222> LOCATION: (17)..(17)
<223> OTHER INFORMATION: n = locked nucleic acid cytosine
<220> FEATURE:
<221> NAME/KEY: misc_feature
<222> LOCATION: (18)..(18)
<223> OTHER INFORMATION: n = locked nucleic acid adenine
<220> FEATURE:
<221> NAME/KEY: misc_feature
<222> LOCATION: (19)..(19)
<223> OTHER INFORMATION: n = locked nucleic acid guanine

<400> SEQUENCE: 21
nnnngcgacc tgaacnnnn                                                19

<210> SEQ ID NO 22
<211> LENGTH: 18
<212> TYPE: DNA
<213> ORGANISM: Artificial Sequence
<220> FEATURE:
<223> OTHER INFORMATION: r571 mixmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (5)..(5)
<223> OTHER INFORMATION: n = locked nucleic acid cytosine
<220> FEATURE:
<221> NAME/KEY: misc_feature
<222> LOCATION: (7)..(7)
<223> OTHER INFORMATION: n = locked nucleic acid cytosine
<220> FEATURE:
<221> NAME/KEY: misc_feature
<222> LOCATION: (9)..(9)

```
<223> OTHER INFORMATION: n = locked nucleic acid adenine
<220> FEATURE:
<221> NAME/KEY: misc_feature
<222> LOCATION: (12)..(12)
<223> OTHER INFORMATION: n = locked nucleic acid cytosine
<220> FEATURE:
<221> NAME/KEY: misc_feature
<222> LOCATION: (14)..(14)
<223> OTHER INFORMATION: n = locked nucleic acid thymine
<220> FEATURE:
<221> NAME/KEY: misc_feature
<222> LOCATION: (17)..(17)
<223> OTHER INFORMATION: n = locked nucleic acid cytosine

<400> SEQUENCE: 22
ngnancncnc gncntcnc                                                    18

<210> SEQ ID NO 23
<211> LENGTH: 19
<212> TYPE: DNA
<213> ORGANISM: Artificial Sequence
<220> FEATURE:
<223> OTHER INFORMATION: r1936 mixmer oligonucleotide
<220> FEATURE:
<221> NAME/KEY: misc_feature
<222> LOCATION: (2)..(3)
<223> OTHER INFORMATION: n = locked nucleic acid cytosine
<220> FEATURE:
<221> NAME/KEY: misc_feature
<222> LOCATION: (6)..(6)
<223> OTHER INFORMATION: n = locked nucleic acid cytosine
<220> FEATURE:
<221> NAME/KEY: misc_feature
<222> LOCATION: (8)..(8)
<223> OTHER INFORMATION: n = locked nucleic acid cytosine
<220> FEATURE:
<221> NAME/KEY: misc_feature
<222> LOCATION: (10)..(10)
<223> OTHER INFORMATION: n = locked nucleic acid cytosine
<220> FEATURE:
<221> NAME/KEY: misc_feature
<222> LOCATION: (12)..(12)
<223> OTHER INFORMATION: n = locked nucleic acid cytosine
<220> FEATURE:
<221> NAME/KEY: misc_feature
<222> LOCATION: (14)..(14)
<223> OTHER INFORMATION: n = locked nucleic acid cytosine
<220> FEATURE:
<221> NAME/KEY: misc_feature
<222> LOCATION: (15)..(15)
<223> OTHER INFORMATION: n = locked nucleic acid adenine
<220> FEATURE:
<221> NAME/KEY: misc_feature
<222> LOCATION: (17)..(17)
<223> OTHER INFORMATION: n = locked nucleic acid cytosine
<220> FEATURE:
<221> NAME/KEY: misc_feature
<222> LOCATION: (19)..(19)
<223> OTHER INFORMATION: n = locked nucleic acid cytosine

<400> SEQUENCE: 23
cnnganangn cgnncnan                                                    19

<210> SEQ ID NO 24
<211> LENGTH: 19
<212> TYPE: DNA
<213> ORGANISM: Artificial Sequence
<220> FEATURE:
<223> OTHER INFORMATION: r2075 mixmer oligonucleotide
<220> FEATURE:
<221> NAME/KEY: misc_feature
<222> LOCATION: (1)..(1)
<223> OTHER INFORMATION: n = locked nucleic acid adenine
<220> FEATURE:
<221> NAME/KEY: misc_feature
```

```
<222> LOCATION: (3)..(3)
<223> OTHER INFORMATION: n = locked nucleic acid cytosine
<220> FEATURE:
<221> NAME/KEY: misc_feature
<222> LOCATION: (5)..(5)
<223> OTHER INFORMATION: n = locked nucleic acid cytosine
<220> FEATURE:
<221> NAME/KEY: misc_feature
<222> LOCATION: (6)..(6)
<223> OTHER INFORMATION: n = locked nucleic acid adenine
<220> FEATURE:
<221> NAME/KEY: misc_feature
<222> LOCATION: (8)..(8)
<223> OTHER INFORMATION: n = locked nucleic acid cytosine
<220> FEATURE:
<221> NAME/KEY: misc_feature
<222> LOCATION: (10)..(10)
<223> OTHER INFORMATION: n = locked nucleic acid cytosine
<220> FEATURE:
<221> NAME/KEY: misc_feature
<222> LOCATION: (12)..(12)
<223> OTHER INFORMATION: n = locked nucleic acid adenine
<220> FEATURE:
<221> NAME/KEY: misc_feature
<222> LOCATION: (14)..(14)
<223> OTHER INFORMATION: n = locked nucleic acid adenine
<220> FEATURE:
<221> NAME/KEY: misc_feature
<222> LOCATION: (17)..(17)
<223> OTHER INFORMATION: n = locked nucleic acid cytosine
<220> FEATURE:
<221> NAME/KEY: misc_feature
<222> LOCATION: (18)..(18)
<223> OTHER INFORMATION: n = locked nucleic acid adenine

<400> SEQUENCE: 24
ntncnncngn cncngannc                                                    19

<210> SEQ ID NO 25
<211> LENGTH: 15
<212> TYPE: DNA
<213> ORGANISM: Artificial Sequence
<220> FEATURE:
<223> OTHER INFORMATION: r2960a mixmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid adenine
<220> FEATURE:
<221> NAME/KEY: misc_feature
<222> LOCATION: (5)..(5)
<223> OTHER INFORMATION: n = locked nucleic acid cytosine
<220> FEATURE:
<221> NAME/KEY: misc_feature
<222> LOCATION: (7)..(7)
<223> OTHER INFORMATION: n = locked nucleic acid cytosine
<220> FEATURE:
<221> NAME/KEY: misc_feature
<222> LOCATION: (9)..(9)
<223> OTHER INFORMATION: n = locked nucleic acid cytosine
<220> FEATURE:
<221> NAME/KEY: misc_feature
<222> LOCATION: (11)..(11)
<223> OTHER INFORMATION: n = locked nucleic acid adenine
<220> FEATURE:
<221> NAME/KEY: misc_feature
<222> LOCATION: (13)..(14)
<223> OTHER INFORMATION: n = locked nucleic acid cytosine

<400> SEQUENCE: 25
ncncncncng ncnng                                                        15
```

```
<210> SEQ ID NO 26
<211> LENGTH: 18
<212> TYPE: DNA
<213> ORGANISM: Artificial Sequence
<220> FEATURE:
<223> OTHER INFORMATION: r2960b mixmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (5)..(5)
<223> OTHER INFORMATION: n = locked nucleic acid adenine
<220> FEATURE:
<221> NAME/KEY: misc_feature
<222> LOCATION: (7)..(7)
<223> OTHER INFORMATION: n = locked nucleic acid cytosine
<220> FEATURE:
<221> NAME/KEY: misc_feature
<222> LOCATION: (9)..(9)
<223> OTHER INFORMATION: n = locked nucleic acid cytosine
<220> FEATURE:
<221> NAME/KEY: misc_feature
<222> LOCATION: (11)..(11)
<223> OTHER INFORMATION: n = locked nucleic acid cytosine
<220> FEATURE:
<221> NAME/KEY: misc_feature
<222> LOCATION: (13)..(13)
<223> OTHER INFORMATION: n = locked nucleic acid adenine
<220> FEATURE:
<221> NAME/KEY: misc_feature
<222> LOCATION: (15)..(15)
<223> OTHER INFORMATION: n = locked nucleic acid cytosine
<220> FEATURE:
<221> NAME/KEY: misc_feature
<222> LOCATION: (18)..(18)
<223> OTHER INFORMATION: n = locked nucleic acid guanine

<400> SEQUENCE: 26
ncncncncnc ngncncgn                                                18

<210> SEQ ID NO 27
<211> LENGTH: 15
<212> TYPE: DNA
<213> ORGANISM: Artificial Sequence
<220> FEATURE:
<223> OTHER INFORMATION: r5823a mixmer oligonucleotide
<220> FEATURE:
<221> NAME/KEY: misc_feature
<222> LOCATION: (2)..(2)
<223> OTHER INFORMATION: n = locked nucleic acid cytosine
<220> FEATURE:
<221> NAME/KEY: misc_feature
<222> LOCATION: (4)..(4)
<223> OTHER INFORMATION: n = locked nucleic acid cytosine
<220> FEATURE:
<221> NAME/KEY: misc_feature
<222> LOCATION: (6)..(6)
<223> OTHER INFORMATION: n = locked nucleic acid cytosine
<220> FEATURE:
<221> NAME/KEY: misc_feature
<222> LOCATION: (8)..(8)
<223> OTHER INFORMATION: n = locked nucleic acid cytosine
<220> FEATURE:
<221> NAME/KEY: misc_feature
<222> LOCATION: (10)..(10)
<223> OTHER INFORMATION: n = locked nucleic acid cytosine
<220> FEATURE:
<221> NAME/KEY: misc_feature
<222> LOCATION: (13)..(13)
<223> OTHER INFORMATION: n = locked nucleic acid adenine
```

```
<220> FEATURE:
<221> NAME/KEY: misc_feature
<222> LOCATION: (14)..(14)
<223> OTHER INFORMATION: n = locked nucleic acid cytosine

<400> SEQUENCE: 27
cngngncngn cgnna                                                         15

<210> SEQ ID NO 28
<211> LENGTH: 19
<212> TYPE: DNA
<213> ORGANISM: Artificial Sequence
<220> FEATURE:
<223> OTHER INFORMATION: r5823b mixmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (5)..(5)
<223> OTHER INFORMATION: n = locked nucleic acid cytosine
<220> FEATURE:
<221> NAME/KEY: misc_feature
<222> LOCATION: (7)..(7)
<223> OTHER INFORMATION: n = locked nucleic acid cytosine
<220> FEATURE:
<221> NAME/KEY: misc_feature
<222> LOCATION: (10)..(10)
<223> OTHER INFORMATION: n = locked nucleic acid adenine
<220> FEATURE:
<221> NAME/KEY: misc_feature
<222> LOCATION: (12)..(12)
<223> OTHER INFORMATION: n = locked nucleic acid adenine
<220> FEATURE:
<221> NAME/KEY: misc_feature
<222> LOCATION: (13)..(13)
<223> OTHER INFORMATION: n = locked nucleic acid cytosine
<220> FEATURE:
<221> NAME/KEY: misc_feature
<222> LOCATION: (15)..(15)
<223> OTHER INFORMATION: n = locked nucleic acid cytosine
<220> FEATURE:
<221> NAME/KEY: misc_feature
<222> LOCATION: (16)..(16)
<223> OTHER INFORMATION: n = locked nucleic acid adenine
<220> FEATURE:
<221> NAME/KEY: misc_feature
<222> LOCATION: (18)..(18)
<223> OTHER INFORMATION: n = locked nucleic acid guanine

<400> SEQUENCE: 28
ngncngncgn cnncnncnt                                                     19

<210> SEQ ID NO 29
<211> LENGTH: 15
<212> TYPE: DNA
<213> ORGANISM: Artificial Sequence
<220> FEATURE:
<223> OTHER INFORMATION: r6162 mixmer oligonucleotide
<220> FEATURE:
<221> NAME/KEY: misc_feature
<222> LOCATION: (1)..(1)
<223> OTHER INFORMATION: n = locked nucleic acid adenine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (4)..(4)
```

```
<223> OTHER INFORMATION: n = locked nucleic acid adenine
<220> FEATURE:
<221> NAME/KEY: misc_feature
<222> LOCATION: (6)..(6)
<223> OTHER INFORMATION: n = locked nucleic acid cytosine
<220> FEATURE:
<221> NAME/KEY: misc_feature
<222> LOCATION: (8)..(8)
<223> OTHER INFORMATION: n = locked nucleic acid cytosine
<220> FEATURE:
<221> NAME/KEY: misc_feature
<222> LOCATION: (11)..(12)
<223> OTHER INFORMATION: n = locked nucleic acid cytosine
<220> FEATURE:
<221> NAME/KEY: misc_feature
<222> LOCATION: (14)..(14)
<223> OTHER INFORMATION: n = locked nucleic acid adenine

<400> SEQUENCE: 29
ncnncngncc nngnc                                                  15

<210> SEQ ID NO 30
<211> LENGTH: 15
<212> TYPE: DNA
<213> ORGANISM: Artificial Sequence
<220> FEATURE:
<223> OTHER INFORMATION: r8527 mixmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (5)..(5)
<223> OTHER INFORMATION: n = locked nucleic acid cytosine
<220> FEATURE:
<221> NAME/KEY: misc_feature
<222> LOCATION: (7)..(7)
<223> OTHER INFORMATION: n = locked nucleic acid cytosine
<220> FEATURE:
<221> NAME/KEY: misc_feature
<222> LOCATION: (9)..(9)
<223> OTHER INFORMATION: n = locked nucleic acid cytosine
<220> FEATURE:
<221> NAME/KEY: misc_feature
<222> LOCATION: (11)..(11)
<223> OTHER INFORMATION: n = locked nucleic acid cytosine
<220> FEATURE:
<221> NAME/KEY: misc_feature
<222> LOCATION: (13)..(13)
<223> OTHER INFORMATION: n = locked nucleic acid cytosine
<220> FEATURE:
<221> NAME/KEY: misc_feature
<222> LOCATION: (15)..(15)
<223> OTHER INFORMATION: n = locked nucleic acid cytosine

<400> SEQUENCE: 30
ncnancncng nancn                                                  15

<210> SEQ ID NO 31
<211> LENGTH: 15
<212> TYPE: DNA
<213> ORGANISM: Artificial Sequence
<220> FEATURE:
<223> OTHER INFORMATION: r8546 mixmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
```

```
<222> LOCATION: (4)..(4)
<223> OTHER INFORMATION: n = locked nucleic acid adenine
<220> FEATURE:
<221> NAME/KEY: misc_feature
<222> LOCATION: (5)..(5)
<223> OTHER INFORMATION: n = locked nucleic acid cytosine
<220> FEATURE:
<221> NAME/KEY: misc_feature
<222> LOCATION: (7)..(7)
<223> OTHER INFORMATION: n = locked nucleic acid cytosine
<220> FEATURE:
<221> NAME/KEY: misc_feature
<222> LOCATION: (9)..(9)
<223> OTHER INFORMATION: n = locked nucleic acid adenine
<220> FEATURE:
<221> NAME/KEY: misc_feature
<222> LOCATION: (11)..(11)
<223> OTHER INFORMATION: n = locked nucleic acid cytosine
<220> FEATURE:
<221> NAME/KEY: misc_feature
<222> LOCATION: (13)..(14)
<223> OTHER INFORMATION: n = locked nucleic acid cytosine

<400> SEQUENCE: 31
ncgnncncnc ncnng                                                    15

<210> SEQ ID NO 32
<211> LENGTH: 16
<212> TYPE: DNA
<213> ORGANISM: Artificial Sequence
<220> FEATURE:
<223> OTHER INFORMATION: r9079 mixmer oligonucleotide
<220> FEATURE:
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (5)..(5)
<223> OTHER INFORMATION: n = locked nucleic acid cytosine
<220> FEATURE:
<221> NAME/KEY: misc_feature
<222> LOCATION: (8)..(8)
<223> OTHER INFORMATION: n = locked nucleic acid cytosine
<220> FEATURE:
<221> NAME/KEY: misc_feature
<222> LOCATION: (10)..(10)
<223> OTHER INFORMATION: n = locked nucleic acid cytosine
<220> FEATURE:
<221> NAME/KEY: misc_feature
<222> LOCATION: (12)..(12)
<223> OTHER INFORMATION: n = locked nucleic acid cytosine
<220> FEATURE:
<221> NAME/KEY: misc_feature
<222> LOCATION: (15)..(15)
<223> OTHER INFORMATION: n = locked nucleic acid adenine
<220> FEATURE:
<221> NAME/KEY: misc_feature
<222> LOCATION: (16)..(16)
<223> OTHER INFORMATION: n = locked nucleic acid cytosine

<400> SEQUENCE: 32
ngncncgncn cncgnn                                                   16

<210> SEQ ID NO 33
<211> LENGTH: 15
<212> TYPE: DNA
<213> ORGANISM: Artificial Sequence
<220> FEATURE:
<223> OTHER INFORMATION: r12034 mixmer oligonucleotide
<220> FEATURE:
```

```
<221> NAME/KEY: misc_feature
<222> LOCATION: (1)..(1)
<223> OTHER INFORMATION: n = locked nucleic acid cytosine
<220> FEATURE:
<221> NAME/KEY: misc_feature
<222> LOCATION: (3)..(3)
<223> OTHER INFORMATION: n = locked nucleic acid cytosine
<220> FEATURE:
<221> NAME/KEY: misc_feature
<222> LOCATION: (5)..(5)
<223> OTHER INFORMATION: n = locked nucleic acid adenine
<220> FEATURE:
<221> NAME/KEY: misc_feature
<222> LOCATION: (7)..(8)
<223> OTHER INFORMATION: n = locked nucleic acid adenine
<220> FEATURE:
<221> NAME/KEY: misc_feature
<222> LOCATION: (10)..(10)
<223> OTHER INFORMATION: n = locked nucleic acid cytosine
<220> FEATURE:
<221> NAME/KEY: misc_feature
<222> LOCATION: (12)..(12)
<223> OTHER INFORMATION: n = locked nucleic acid adenine
<220> FEATURE:
<221> NAME/KEY: misc_feature
<222> LOCATION: (14)..(14)
<223> OTHER INFORMATION: n = locked nucleic acid adenine

<400> SEQUENCE: 33
ngncngnngn gngng                                                      15

<210> SEQ ID NO 34
<211> LENGTH: 14
<212> TYPE: DNA
<213> ORGANISM: Artificial Sequence
<220> FEATURE:
<223> OTHER INFORMATION: r4143 mixmer oligonucleotide
<220> FEATURE:
<221> NAME/KEY: misc_feature
<222> LOCATION: (1)..(1)
<223> OTHER INFORMATION: n = locked nucleic acid guanine
<220> FEATURE:
<221> NAME/KEY: misc_feature
<222> LOCATION: (3)..(3)
<223> OTHER INFORMATION: n = locked nucleic acid thymine
<220> FEATURE:
<221> NAME/KEY: misc_feature
<222> LOCATION: (5)..(5)
<223> OTHER INFORMATION: n = locked nucleic acid guanine
<220> FEATURE:
<221> NAME/KEY: misc_feature
<222> LOCATION: (7)..(7)
<223> OTHER INFORMATION: n = locked nucleic acid guanine
<220> FEATURE:
<221> NAME/KEY: misc_feature
<222> LOCATION: (9)..(9)
<223> OTHER INFORMATION: n = locked nucleic acid guanine
<220> FEATURE:
<221> NAME/KEY: misc_feature
<222> LOCATION: (11)..(11)
<223> OTHER INFORMATION: n = locked nucleic acid guanine
<220> FEATURE:
<221> NAME/KEY: misc_feature
<222> LOCATION: (13)..(13)
<223> OTHER INFORMATION: n = locked nucleic acid guanine

<400> SEQUENCE: 34
ngncngnant ngnt                                                       14

<210> SEQ ID NO 35
<211> LENGTH: 19
<212> TYPE: RNA
<213> ORGANISM: Artificial Sequence
<220> FEATURE:
<223> OTHER INFORMATION: Control 2'-o-methylated single strand RNA
```

-continued

```
<220> FEATURE:
<221> NAME/KEY: misc_feature
<222> LOCATION: (1)..(19)
<223> OTHER INFORMATION: modified by 2'-o-methylation

<400> SEQUENCE: 35
uacggacuua agcggcuac                                                    19

<210> SEQ ID NO 36
<211> LENGTH: 18
<212> TYPE: RNA
<213> ORGANISM: Artificial Sequence
<220> FEATURE:
<223> OTHER INFORMATION: LeuCAG3'ts18mer 2'-o-methylated single strand
      RNA
<220> FEATURE:
<221> NAME/KEY: misc_feature
<222> LOCATION: (1)..(18)
<223> OTHER INFORMATION: modified by 2'-o-methylation

<400> SEQUENCE: 36
aucccacucc ugacacca                                                     18

<210> SEQ ID NO 37
<211> LENGTH: 22
<212> TYPE: RNA
<213> ORGANISM: Artificial Sequence
<220> FEATURE:
<223> OTHER INFORMATION: LeuCAG3'ts21mer 2'-o-methylated single strand
      RNA
<220> FEATURE:
<221> NAME/KEY: misc_feature
<222> LOCATION: (1)..(22)
<223> OTHER INFORMATION: modified by 2'-o-methylation

<400> SEQUENCE: 37
ucguauccca cuccugacac ca                                                22

<210> SEQ ID NO 38
<211> LENGTH: 26
<212> TYPE: RNA
<213> ORGANISM: Artificial Sequence
<220> FEATURE:
<223> OTHER INFORMATION: LeuCAG3'ts26mer 2'-o-methylated single strand
      RNA
<220> FEATURE:
<221> NAME/KEY: misc_feature
<222> LOCATION: (1)..(26)
<223> OTHER INFORMATION: modified by 2'-o-methylation

<400> SEQUENCE: 38
ggguucgaau cccacuccug acacca                                            26

<210> SEQ ID NO 39
<211> LENGTH: 56
<212> TYPE: DNA
<213> ORGANISM: Artificial Sequence
<220> FEATURE:
<223> OTHER INFORMATION: scramble sense oligonucleotide for target
      sequences in luciferase vector

<400> SEQUENCE: 39
acacgtcgac gtatatagct cattcatgca tacacgtcga cgtatatagc tcattc           56

<210> SEQ ID NO 40
<211> LENGTH: 56
<212> TYPE: DNA
<213> ORGANISM: Artificial Sequence
<220> FEATURE:
```

```
<223> OTHER INFORMATION: Scramble anti sense oligonucleotide for target
      sequences in luciferase vector

<400> SEQUENCE: 40
gaatgagcta tatacgtcga cgtgtatgca tgaatgagct atatacgtcg acgtgt      56

<210> SEQ ID NO 41
<211> LENGTH: 56
<212> TYPE: DNA
<213> ORGANISM: Artificial Sequence
<220> FEATURE:
<223> OTHER INFORMATION: LeuCAG3'tsPM S oligonucleotide for target
      sequences in luciferase vector

<400> SEQUENCE: 41
tggtgtcagg agtgggattc gaaccatgca ttggtgtcag gagtgggatt cgaacc      56

<210> SEQ ID NO 42
<211> LENGTH: 57
<212> TYPE: DNA
<213> ORGANISM: Artificial Sequence
<220> FEATURE:
<223> OTHER INFORMATION: LeuCAG3'tsPM AS oligonucleotide for target
      sequences in luciferase vector

<400> SEQUENCE: 42
ggttcgaatc ccactcctga caccaatgca tggttcgaat cccactcctg acaccat     57

<210> SEQ ID NO 43
<211> LENGTH: 56
<212> TYPE: DNA
<213> ORGANISM: Artificial Sequence
<220> FEATURE:
<223> OTHER INFORMATION: SerGCT3'tsPM S oligonucleotide for target
      sequences in luciferase vector

<400> SEQUENCE: 43
tggcgacgag gatgggatac gaacccagtc tggcgacgag gatgggatac gaaccc      56

<210> SEQ ID NO 44
<211> LENGTH: 56
<212> TYPE: DNA
<213> ORGANISM: Artificial Sequence
<220> FEATURE:
<223> OTHER INFORMATION: SerGCT3'tsPM AS oligonucleotide for target
      sequences in luciferase vector

<400> SEQUENCE: 44
gggttcgtat cccatcctcg tcgccagact gggttcgtat cccatcctcg tcgcca      56

<210> SEQ ID NO 45
<211> LENGTH: 58
<212> TYPE: DNA
<213> ORGANISM: Artificial Sequence
<220> FEATURE:
<223> OTHER INFORMATION: AspGTC3'tsPM S oligonucleotide for target
      sequences in luciferase vector

<400> SEQUENCE: 45
tggctccccg tcggggaatc gaacccagt ctggctcccc gtcggggaat cgaacccc     58

<210> SEQ ID NO 46
<211> LENGTH: 58
<212> TYPE: DNA
<213> ORGANISM: Artificial Sequence
<220> FEATURE:
<223> OTHER INFORMATION: ASPGTC3'tsPM AS oligonucleotide for target
``` sequences in luciferase vector

<400> SEQUENCE: 46
ggggttcgat tccccgacgg ggagccagac tggggttcga ttccccgacg gggagcca    58

<210> SEQ ID NO 47
<211> LENGTH: 28
<212> TYPE: DNA
<213> ORGANISM: Artificial Sequence
<220> FEATURE:
<223> OTHER INFORMATION: Let-7PM S oligonucleotide for target sequences
      in luciferase vector

<400> SEQUENCE: 47
ctagaaacta tacaacctac ttttatag                                     28

<210> SEQ ID NO 48
<211> LENGTH: 28
<212> TYPE: DNA
<213> ORGANISM: Artificial Sequence
<220> FEATURE:
<223> OTHER INFORMATION: Let-7PM AS oligonucleotide for target sequences
      in luciferase vector

<400> SEQUENCE: 48
aattctgagg tagtaggttg tatagttt                                     28

<210> SEQ ID NO 49
<211> LENGTH: 20
<212> TYPE: DNA
<213> ORGANISM: Artificial Sequence
<220> FEATURE:
<223> OTHER INFORMATION: SerGCT5'ts oligonucleotide for northern probe

<400> SEQUENCE: 49
aaccactcgg ccacctcgtc                                              20

<210> SEQ ID NO 50
<211> LENGTH: 18
<212> TYPE: DNA
<213> ORGANISM: Artificial Sequence
<220> FEATURE:
<223> OTHER INFORMATION: SerGCT3'ts oligonucleotide for northern probe

<400> SEQUENCE: 50
cgacgagggt gggattcg                                                18

<210> SEQ ID NO 51
<211> LENGTH: 18
<212> TYPE: DNA
<213> ORGANISM: Artificial Sequence
<220> FEATURE:
<223> OTHER INFORMATION: Asp GTC3'ts oligonucleotide for northern probe

<400> SEQUENCE: 51
ctccccgtcg gggaatcg                                                18

<210> SEQ ID NO 52
<211> LENGTH: 22
<212> TYPE: DNA
<213> ORGANISM: Artificial Sequence
<220> FEATURE:
<223> OTHER INFORMATION: LeuCAG5'ts oligonucleotide for northern probe

<400> SEQUENCE: 52
tagaccgctc ggccatcctg ac                                           22

<210> SEQ ID NO 53
<211> LENGTH: 19
<212> TYPE: DNA
<213> ORGANISM: Artificial Sequence
<220> FEATURE:
<223> OTHER INFORMATION: LeuCAG3'ts oligonucleotide for northern probe

<400> SEQUENCE: 53
gtgtcaggag tgggattcg                                                    19

<210> SEQ ID NO 54
<211> LENGTH: 20
<212> TYPE: DNA
<213> ORGANISM: Artificial Sequence
<220> FEATURE:
<223> OTHER INFORMATION: MetCAT I 3'ts oligonucleotide for northern
      probe

<400> SEQUENCE: 54
gtagcagagg atggtttcga                                                   20

<210> SEQ ID NO 55
<211> LENGTH: 20
<212> TYPE: DNA
<213> ORGANISM: Artificial Sequence
<220> FEATURE:
<223> OTHER INFORMATION: MetCAT e 3'ts oligonucleotide for northern
      probe

<400> SEQUENCE: 55
gtgccccgtg tgaggatcga                                                   20

<210> SEQ ID NO 56
<211> LENGTH: 21
<212> TYPE: DNA
<213> ORGANISM: Artificial Sequence
<220> FEATURE:
<223> OTHER INFORMATION: miR-15a oligonucleotide for northern probe

<400> SEQUENCE: 56
acaaaccatt atgtgctgct a                                                 21

<210> SEQ ID NO 57
<211> LENGTH: 22
<212> TYPE: DNA
<213> ORGANISM: Artificial Sequence
<220> FEATURE:
<223> OTHER INFORMATION: let-7 oligonucleotide for northern probe

<400> SEQUENCE: 57
aactatacaa cctactacct ca                                                22

<210> SEQ ID NO 58
<211> LENGTH: 23
<212> TYPE: DNA
<213> ORGANISM: Artificial Sequence
<220> FEATURE:
<223> OTHER INFORMATION: oligonucleotide for northern probe

<400> SEQUENCE: 58
gacaggccgg gacaagtgca ata                                               23

<210> SEQ ID NO 59
<211> LENGTH: 26
<212> TYPE: DNA

<210> SEQ ID NO 59
<211> LENGTH: 26
<212> TYPE: DNA
<213> ORGANISM: Artificial Sequence
<220> FEATURE:
<223> OTHER INFORMATION: 28S oligonucleotide for northern probe

<400> SEQUENCE: 59
aacgatcaga gtagtggtat ttcacc                                26

<210> SEQ ID NO 60
<211> LENGTH: 20
<212> TYPE: DNA
<213> ORGANISM: Artificial Sequence
<220> FEATURE:
<223> OTHER INFORMATION: 18S oligonucleotide for northern probe

<400> SEQUENCE: 60
cggaactacg acggtatctg                                       20

<210> SEQ ID NO 61
<211> LENGTH: 35
<212> TYPE: DNA
<213> ORGANISM: Artificial Sequence
<220> FEATURE:
<223> OTHER INFORMATION: ETS1 oligonucleotide for northern probe

<400> SEQUENCE: 61
gagagcacga cgtcaccaca tcgatcacga agagc                      35

<210> SEQ ID NO 62
<211> LENGTH: 29
<212> TYPE: DNA
<213> ORGANISM: Artificial Sequence
<220> FEATURE:
<223> OTHER INFORMATION: 5'-ITS1 oligonucleotide for northern probe

<400> SEQUENCE: 62
gcctcgccct ccgggctccg ttaatgatc                             29

<210> SEQ ID NO 63
<211> LENGTH: 26
<212> TYPE: DNA
<213> ORGANISM: Artificial Sequence
<220> FEATURE:
<223> OTHER INFORMATION: ITS2b oligonucleotide for northern probe

<400> SEQUENCE: 63
gctgcgaggg aaccccagc cgcgca                                 26

<210> SEQ ID NO 64
<211> LENGTH: 33
<212> TYPE: DNA
<213> ORGANISM: Artificial Sequence
<220> FEATURE:
<223> OTHER INFORMATION: PRDM10 5'UTR forward oligonucleotide for PCR
      amplification

<400> SEQUENCE: 64
atgcagagct caacatagca aggtagatat cac                        33

<210> SEQ ID NO 65
<211> LENGTH: 33
<212> TYPE: DNA
<213> ORGANISM: Artificial Sequence
<220> FEATURE:
<223> OTHER INFORMATION: PRDM10 5'UTR reverse oligonucleotide for PCR
      amplification

<400> SEQUENCE: 65
atgcagctag ctttaaacag ctcaggcagg ctg                                    33

<210> SEQ ID NO 66
<211> LENGTH: 33
<212> TYPE: DNA
<213> ORGANISM: Artificial Sequence
<220> FEATURE:
<223> OTHER INFORMATION: PRDM10 3'UTR forward oligonucleotide for PCR
      amplification

<400> SEQUENCE: 66
atgcagatat ccttccaccc tggagcttga atc                                    33

<210> SEQ ID NO 67
<211> LENGTH: 31
<212> TYPE: DNA
<213> ORGANISM: Artificial Sequence
<220> FEATURE:
<223> OTHER INFORMATION: PRDM10 3'UTR reverse oligonucleotide for PCR
      amplification

<400> SEQUENCE: 67
atgcactgca ggcttcacac atacaaacat g                                      31

<210> SEQ ID NO 68
<211> LENGTH: 21
<212> TYPE: DNA
<213> ORGANISM: Artificial Sequence
<220> FEATURE:
<223> OTHER INFORMATION: NOP_cDNA forward oligonucleotide for PCR
      amplification

<400> SEQUENCE: 68
atgtttctcc agtattacct c                                                 21

<210> SEQ ID NO 69
<211> LENGTH: 22
<212> TYPE: DNA
<213> ORGANISM: Artificial Sequence
<220> FEATURE:
<223> OTHER INFORMATION: Nop10_cDNA reverse oligonucleotide for PCR
      amplification

<400> SEQUENCE: 69
tcagaggaca gggcgcggtt gc                                                22

<210> SEQ ID NO 70
<211> LENGTH: 25
<212> TYPE: DNA
<213> ORGANISM: Artificial Sequence
<220> FEATURE:
<223> OTHER INFORMATION: RPS28_cDNA forward oligonucleotide for PCR
      amplification

<400> SEQUENCE: 70
gccgccatgg acaccagccg tgtgc                                             25

<210> SEQ ID NO 71
<211> LENGTH: 21
<212> TYPE: DNA
<213> ORGANISM: Artificial Sequence
<220> FEATURE:
<223> OTHER INFORMATION: RPS28_cDNA reverse oligonucleotide for PCR
      amplification

<400> SEQUENCE: 71
tcagcgcaac ctccgggctt c                                              21

<210> SEQ ID NO 72
<211> LENGTH: 33
<212> TYPE: DNA
<213> ORGANISM: Artificial Sequence
<220> FEATURE:
<223> OTHER INFORMATION: RPS6_cDNA forward oligonucleotide for PCR
      amplification

<400> SEQUENCE: 72
atgcatgata tcatgaagct gaacatctcc ttc                                 33

<210> SEQ ID NO 73
<211> LENGTH: 34
<212> TYPE: DNA
<213> ORGANISM: Artificial Sequence
<220> FEATURE:
<223> OTHER INFORMATION: RPS6_cDNA reverse oligonucleotide for PCR
      amplification

<400> SEQUENCE: 73
atgcatgaat tcttatttct gactggattc agac                                34

<210> SEQ ID NO 74
<211> LENGTH: 31
<212> TYPE: DNA
<213> ORGANISM: Artificial Sequence
<220> FEATURE:
<223> OTHER INFORMATION: RPS23_cDNA forward oligonucleotide for PCR
      amplification

<400> SEQUENCE: 74
atgcatgata tcatgggcaa gtgtcgtgga c                                   31

<210> SEQ ID NO 75
<211> LENGTH: 34
<212> TYPE: DNA
<213> ORGANISM: Artificial Sequence
<220> FEATURE:
<223> OTHER INFORMATION: RPS23_cDNA reverse oligonucleotide for PCR
      amplification

<400> SEQUENCE: 75
atgcatgaat tcttatgatc ttggtctttc cttc                                34

<210> SEQ ID NO 76
<211> LENGTH: 20
<212> TYPE: DNA
<213> ORGANISM: Artificial Sequence
<220> FEATURE:
<223> OTHER INFORMATION: RPS13_cDNA forward oligonucleotide for PCR
      amplification

<400> SEQUENCE: 76
tcggctttac cctatcgacg                                                20

<210> SEQ ID NO 77
<211> LENGTH: 20
<212> TYPE: DNA
<213> ORGANISM: Artificial Sequence
<220> FEATURE:
<223> OTHER INFORMATION: RPS13_cDNA reverse oligonucleotide for PCR
      amplification

<400> SEQUENCE: 77
caaacggtga atccggctct                                                20

```
<210> SEQ ID NO 78
<211> LENGTH: 86
<212> TYPE: RNA
<213> ORGANISM: Homo sapiens

<400> SEQUENCE: 78
gucaggaugg ccgagcgguc uaaggcgcug cguucagguc gcagucuccc cuggaggcgu    60
ggguucgaau cccacuccug acacca                                        86
```